US012622876B2

(12) United States Patent
Williams et al.

(10) Patent No.:  US 12,622,876 B2
(45) Date of Patent:       May 12, 2026

(54) METHODS OF SUPPRESSING DELIVERY OF EXOSOMES TO LIVER AND SPLEEN

(71) Applicant: LONZA SALES AG, Basel (CH)

(72) Inventors: Douglas E. Williams, Woburn, MA (US); John D. Kulman, Woburn, MA (US)

(73) Assignee: LONZA SALES AG, Basel (CH)

( * ) Notice: Subject to any disclaimer, the term of this patent is extended or adjusted under 35 U.S.C. 154(b) by 975 days.

(21) Appl. No.: 16/327,282

(22) PCT Filed: Aug. 21, 2017

(86) PCT No.: PCT/US2017/047794
§ 371 (c)(1),
(2) Date: Feb. 20, 2020

(87) PCT Pub. No.: WO2018/039119
PCT Pub. Date: Mar. 1, 2018

(65) Prior Publication Data
US 2021/0290556 A1      Sep. 23, 2021

Related U.S. Application Data

(60) Provisional application No. 62/378,122, filed on Aug. 22, 2016.

(51) Int. Cl.
*A61K 9/00*          (2006.01)
*A61K 9/50*          (2006.01)
(Continued)

(52) U.S. Cl.
CPC .......... *A61K 9/5068* (2013.01); *A61K 9/0019* (2013.01); *A61K 9/0029* (2013.01);
(Continued)

(58) Field of Classification Search
CPC .................................................. A61K 9/5068
See application file for complete search history.

(56) References Cited

U.S. PATENT DOCUMENTS 5,059,535  A  *  10/1991  Mazid .................. C12N 9/1081
                                                                          435/193
2014/0348904  A1    11/2014  Wood et al.
2015/0216899  A1     8/2015  Pusic et al.

FOREIGN PATENT DOCUMENTS

WO      WO-2000054057  A1      9/2000
WO      WO-2014028493  A1      2/2014
(Continued)

OTHER PUBLICATIONS

Masyuk, Exosomes in the pathogenesis, diagnostics, and therapeutics of liver diseases, Journal of Hepatology, 2013, 59, 621-625 (Year: 2013).*

(Continued)

*Primary Examiner* — Paul W Dickinson
(74) *Attorney, Agent, or Firm* — MEDLER FERRO WOODHOUSE & MILLS PLLC

(57)                      ABSTRACT
The instant application describes improved methods and compositions for the systemic delivery of therapeutic exosomes to a subject in need thereof. In certain embodiments, the current invention reduces the amount of exosomes delivered to liver, spleen and combinations thereof to allow greater distribution to other areas of the body such as, but not limited to, the brain, pancreas, lung, kidney, muscle. In certain embodiments, the methods involve the injection of one or multiple doses of non-therapeutic exosomes prior to the injection of a suitable therapeutic dose of exosomes with a therapeutic payload. Also included are methods to improve immune clearance of exosomes in subjects by inhibiting phagocytosis.

12 Claims, 4 Drawing Sheets

Specification includes a Sequence Listing.

Group 1 animals, imaged with 85-88 µCi of [89Zr]-DFO-labeled 293T exosomes
· Maximum Intensity Projections from static scans at 4 and 24 hours Animal 1330          Animal 1331          Animal 1332          Animal 1333

(51) Int. Cl.

| | | |
|---|---|---|
| *A61K 31/713* | (2006.01) | |
| *A61K 48/00* | (2006.01) | |
| *A61K 49/00* | (2006.01) | |
| *A61K 49/18* | (2006.01) | |
| *A61K 51/12* | (2006.01) | |
| *C12N 15/113* | (2010.01) | |

(52) U.S. Cl.

CPC ............ *A61K 31/713* (2013.01); *A61K 48/00* (2013.01); *A61K 49/0097* (2013.01); *A61K 49/1896* (2013.01); *A61K 51/1203* (2013.01); *C12N 15/113* (2013.01); *C12N 2310/14* (2013.01); *C12N 2310/141* (2013.01); *C12N 2320/32* (2013.01); *C12N 2320/35* (2013.01)

(56) References Cited

FOREIGN PATENT DOCUMENTS

| | | |
|---|---|---|
| WO | WO-2015002956 A1 | 1/2015 |
| WO | WO-2015073587 A2 | 5/2015 |
| WO | WO-2015161184 A1 | 10/2015 |
| WO | WO-2018039119 A1 | 3/2018 |

OTHER PUBLICATIONS

Li, Exosomes Derived from Human Umbilical Cord Mesenchymal Stem Cells Alleviate Liver Fibrosis, Stem Cells and Development, 22(6), 2013, 845-854 (Year: 2013).*

Arenzana-Seisdedos, F., et al., "HIV blocked by chemokine antagonist," *Nature* 383(6599):400, Nature Publishing Group, United Kingdom (1996).

Bierhuizen, M.F., et al., "Efficient detection and selection of immature rhesus monkey and human CD34+ hematopoietic cells expressing the enhanced green fluorescent protein (EGFP)," *Leukemia* 13(4):605-613, Nature Publishing Group, United Kingdom (1999).

Bobrie, A., et al., "Exosome secretion: molecular mechanisms and roles in immune responses," *Traffic* 12(12):1659-1668, Wiley-Blackwell, United Kingdom (2011).

Bratosin, D., et al., "Molecular mechanisms of erythrophagocytosis: flow cytometric quantitation of in vitro erythrocyte phagocytosis by macrophages," *Cytometry* 30(5):269-274, John Wiley and Sons Inc., United States (1997).

Bratosin, D., et al., "Improved storage of erythrocytes by prior leukodepletion: flow cytometric evaluation of stored erythrocytes," *Cytometry* 46(6):351-356, John Wiley and Sons Inc., United States (2001).

Buhler, M., et al., "Tethering RITS to a nascent transcript initiates RNAi- and heterochromatin-dependent gene silencing," *Cell* 125(5):873-886, Cell Press, United States (2006).

Dodge, J.T., et al., "The preparation and chemical characteristics of hemoglobin-free ghosts of human erythrocytes," *Archives of Biochemistry and Biophysics* 100:119-30, Academic Press Inc., United States (1963).

Dodge, J.T., and Phillips, G.B., "Composition of phospholipids and of phospholipid fatty acids and aldehydes in human red cells," *Journal of Lipid Research* 8(6):667-75, American Society for Biochemistry and Molecular Biology Inc., United States (1967).

Genbank, "*Homo sapiens* mRNA for cytochrome P-450, complete cds," Accession No. D00003 N00003, accessed at https://www.ncbi.nlm.nih.gov/nuccore/D00003 on Nov. 4, 2020, 1 page.

Genbank, "Herpes simplex virus type 1 thymidine kinase and 3KBL genes," Accession No. J02224, accessed at https://www.ncbi.nlm.nih.gov/nuccore/J02224 on Nov. 4, 2020, 2 pages.

Genbank, "Human alkaline phosphatase (ALPP) gene, complete cds ," Accession No. J03252 J03512, accessed at https://www.ncbi.nlm.nih.gov/nuccore/J03252 on Nov. 4, 2020, 3 pages.

Genbank, "Human mature alpha-galactosidase A, complete cds," Accession No. M13571, accessed at https://www.ncbi.nlm.nih.gov/nuccore/M13571 on Nov. 4, 2020, 1 page.

Genbank, "Human beta-glucuronidase mRNA, complete cds," Accession No. M15182, accessed at https://www.ncbi.nlm.nih.gov/nuccore/M15182 on Nov. 4, 2020, 2 pages.

Genbank, "Human mast cell carboxypeptidase A mRNA, complete cds," Accession No. M27717, accessed at https://www.ncbi.nlm.nih.gov/nuocore/M27717 on Nov. 4, 2020, 2 pages.

International Search Report and Written Opinion for International Application No. PCT/US2017/047794, ISA/US, Alexandria, Virginia, United States, mailed on Dec. 8, 2017, 12 pages.

Jaiswal, J.K., et al., "Long-term multiple color imaging of live cells using quantum dot bioconjugates," *Nature Biotech* 21(1):47-51, Nature Publishing Group, United Kingdom (2003).

Kaur, S., et al., "CD47-dependent immunomodulatory and angiogenic activities of extracellular vesicles produced by T cells," *Matrix Biology* 37:49-59, Elsevier, Netherlands (Jun. 2, 2014).

Kikly, K., et al., "The IL-23/Th(17) axis: therapeutic targets for autoimmune inflammation," *Curr Opin Immunol* 18(6):670-5, Elsevier Ltd., Netherlands (2006).

Kuypers, F.A., et al., "Survival of rabbit and horse erythrocytes in vivo after changing the fatty acyl composition of their phosphatidylcholine," *Biochim Biophys Acta* 819(2):170-8, Elsevier, Netherlands (1985).

Lee, T.H., et al., "Microvesicles as mediators of intercellular communication in cancer—the emerging science of cellular 'debris'," *Semin Immunopathol* 33(5):455-467, Springer Verlag, Germany (2011).

Lutolf, M.P., and Hubbell, J.A., "Synthesis and physicochemical characterization of end-linked poly(ethylene glycol)-co-peptide hydrogels formed by Michael-type addition," *Biomacromolecules* 4(3):713-22, American Chemical Society, United States (2003).

Martineau, P., et al., "Expression of an antibody fragment at high levels in the bacterial cytoplasm," *J Mol Biol* 280(1):117-127, Academic Press Inc., United States (1998).

Mathivanan, S., and Simpson, R.J., "ExoCarta: A compendium of exosomal proteins and RNA," *Proteomics* 9(21):4997-5000, Wiley-VCH Verlag, Germany (2009).

Montet-Abou, K., et al., "Transfection agent induced nanoparticle cell loading," *Molecular Imaging* 4(3):165-171, SAGE Publications Inc., United States (2005).

Neves, A.A., et al., "Imaging cell surface glycosylation in vivo using "double click" chemistry," *Bioconjugate Chemistry* 24(6):934-941, American Chemical Society, United States (2013).

Olsson, M., "Role of the CD47/SIRP-alpha-interaction in regulation of macrophage phagocytosis," Department of Integrative Medical Biology, Section for Histology and Cell Biology, Umea University, Sweden (2008).

Osten, P., et al., "Viral vectors: a wide range of choices and high levels of service," *Handb Exp Pharmacol* 178:177-199, Springer, Germany (2007).

Palmisano, G., et al., "Characterization of membrane-shed microvesicles from cytokine-stimulated β-cells using proteomics strategies," *Molecular & Cellular Proteomics* 11(8):230-43, American Society for Biochemistry and Molecular Biology Inc., United States (2012).

Papapetrou, E.P., et al., "Genetic modification of hematopoietic stem cells with nonviral systems: past progress and future prospects," *Gene Therapy* 12:S118-S130, Nature Publishing Group, United Kingdom (2005).

Senti, G., et al., "Intralymphatic allergen administration renders specific immunotherapy faster and safer: A randomized controlled trial," *PNAS* 105(46):17908-17912, National Academy of Sciences, United States (2008).

Swee, L.K., et al., "Sortase-mediated modification of αDEC205 affords optimization of antigen presentation and immunization against a set of viral epitopes," *Proc Natl Acad Sci USA* 110(4):1428-33, National Academy of Science, United States (2013).

Swirski, F.K., et al., "A near-infrared cell tracker reagent for multiscopic in vivo imaging and quantification of leukocyte immune responses," *PLoS One* 2(10):e1075, Public Library of Science, United States (2007).

Tao, W., et al., "Enhanced green fluorescent protein is a nearly ideal long-term expression tracer for hematopoietic stem cells, whereas DsRed-express fluorescent protein is not," *Stem Cells* 25(3):670-678, Wiley-Blackwell, United States (2007).

(56) References Cited

OTHER PUBLICATIONS

Vanderbyl, S.L., et al., "Transgene expression after stable transfer of a mammalian artificial chromosome into human hematopoietic cells," *Exp Hematol* 33(12):1470-1476, Elsevier Inc., Netherlands (2005).

Visintin, M., et al., "Selection of antibodies for intracellular function using a two-hybrid in vivo system," *Proc Natl Acad Sci USA* 96(21):11723-11728, Public Library of Science, United States (1999).

Wiklander, O., et al., "Extracellular vesicle in vivo biodistribution is determined by cell source, route of administration and targeting," *Journal of Extracellular Vesicles* 4:26316, 13 pages, Taylor and Francis Ltd., Sweden (Apr. 20, 2015).

Ohno, Shin-ichiro, et al. "Systemically injected exosomes targeted to EGFR deliver antitumor microRNA to breast cancer cells." Molecular Therapy 21(1): 185-191, Elsevier, Netherlands (2013).

\* cited by examiner

FIGURE 1

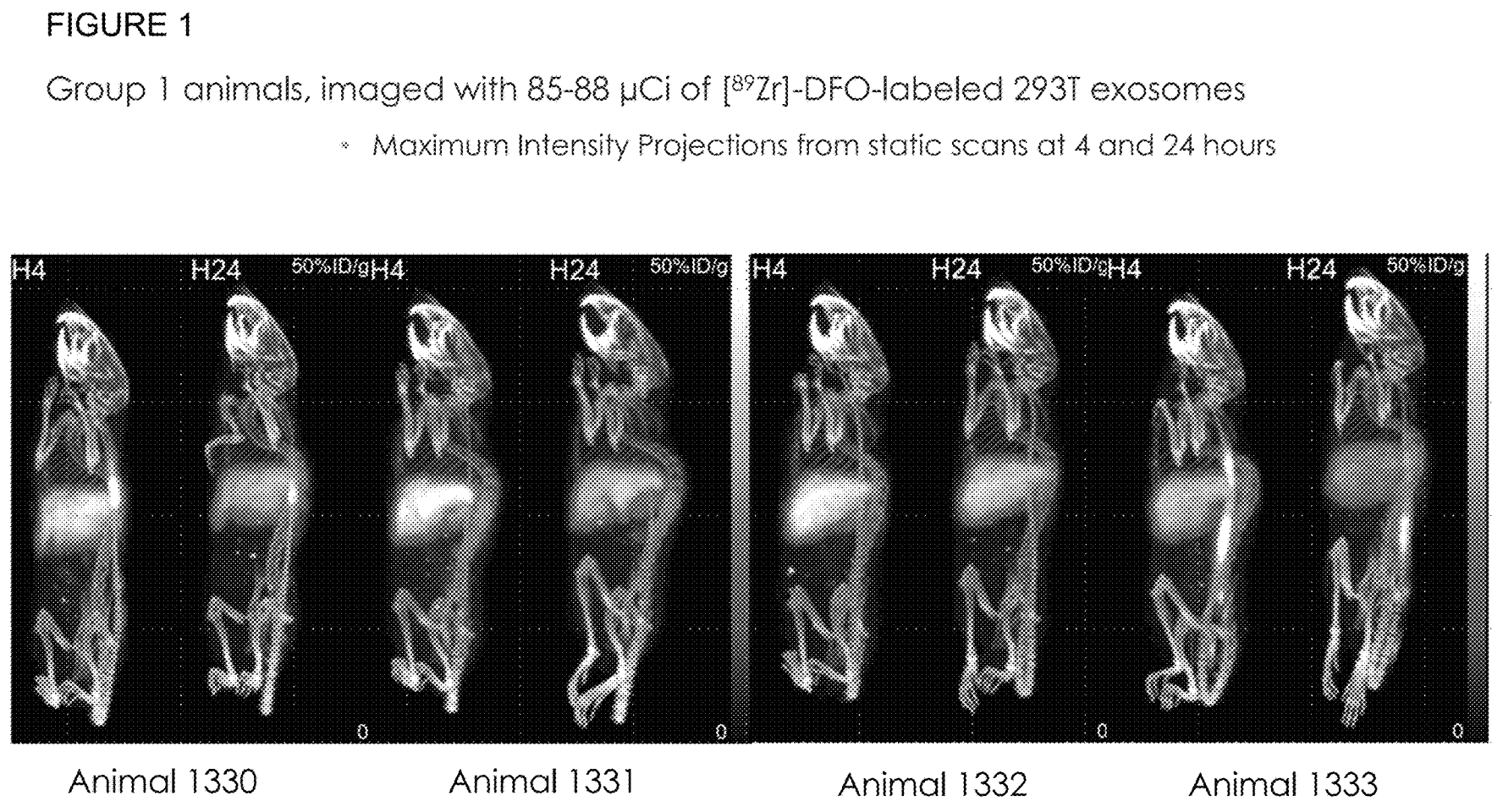

Group 1 animals, imaged with 85-88 µCi of [⁸⁹Zr]-DFO-labeled 293T exosomes

* Maximum Intensity Projections from static scans at 4 and 24 hours

Animal 1330     Animal 1331     Animal 1332     Animal 1333

Group 2 animals, blocked with ~ 0.9 x 10¹¹ 293SF exosomes and imaged with 87-92 µCi of [⁸⁹Zr]-DFO-labeled 293T exosomes

* Maximum Intensity Projections from static scans at 4 and 24 hours

[89Zr]-DFO-exosome (293T) concentration in 293SF-Blocked vs Control, in various organs as determined by gamma counter @ 48 hours post-injection Percent of injected dose of [⁸⁹Zr]-DFO-exosome (293T) in 293SF-Blocked vs Control, in various organs as determined by gamma counter @ 48 hours post-injection

METHODS OF SUPPRESSING DELIVERY OF EXOSOMES TO LIVER AND SPLEEN

CROSS REFERENCE TO RELATED APPLICATIONS

This application claims the benefit of U.S. Patent Application No. 62/378,122 filed Aug. 22, 2016, which is hereby incorporated by reference in its entirety.

BACKGROUND OF THE INVENTION

Field of the Invention

The instant application relates to methods and compositions for introducing exosomes to a subject in need thereof. In certain embodiments, the methods involve the injection of one or multiple doses of non-therapeutic exosomes prior to the injection of a suitable therapeutic dose of exosomes harboring a therapeutic payload. In certain embodiments, the methods are designed to partially block uptake of therapeutic exosomes in the liver and/or spleen so as to enable systemic delivery to other organs and tissues.

Description of the Related Art

Studies in mice have shown that the majority of injected exosomes in normal or diseased mice are deposited in the liver and spleen (Wiklander, O. et al. Extracellular vesicle in vivo biodistribution is determined by cell source, route of administration and targeting. *Journal of Extracellular Vesicles*. Apr. 20 2015). The preferential biodistribution of exosomes to these organs may lead to reduced delivery of exosomes to other tissues of interest or lead to toxic off-target side-effects. Therefore, there is a need for methods and compositions that reduce the amount of exosomes delivered to the liver and spleen to allow greater distribution of exosomes to targets located at other locations and tissue types in the body.

SUMMARY OF THE INVENTION

Disclosed herein are methods and compositions for the delivery of exosomes to a subject in need thereof. In certain aspects are methods of introducing exosomes to a subject, the method comprising, administering to the subject a first dose comprising non-therapeutic exosomes and administering to the subject a second dose comprising therapeutic exosomes. In an embodiment, the therapeutic exosomes optionally comprise a receiver. In certain embodiments, the non-therapeutic and therapeutic exosomes are optionally administered separately. In certain embodiments, the second dose is optionally administered at a period of time which is 15 minutes or greater after administration of the first dose. In certain embodiments, the second dose is administered at a period of time which is three hours or less after administration of the first dose. In certain aspects, the first dose optionally comprises an exosome quantity that is different from an exosome quantity of the second dose. In some aspects, the first dose optionally comprises an exosome quantity that is greater than an exosome quantity of the second dose.

In certain embodiments, the first and second doses are optionally administered parenterally. In some embodiments, the administration is optionally intravenous administration. In certain embodiments, the first dose is optionally a bolus dose comprising an exosome quantity that is greater than an exosome quantity of the second dose, and wherein the second dose is administered as a continuous infusion. In certain embodiments, the first dose is optionally a bolus dose comprising an exosome quantity that is greater than an exosome quantity of the second dose, and the second dose is administered in a plurality of repeated administration steps. In certain embodiments, the first dose is administered in a plurality of repeated administration steps. In some embodiments, the second dose is administered in a time period ranging from 15 minutes to 3 hours after completion of the plurality of repeated administration steps.

In certain embodiments, the non-therapeutic exosomes, the therapeutic exosomes or both the non-therapeutic and therapeutic exosomes optionally comprise an imaging agent. In some embodiments, the imaging agent is a fluorescent compound. In some embodiments, the imaging agent is a radioactive compound. In certain embodiments, the methods further comprise imaging the subject after administration of the non-therapeutic exosomes, the therapeutic exosomes or both the non-therapeutic and therapeutic exosomes and thereby detecting the location of the exosomes in the subject. In some embodiments, the imaging comprises magnetic resonance imaging.

In certain embodiments, the therapeutic exosomes optionally comprise RNA. In certain embodiments, the therapeutic exosomes comprise microRNA (miRNA). In certain embodiments, the therapeutic exosomes comprise siRNA. In certain embodiments, the therapeutic exosomes optionally comprise DNA. In certain embodiments, the therapeutic exosomes optionally comprise a polypeptide. In certain embodiments, the therapeutic exosomes optionally comprise a small molecule. In certain embodiments, the therapeutic exosomes optionally comprise a large molecule biologic.

In certain embodiments, the therapeutic exosomes optionally comprise more than one distinct payload. In certain embodiments, the payload comprises more than one type of payload selected from the group consisting of peptide, protein, DNA, RNA, siRNA, miRNA, shRNA, lncRNA, small molecule, large molecule biologic, polysaccharide, lipid, toxin and combinations thereof.

In certain embodiments, the therapeutic exosomes optionally comprise a payload labeled with a detectable moiety.

In certain embodiments, the therapeutic exosomes, non-therapeutic exosomes or both the therapeutic and non-therapeutic exosomes are synthetic. In certain embodiments, the therapeutic exosomes, non-therapeutic exosomes or both the therapeutic and non-therapeutic exosomes are derived from a producer cell.

In certain embodiments, the exosomes are optionally contacted with sialyltransferase prior to administration.

In certain embodiments, the therapeutic exosomes, non-therapeutic exosomes or both the therapeutic and non-therapeutic exosomes are optionally co-administered either concurrently or sequentially, with an agent that inhibits phagocytosis of the exosomes.

In certain embodiments, the first dose, the second dose or both the first and second doses harbor a plurality of distinct exosomes, wherein the distinct exosomes harbor distinct payloads.

In certain embodiments, the exosomes comprise a largest diameter ranging from 30 nm to 500 nm. In certain embodiments, the exosomes comprise a largest diameter ranging from 30 nm to 200 nm. In certain embodiments, the exosomes comprise a largest diameter ranging from 30 nm to 100 nm.

In certain embodiments, administration of the first dose comprising non-therapeutic exosomes causes reduced delivery of the therapeutic exosomes to an organ selected from the group consisting of: the liver and spleen, or combinations thereof, compared to delivery of the therapeutic exosomes administered at the same dose, but without prior administration of the first dose comprising non-therapeutic exosomes. In certain embodiments, administration of the non-therapeutic exosomes causes increased delivery of the therapeutic exosomes to a target cell or tissue, compared to delivery of therapeutic exosomes administered at the same dose, but without prior administration of the first dose comprising non-therapeutic exosomes.

In certain aspects, are methods comprising administering to the subject a first dose comprising non-therapeutic exosomes and administering to the subject a second dose comprising therapeutic exosomes, wherein administering to the subject the first dose comprises accumulating the non-therapeutic exosomes in the liver or spleen, or any combination thereof, of the subject.

Included with the invention, are kits comprising a first pharmaceutical composition comprising non-therapeutic exosomes, and a second pharmaceutical composition comprising therapeutic exosomes.

In certain aspects, are methods of introducing exosomes to a subject, the method comprising administering to the subject a dose of therapeutic exosomes, wherein the therapeutic exosomes are modified, the modification causing increased delivery of the therapeutic exosomes to a target cell or tissue as compared to delivery of unmodified therapeutic exosomes that have been obtained by identical methods. In certain embodiments, the exosomes are optionally modified by contacting with sialyltransferase prior to administration. In certain embodiments, the exosomes are optionally administered either concurrently or sequentially with an agent that inhibits phagocytosis of the exosomes. In certain embodiments, the exosomes optionally comprise an imaging agent. In some embodiments, the imaging agent is a fluorescent compound. In some embodiments, the imaging agent is a radioactive compound. In certain embodiments, the methods optionally further comprise imaging the subject after administration of the exosomes and thereby detecting the location of the exosomes in the subject. In some embodiments, the imaging comprises magnetic resonance imaging. In certain embodiments, the therapeutic exosomes optionally comprise RNA. In certain embodiments, the therapeutic exosomes comprise microRNA (miRNA). In certain embodiments, the therapeutic exosomes comprise siRNA. In certain embodiments, the therapeutic exosomes optionally comprise DNA. In certain embodiments, the therapeutic exosomes optionally comprise a polypeptide. In certain embodiments, the therapeutic exosomes optionally comprise a small molecule. In certain embodiments, the therapeutic exosomes optionally comprise a large molecule biologic. In certain embodiments, the therapeutic exosomes optionally comprise more than one distinct payload. In certain embodiments, the payload optionally comprises more than one type of payload selected from the group consisting of: peptide, protein, DNA, RNA, siRNA, miRNA, shRNA, lncRNA, small molecule, large molecule biologic, polysaccharide, lipid, toxin and combinations thereof. In certain embodiments, the exosomes optionally comprise a payload labeled with a detectable moiety. In certain embodiments, the exosomes are optionally synthetic. In certain embodiments, the exosomes are optionally derived from a producer cell. In certain embodiments, the exosomes are optionally contacted with sialyltransferase prior to administration. In certain embodiments, the exosomes, are optionally co-administered either concurrently or sequentially, with an agent that inhibits phagocytosis of the exosomes. In certain embodiments, the exosomes comprise a largest diameter ranging from 30 nm to 500 nm. In certain embodiments, the exosomes comprise a largest diameter ranging from 30 nm to 200 nm. In certain embodiments, the exosomes comprise a largest diameter ranging from 30 nm to 100 nm. In certain embodiments, the exosomes optionally comprise a receiver. In certain embodiments, the administration of the modified exosomes causes reduced delivery of the exosomes to an organ selected from the group consisting of: the liver and spleen, or combinations thereof, compared to delivery of unmodified exosomes that have been obtained by identical methods and administered at the same dose.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1 shows whole-body PET/CT images of mice injected solely with $^{89}$Zr-DFO-labeled exosomes at four hours and 24 hours post-injection.

DETAILED DESCRIPTION OF THE INVENTION

Advantages and Utility

Figure 2:
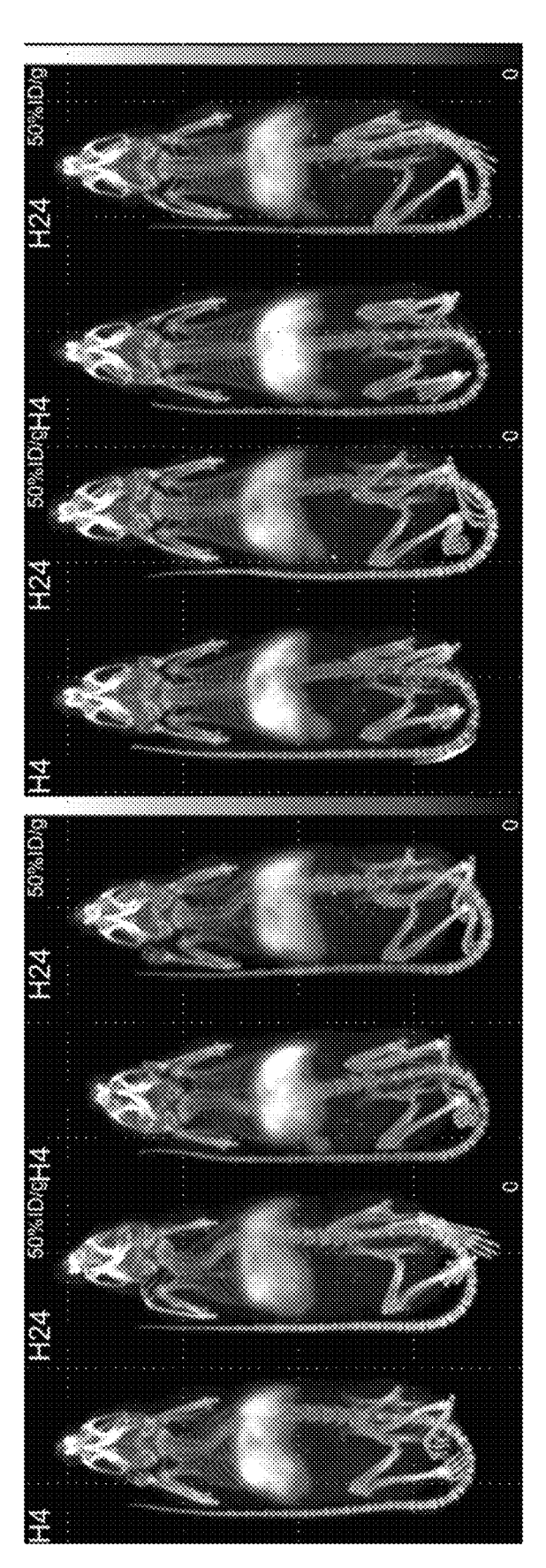
FIG. 2 shows whole-body PET/CT images of mice injected first with unlabeled exosomes, followed by injection with $^{89}$Zr-DFO-labeled exosomes at four hours and 24 hours post-injection.

Briefly, and as described in more detail below, described herein are improved methods for the delivery of therapeutic exosomes to a subject in need thereof. Therapeutic exosomes can confer therapeutic benefits by interacting with, signaling to, or delivering therapeutic molecules to a target cell, tissue or molecule within a subject. It is known in the art that when administered intravenously, exosomes are deposited and accumulate in the liver and/or spleen of mice, leading to unwanted toxicity and/or decreased delivery of exosomes to other targets of interest. Therefore, the in vivo pharmacokinetics and off-target deposition of exosomes needs to be improved for the treatment of tissues and organs other than the liver and spleen. The instant application describes improved methods and compositions for the systemic delivery of therapeutic exosomes to targets of interest. In some embodiments, the current invention reduces the amount of therapeutic exosomes delivered to liver, spleen and combinations thereof to allow greater distribution to other areas in the body such as, but not limited to, the brain, pancreas, lung, kidney and muscle. Also included, are methods to improve immune clearance of exosomes in subjects by inhibiting phagocytosis.

Definitions

Terms used in the claims and specification are defined as set forth below unless otherwise specified.

The term "exosome" refers to cell-derived phospholipid membrane bound vesicles with a diameter between 30 and 500 nm that are present in biological fluids, including blood, urine and cultured medium of cell cultures. Exosomes are either released from the cell when multivesicular bodies fuse with the plasma membrane or they are released directly from the plasma membrane. Exosomes may also be synthetic exosomes. A synthetic exosome refers to an exosome that is not naturally occurring.

The term "exosome delivery" or "delivery of exosomes" refers to the administration and localization of exosomes to target tissues and/or organs of the subject. In some embodiments, the payload can be delivered to the cytoplasm of a target cell. In other embodiments, the payload is delivered to the membrane of the target cell. In some embodiments, the membrane of the exosome fuses with a membrane of a target cell.

The term "non-therapeutic exosome" refers to exosomes that do not harbor at least one therapeutic payload as compared to a therapeutic exosome that is administered to a subject either concurrently or following the administration of the non-therapeutic exosome.

The term "therapeutic exosome" refers to exosomes that harbor at least one therapeutic payload or have been modified to have a desired therapeutic effect as compared to a non-therapeutic exosome that is administered to a subject concurrently or prior to the administration of the therapeutic exosome.

A "therapeutic agent" or "therapeutic molecule" includes a compound or molecule that, when present in an effective amount, produces a desired therapeutic effect, pharmacologic and/or physiologic effect on a subject in need thereof. It includes any compound, e.g., a small molecule drug, or a biologic (e.g., a polypeptide drug or a nucleic acid drug) that when administered to a subject has a measurable or conveyable effect on the subject, e.g., it alleviates or decreases a symptom of a disease, disorder or condition.

The term "payload" refers to an agent delivered by an exosome. A "therapeutic payload" is a "payload" comprising a therapeutic agent. A therapeutic payload can comprise, but is not limited to, a therapeutic polypeptide, nucleic acid (including DNA, RNA, mRNA, miRNA, shRNA, siRNA, dsDNA, lncRNA, siRNA) or other polynucleotide, polysaccharide or glycan, lipid or fatty acid, large molecule biologic, small molecule or toxin.

The term "nucleic acid," refers to any compound and/or substance that is or can be incorporated into an oligonucleotide chain. Exemplary nucleic acids for use in accordance with the present invention include, but are not limited to, one or more of DNA, RNA, hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc., described in detail herein.

The term "receiver" refers to a molecule that directs the exosome to a target and/or promotes the interaction of exosome with the target in the subject. In some embodiments, the receiver is a polypeptide. In some embodiments, the receiver is capable of increasing the concentration of the payload in the tissue of the subject. Examples of receivers include, but are not limited to, examples listed in Table 5.

The term "target" refers to, a cell, a pathogen, a metabolite, a polypeptide complex or any molecule or structure that resides in a tissue or circulates in the circulatory system or lymphatic system of the subject. Examples of targets include, but are not limited to, examples listed in Table 6.

The terms "administration," "administering" and variants thereof refer to introducing a composition, such as an exosome, or agent into a subject and includes concurrent and sequential introduction of a composition or agent. The introduction of a composition or agent into a subject is by any suitable route, including orally, pulmonarily, intranasally, parenterally (intravenously, intramuscularly, intraperitoneally, or subcutaneously), rectally, intralymphatically, intrathecally or topically. Administration includes self-administration and the administration by another. A suitable route of administration allows the composition or the agent to perform its intended function. For example, if a suitable route is intravenous, the composition is administered by introducing the composition or agent into a vein of the subject.

As used herein, the term "antibody" encompasses an immunoglobulin whether natural or partly or wholly synthetically produced, and fragments thereof. The term also covers any protein having a binding domain that is homologous to an immunoglobulin binding domain. These proteins can be derived from natural sources, or partly or wholly synthetically produced. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies; murine antibodies; chimeric, mouse-human, mouse-primate, primate-human monoclonal antibodies, anti-idiotype antibodies, antibody fragments, such as, e.g., scFv, (scFv)2, Fab, Fab', and F(ab')2, F(ab1)2, Fv, dAb, and Fd fragments, diabodies, and antibody-related polypeptides. Antibody includes bispecific antibodies and multispecific antibodies so long as they exhibit the desired biological activity or function.

The term "antigen binding fragment" used herein refers to fragments of an intact immunoglobulin, and any part of a polypeptide including antigen binding regions having the ability to specifically bind to the antigen. For example, the antigen binding fragment can be a F(ab')2 fragment, a Fab' fragment, a Fab fragment, a Fv fragment, or a scFv fragment, but is not limited thereto. A Fab fragment has one antigen binding site and contains the variable regions of a light chain and a heavy chain, the constant region of the light chain, and the first constant region CH1 of the heavy chain. A Fab' fragment differs from a Fab fragment in that the Fab' fragment additionally includes the hinge region of the heavy chain, including at least one cysteine residue at the C-terminal of the heavy chain CH1 region. The F(ab')2 fragment is produced whereby cysteine residues of the Fab' fragment are joined by a disulfide bond at the hinge region. A Fv fragment is the minimal antibody fragment having only heavy chain variable regions and light chain variable regions, and a recombinant technique for producing the Fv fragment is well known in the art. Two-chain Fv fragments can have a structure in which heavy chain variable regions are linked to light chain variable regions by a non-covalent bond. Single-chain Fv (scFv) fragments generally can have a dimer structure as in the two-chain Fv fragments in which heavy chain variable regions are covalently bound to light chain variable regions via a peptide linker or heavy and light chain variable regions are directly linked to each other at the C-terminal thereof. The antigen binding fragment can be obtained using a protease (for example, a whole antibody is digested with papain to obtain Fab fragments, and is digested with pepsin to obtain F(ab')2 fragments), and can be prepared by a genetic recombinant technique. A dAb fragment consists of a VH domain. Single-chain antibody molecules can comprise a polymer with a number of individual molecules, for example, dimmer, trimer or other polymers.

The term "imaging agent" refers to molecules that serve as positive markers that can be used to visibly monitor over time the number or concentration of exosomes in vivo and/or in vitro.

The term "fluorescent compound" refers to imaging agents that produce a fluorescent signal upon excitation. Fluorescent compounds include those that are approved by the Food & Drug Administration for human use including, but not limited to, fluorescein, indocyanin green, and rhodamine B.

The term "detectable moiety" refers to any positive marker that can be used by any means to monitor over time the number or concentration of exosomes in vivo and/or in vitro.

The term "synthetic" when used to modify "exosome" refers to an exosome that is not naturally occurring.

The term "producer cell" refers to a parental cell that produces the exosomes. The producer cells can me mammalian, human or non-mammalian. Parent producer cells can include, but are not limited to, reticulocytes, erythrocytes, megakaryocytes, leukocytes, platelets, neutrophils, mesenchymal stem cells, connective tissue cells, neural cells and tumor cells. In some embodiments, the extracts comprising exosomes are derived from a plurality of donor cell types (e.g. 2, 3, 4, 5, 6, 7, 8, 9, 10, 50, 100, 500, 1000, 5000, or 10000 donor cell types) and are combined or pooled. Producer cells include mammalian cell lines and primary cells. Producer cells include cells grown in culture or cells isolated directly from a donor tissue or subject.

The term "in vivo" refers to processes that occur in a living organism.

The term "mammal" as used herein includes both humans and non-humans mammals.

The term "sufficient amount" means an amount sufficient to produce a desired effect, e.g., an amount sufficient to modulate a condition in the subject.

The term "therapeutically effective amount" is an amount that is effective to ameliorate a symptom of a disease. A therapeutically effective amount can be a "prophylactically effective amount" as prophylaxis can be considered therapy.

As used herein, the term "modulate," "modulating", "modify," and/or "modulator" generally refers to the ability to alter, by increase or decrease, e.g., directly or indirectly promoting/stimulating/upregulating or interfering with/inhibiting/downregulating a specific concentration, level, expression, function or behavior, such as, e.g., to act as an antagonist or agonist. In some instances a modulator can increase and/or decrease a certain concentration, level, activity or function relative to a control, or relative to the average level of activity that would generally be expected or relative to a control level of activity.

The term "pharmaceutically-acceptable" and grammatical variations thereof, refers to compositions, carriers, diluents and reagents capable of administration to or upon a subject without the production of undesirable physiological effects to a degree that would prohibit administration of the composition.

As used herein, the term "substantially" or "substantial" refers, e.g., to the presence, level, or concentration of an entity in a particular space, the effect of one entity on another entity, or the effect of a treatment. For example, an activity, level or concentration of an entity is substantially increased if the increase is 2-fold, 3-fold, 4-fold, 5-fold, 10-fold, 50-fold, 100-fold, or 1000-fold relative to a baseline. An activity, level or concentration of an entity is also substantially increased if the increase is 5%, 10%, 20%, 30%, 40%, 50%, 60%, 70%, 80%, 90%, 100%, 200%, or 500% relative to a baseline.

Abbreviations used in this application include the following: "miRNA" refers to microRNA, "siRNA" refers to small interfering RNA, "shRNA" refers to small or short hairpin RNA and "lncRNA" refers to long non-coding RNA.

It must be noted that, as used in the specification and the appended claims, the singular forms "a," "an" and "the" include plural referents unless the context clearly dictates otherwise.

Exosomes

In some embodiments, the exosome comprises a membrane that forms a particle that has a diameter of 30-100 nm, 30-200 nm or 30-500 nm. In some embodiments, the exosome comprises a membrane that forms a particle that has a diameter of 10-100 nm, 20-100 nm, 30-100 nm, 40-100 nm, 50-100 nm, 60-100 nm, 70-100 nm, 80-100 nm, 90-100 nm, 100-200 nm, 100-150 nm, 150-200 nm, 100-250 nm, 250-500 nm, or 10-1000 nm. In some embodiments, the membrane comprises lipids and fatty acids. In some embodiments, the membrane comprises one or more of phospholipids, glycolipids, fatty acids, sphingolipids, phosphoglycerides, sterols, cholesterols, and phosphatidylserine. In some embodiments, the lipid or fatty acid can be one or more of those listed in Table 3. In addition, the membrane can comprise one or more polypeptides and one or more polysaccharides, such as glycans.

In some embodiments, the exosome is generated by a producer cell (or parental cell), such as, e.g., a mammalian cell. In some embodiments, the membrane of the exosome comprises one or more molecules derived from the producer cell. The exosome can be generated in a cell culture system and isolated (e.g., by separating the exosome from the producer cell). Separation can be achieved by sedimentation. For example, the exosome can have a specific density between 0.5-2.0, 0.6-1.0, 0.7-1.0, 0.8-1.0, 0.9-1.0, 1.0-1.1, 1.1-1.2, 1.2-1.3, 1.4-1.5, 1.0-1.5, 1.5-2.0, and 1.0-2.0 kg/m$^3$.

In some embodiments, the exosome is synthetic. For example, the exosome can comprise a payload, such as, e.g., a therapeutic polypeptide, nucleic acid (such as DNA or RNA) or other polynucleotide, polysaccharide or glycan, lipid or fatty acid, large biologic, small molecule or toxin such that the exosome is not naturally occurring. In some embodiments, the exosome is modified (e.g., by introducing a payload or otherwise modifying the content of the complex, such as by changing the protein, lipid or glycan content of the membrane). For example, exosomes are first isolated from a producer cell and then modified as desired, thereby generating synthetic exosomes. In some embodiments, the producer cell is modified. For example, an exogenous nucleic acid, an exogenous polypeptide or small molecule or toxin can be introduced into to the producer cell. Alternatively or in addition, the producer cell can otherwise be modified (e.g., by modifying the cellular or membrane content, such as by changing the lipid or glycan content of the cell membrane). Exosomes generated from the modified producer cells comprise one or more of the modifications of the producer cell. The process produces synthetic exosomes. In some embodiments, both the producer cell and the exosome isolated from the producer cell are modified as described herein.

In some embodiments, the exosome delivers the payload (therapeutic agent) to a target. The payload is a therapeutic agent that acts on a target (e.g., a target cell) that is contacted with the exosome. Contacting can occur (e.g., in vitro) or in a subject. Payloads that can be introduced into an exosome and/or a producer cell include therapeutic agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, siRNA), amino acids (e.g., amino acids comprising a detectable moiety or a toxin or that disrupt translation), polypeptides (e.g., enzymes), lipids, carbohydrates, and small molecules (e.g., small molecule drugs and toxins). The payload can comprise nucleotides (e.g., nucleotides that are labeled with a detectable or cytotoxic moiety, such as a radiolabel).

In some embodiments, the exosome comprises nucleotides and/or polynucleotides (e.g., nucleic acids). For example, the exosome can comprise RNA, DNA, mRNA, miRNA, dsDNA, lncRNA, siRNA, or singular nucleotides. In some embodiments, the exosome comprises one or more of the miRNAs listed in Table 7. In some embodiments, the nucleotides and polynucleotides are synthetic. For example, an exogenous nucleic acid can be introduced into the exosome and/or the producer cell. In some embodiments, the nucleic acid is DNA that can be transcribed into an RNA (e.g., a siRNA or mRNA) and in the case of an mRNA can be translated into a desired polypeptide. In some embodiments, the nucleic acid is an RNA (e.g., an siRNA or mRNA) and in the case of an mRNA can be translated into a desired polypeptide.

In some embodiments, the exosome comprises a nucleic acid, such as a RNA, DNA mRNA, miRNA, siRNA, dsDNA, lncRNA or siRNA. The nucleic acid is delivered to a target cell as a payload. The target cell can transcribe a DNA payload into an RNA such as a siRNA. In case a mRNA is transcribed by the target cell from the DNA payload, the cell can translate the mRNA into a polypeptide (e.g., therapeutic polypeptide). The target cell can also translate a delivered mRNA payload into a polypeptide.

In some embodiments, the producer cell comprises a nucleic acid that can be transcribed (e.g., a DNA can be transcribed into a siRNA or mRNA), and in certain embodiments, mRNA is made the mRNA can be translated by the producer cell into a polypeptide. The producer cell can also be modified with a non-translatable RNA (e.g., siRNA) or mRNA. In case an mRNA is transferred the producer cell can translate the mRNA into a polypeptide. Exosomes derived from the producer cell can then carry the non-translatable RNA, the transcribed RNA or the translated polypeptide as a payload.

The exosome can interact with the target cell via membrane fusion and deliver payloads (e.g., therapeutic agents) in an exosome composition to the surface or cytoplasm of a target cell. In some embodiments, membrane fusion occurs between the exosome and the plasma membrane of a target cell. In other embodiments, membrane fusion occurs between the exosome and an endosomal membrane of a target cell.

In some embodiments, the exosome comprises polypeptides on its surface selected from CD47, CD55, CD40, CD63, CD9, CD81, CD133 and CD59. In some embodiments, the exosome is modified to contain the one or more polypeptides. In some embodiments, the producer cell is modified to contain the one or more polypeptides. In some embodiments, the producer cell naturally contains the one or more polypeptides and exosomes derived therefrom also contain the polypeptides. The levels of any desired surface marker can be modified directly on the exosome (e.g., by contacting the complex with recombinantly produced polypeptides to bring about insertion in or conjugation to the membrane of the complex). Alternatively or in addition, the levels of any desired surface marker can be modified directly on the producer cell (e.g., by contacting the complex with recombinantly produced polypeptides to bring about insertion in or conjugation to the membrane of the cell). Alternatively, the producer cell can be modified by transducing an exogenous nucleic acid into the producer cell to express a desired surface marker. The surface marker can already be naturally present on the producer cell, in which case the exogenous construct can lead to overexpression of the marker and increased concentration of the marker in or on the producer cell. Alternatively, a naturally expressed surface marker can be removed from the producer cell (e.g., by inducing gene silencing in the producer cell). The polypeptides can confer different functionalities to the exosome (e.g., specific targeting capabilities, delivery functions (e.g., fusion molecules), enzymatic functions, increased or decreased half-life in vivo, etc). In some embodiments, the polypeptides include, but are not limited to CD47, CD55, CD49, CD40, CD133, CD59, glypican-1, CD9, CD63, CD81, integrins, selectins, lectins, and cadherins.

In some embodiments, the exosome comprises a receiver polypeptide. The receiver polypeptide can be synthetic. In some embodiments, the receiver polypeptide is introduced into the producer cell (e.g., an exogenous nucleic acid that encodes the receiver polypeptide is introduced into the producer cell) or a recombinant receiver polypeptide that is made outside the producer cell (e.g., synthesized by a protein expression system). In some embodiments, the receiver polypeptide (e.g., a recombinantly produced polypeptide) is introduced into the exosome directly (e.g., after the exosome is isolated from the producer cell). In some embodiments, the receiver polypeptide can be on the surface of the exosomes. In some embodiments, the receiver polypeptide is capable of targeting the exosome to a specific target (e.g., a target such as a pathogen, a metabolite, a polypeptide complex or a cell such as non-functional cell or cancer cell) that circulates in the circulatory system of the subject, such as the blood, or a target that resides in a tissue (such as a diseased tissue).

Membrane Compositions of the Exosomes

Exosomes, exosome-like vesicles, matrix vesicles, microparticles, nanovesicles, oncosomes, prostasomes, secreted vesicles, microvesicles, ectosomes, and apoptotic bodies have been found to mediate interaction between cells, mediate non-classical protein secretion, facilitating processes such as antigen presentation, in trans signaling to neighboring cells and transfer of RNAs and protein. These vesicles are secreted by different cell types/tissues and harbor a common set of molecules that are essential for their structure and trafficking apart from distinct subsets of proteins/RNA, which, presumably, reflect the biological function of the producer cell. (Mathivanan, S et al Exocarta—A compendium of exosomal proteins and RNA, Proteomics (2009)).

In some embodiments, exosome compositions are comprised of proteins, lipids, sugars, and nucleotides. In some embodiments, exosomes have a cholesterol-rich lipid membrane comprising one or more of sphingomyelin, ceramide, lipid rafts and exposed phosphatidylserine.

Exosome compositions can comprise adhesion molecules, signaling molecules, soluble proteins, T-cell stimulating molecules, transmembrane molecules, membrane trafficking proteins, cytoskeleton components, chaperones, lipid rafts, or nucleotides.

1. Lipids

In an embodiment, the exosome comprises a membrane that sediments at approximately 1,000-200,000×g and comprises a density of approximately 0.8-1.4 g/ml. In some embodiments, exosomes have a density in sucrose of about 1.10 to 1.19 g/ml, sedimented at 100,000×g, or about 1.0 to 1.3 g/ml. The mass of the membrane component can be assessed by separating it from the remainder of the complex using hypotonic solutions of mildly alkaline buffer (see e.g., protocols in Dodge et al 1963, Arch Biochem Biophys 100:119).

The exosome comprises a membrane. In some embodiments, the membrane comprises phosphatidylcholine, sphingomyelin, lysophosphatidylcholine, phosphatidylethanolamine, phosphatidylserine, phosphatidylinositol, or phosphatidic acid. In some embodiments, the membrane is a cell membrane.

In an embodiment, the exosome comprises lipid molecules of the class of choline phospholipids, acidic phospholipids, and phosphatidylethanolamine.

In an embodiment, the exosome comprises phosphatidylcholine, sphingomyelin, lysophosphatidylcholine, phosphatidylethanolamine, phosphatidylserine, phosphatidylinositol, or phosphatidic acid.

In some embodiments exosome comprises ceramine, lipid rafts, exposed phosphatidylserine, or diaclglycerol.

In some embodiments exosomes comprise lipids.

In an embodiment, the exosome comprises choline phospholipids in an approximate amount of 50%, 51%, 52%, 53%, 54%, 55%, 56%, 57%, 58%, 59%, 60%, 61%, 62%, 63%, 64%, or 65% relative to the total lipid content of the complex.

In an embodiment, the exosome comprises acidic phospholipids in an approximate amount of 5%, 6%, 7%, 8%, 9%, 10%, 11%, 12%, 13%, 14%, 15%, 16%, 17%, 18%, 19%, or 20% relative to the total lipid content of the complex.

In an embodiment, the exosome comprises phosphatidylcholine in an amount greater than 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or greater than 50% relative to the total lipid content of the complex.

In an embodiment, the exosome comprises sphingomyelin in an amount greater than 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or greater than 50% relative to the total lipid content of the complex.

In an embodiment, the exosome comprises lysophosphatidylcholine in an amount greater than 0.1%, 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, or greater than 10% relative to the total lipid content of the complex.

In an embodiment, the exosome comprises phosphatidylethanolamine in an amount greater than 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or greater than 50% relative to the total lipid content of the complex.

In an embodiment, the exosome comprises phosphatidylserine in an amount greater than 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or greater than 50% relative to the total lipid content of the complex.

In an embodiment, the exosome comprises phosphatidylinositol in an amount greater than 0.1%, 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, or greater than 10% relative to the total lipid content of the complex.

In an embodiment, the exosome comprises phosphatidic acid in an amount greater than 0.1%, 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, or greater than 10% relative to the total lipid content of the complex.

In an embodiment, the exosome comprises molecules from at least one, two, or three, of the following classes of molecules, including, but not limited to, choline phospholipids, acidic phospholipids, and phosphatidylethanolamine.

In an embodiment, the molar ratio of choline phospholipids to acidic phospholipids in the exosome is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In an embodiment, the molar ratio of choline phospholipids to phosphatidyl ethanolamine in the exosome is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In an embodiment, the molar ratio of phosphatidylethanolamine to acidic phospholipids in the exosome is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In an embodiment, the exosome comprises molecules from at least one, two, three, four, five, six, or seven of the following classes of molecules, including, but not limited to, phosphatidylcholine, sphingomyelin, lysophosphatidylcholine, phosphatidylethanolamine, phosphatidylserine, phosphatidylinositol, or phosphatidic acid.

In an embodiment, the exosome comprises at least one lipid selected from Table 3.

The lipid composition of the exosome can be experimentally measured using methods known in the art including, e.g., gas-liquid chromatography or thin layer chromatography, see for example, Dodge & Phillips, J Lipid Res 1967 8:667.

In an embodiment, the exosome comprises a lipid bilayer composed of an inner leaflet and an outer leaflet. The composition of the inner and outer leaflet can be determined by transbilayer distribution assays known in the art, see e.g., Kuypers et al. Biohim Biophys Acta 1985 819:170. In an embodiment, the composition of the outer leaflet is between approximately 70-90% choline phospholipids, between approximately 0-15% acidic phospholipids, and between approximately 5-30% phosphatidylethanolamine. In an embodiment, the composition of the inner leaflet is between approximately 15-40% choline phospholipids, between approximately 10-50% acidic phospholipids, and between approximately 30-60% phosphatidylethanolamine.

2. Cholesterol

In an embodiment, the exosome comprises cholesterol. In an embodiment, the cholesterol content is between approximately 3.0-5.5 nmol cholesterol per $10^7$ complexes. In an embodiment, the cholesterol content is between approximately 1.8-3.5 nmol cholesterol per $10^7$ complexes. In an embodiment, the cholesterol content accounts for >5 mol % of membrane lipids. In an embodiment, the molar ratio of cholesterol to phospholipids in the complex is between approximately 0.5-1.5. In an embodiment the molar ratio of cholesterol to phospholipids is between approximately 0.8-1.2. In an embodiment the molar ratio of cholesterol to phospholipids is between approximately 0.84-0.9. In an embodiment the molar ratio of cholesterol to phospholipids is between approximately 0.5-0.75. In an embodiment the molar ratio of cholesterol to phospholipids is between approximately 0.55-0.6.

3. Lipids, Proteins, and Carbohydrates

In an embodiment, approximately 52% of the membrane mass is protein, approximately 40% is lipid, and approximately 8% is carbohydrate. In an embodiment, approximately 7% of the carbohydrate content is comprised of glycosphingolipids and approximately 93% of the carbohydrate content is comprised of O-linked and N-linked oligosaccharides on membrane-associated polypeptides.

In an embodiment, the mass ratio of lipid to protein in the exosome is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In an embodiment, the mass ratio of lipid to carbohydrate in the exosome is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In an embodiment, the mass ratio of carbohydrate to protein in the exosome is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In an embodiment, the area occupancy of protein in the exosome is approximately 23% and the area occupancy of lipid in the exosome is approximately 77%.

Exosomes do not contain a random sampling of their producer cell's cytoplasm, but are enriched in specific mRNA, miRNA and proteins (Bobrie, et al., Traffic 12:1665-1668, 2011). Some exosomes express surface markers e.g., MHC-II, MHC-I, CD86 and ICAM-1. Some exosomes express molecules with biologic activity (such as Fas ligand, PD-1, MICA/B, mdr1, MMPs, CD44, and autoreactive antigens). This cargo is protected from degradation by proteases and RNases while the complex is in the interstitial space, and retains bioactivity once taken up by a recipient cell. In this way, exosomes facilitate the transfer of interactive signaling and enzymatic activities that would otherwise be restricted to individual cells based on gene expression (Lee, et al, Semin Immunopathol 33:455-467, 2011).

In an embodiment, the exosome comprises a polypeptide selected from the following list, including but not limited to, spectrin, myosin-like polypeptide, band 3, SLC4A1, actin, actin-like polypeptide, glyceraldehyde 3-P dehydrogenase (G3PD), tetraspanins, Alix and TSG101, integrins, selectins, CR1, TNFRI, proteolytic enzymes, glycosylphosphatidylinositol (GPI)-linked proteins or histones.

In an embodiment, the exosome comprises at least one polypeptide selected from Table 4.

In an embodiment, the exosome comprises at least one, two, three, four, five, six, or seven of the polypeptides selected from the following list, including but not limited to, spectrin, myosin-like polypeptide, band 3, SLC4A1, actin, actin-like polypeptide, glyceraldehyde 3-P dehydrogenase (G3PD), tetraspanins, Alix and TSG101, integrins, selectins, CR1, TNFRI, proteolytic enzymes, glycosylphosphatidylinositol (GPI)-linked proteins or histones.

Payloads

Exosomes can comprise payloads such as peptides, proteins, DNA, RNA, siRNA and other macromolecules (e.g., small therapeutic molecules). In some embodiments, the payload is transferred to a producer cell by applying controlled injury to the cell for a predetermined amount of time in order to cause perturbations in the cell membrane such that the payload can be delivered to the inside of the cell (e.g., the cytoplasm). In some embodiments the payload is transferred to an exosome isolated from a producer cell by applying controlled injury to the exosome for a predetermined amount of time in order to cause perturbations in the complex membrane such that the payload can be delivered to the inside of the exosome. In some embodiments the payload of the exosome can be loaded within the membrane or interior portion of the exosome.

The payload can be a therapeutic agent selected from a variety of known small molecule pharmaceuticals. Alternatively, the payload can be a therapeutic agent selected from a variety of macromolecules, such as, e.g., an inactivating peptide nucleic acid (PNA), an RNA or DNA oligonucleotide aptamer, an interfering RNA (iRNA), a peptide or a protein.

In some embodiments, the payload that can be delivered to a target by an exosome includes, but is not limited to, RNA, DNA, siRNA, mRNA, lncRNA, iRNA, polypeptides, enzymes, cytokines, antibodies, antibody fragments, small molecules, chemotherapeutics, metals, viral particles, imaging agents and plasmids.

In some embodiment, the exosome comprises a payload of siRNA capable of interfering with the expression of an oncogene or other dysregulating polypeptide. In some embodiments, the siRNA is capable of interfering with the expression of BCR-ABL, clusterin, survivin, B-catenin, CXCR4, BRCA-1 or BRCA-2.

In another embodiment, the exosome comprises a payload of antibodies, scFv, or nanobody that have intracellular targets including, but not limited to, tau, amyloid beta, WT1, LMP2, HPV E6 E7, MAGE A3, p53, NY-ESO-1, MelanA/MART1, Ras, gp100, proteinase 3, bcr-abl, tyrosinase, surviving, hTERT and ML-IAP.

In another embodiment, the exosome comprises a payload of proteins, antibodies, polypeptides, or mRNAs encoding a polypeptides that include IL-1, IL-2, insulin, erythropoietin, anti-TNFalpha, glucocerebrosidase, interferon beta 1a, interferon beta 1b, agalsidase beta, velaglucerase alfa, dornase alfa, alpha galactosidase A, idursulfase, adalimumab, etancercept, rituximab, infliximab, trastuzumab, bevacizumab, filgrastim and ranibizumab.

In another embodiment, the exosome comprises a payload of miRNA, including, but not limited to, let-7a, let-7b, let-7c, mir-34, miR-101, miR-215 or miR-16.

In another embodiment, the exosome comprises a payload of small molecules, including, but not limited to, doxorubicin, daunorubicin, docetaxel, irinotecan, taxanes, topoisomerase inhibitors, cyclophosphamide, *vinca* alkaloids, cisplatin, retinoids, nucleotide analogs and kinase inhibitors.

In some embodiments the payload of the exosome is a nucleic acid molecule, e.g., mRNA or DNA, and the exosome targets the payload to the cytoplasm of the recipient or target cell, such that the nucleic acid molecule can be translated (if mRNA) or transcribed and translated (if DNA) and thus produce the polypeptide encoded by the payload nucleic acid molecule within the target cell. In an embodiment, the polypeptide encoded by the payload nucleic acid molecule is secreted by the target cell, thus modulating the systemic concentration or amount of the polypeptide encoded by the payload nucleic acid molecule in the subject. In an embodiment, the polypeptide encoded by the payload nucleic acid molecule is not secreted by the target cell, thus modulating the intracellular concentration or amount of the polypeptide encoded by the payload nucleic acid molecule in the subject. In an embodiment, the polypeptide encoded by the payload nucleic acid molecule is toxic to the target cell or to other cell or tissue in the subject, e.g., toxic to a cancer cell. In an embodiment, the polypeptide encoded by the payload nucleic acid molecule is not toxic to the target cell or other cell or tissue in the subject, e.g., is therapeutically beneficial or corrects a disease phenotype.

The mRNA can be naked or modified, as desired. mRNA modification that improve mRNA stability and/or decrease immunogenicity include, e.g., ARCA: anti-reverse cap analog ($m_2^{7,3'-O}GP_3G$), $GP_3G$ (Unmethylated Cap Analog), $m^7GP_3G$ (Monomethylated Cap Analog), $m_3^{2.2.7}GP_3G$ (Trimethylated Cap Analog), m5CTP (5'-methyl-cytidine triphosphate), m6ATP (N6-methyl-adenosine-5'-triphosphate), s2UTP (2-thio-uridine triphosphate) and Ψ (pseudouridine triphosphate).

In some embodiments, the payload of the exosome is a miRNA or pre-miRNA molecule, and the exosome targets the payload to the cytoplasm of the target cell, such that the miRNA molecule can silence a native mRNA in the target cell. miRNAs are small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators. There are three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end. The cleavage product, the premature miRNA (pre-miRNA) is about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length. MicroRNAs function by engaging in base pairing (perfect or imperfect) with specific sequences in their target genes' messages (mRNA). The miRNA degrades or represses translation of the mRNA, causing the target genes' expression to be post-transcriptionally down-regulated, repressed, or silenced. In animals, miRNAs do not necessarily have perfect homologies to their target sites, and partial homologies lead to translational repression, whereas in plants, where miRNAs tend to show complete homologies to the target sites, degradation of the message (mRNA) prevails. MicroRNAs are widely distributed in the genome, dominate gene regulation, and actively participate in many physiological and pathological processes. For example, the regulatory modality of certain miRNAs is found to control cell proliferation, differentiation, and apoptosis; and abnormal miRNA profiles are associated with oncogenesis.

In an embodiment, the exosome comprises as a receiver synaptobrevin, as a payload an mRNA molecule encoding ricin toxin, and is useful for targeting the payload mRNA to tumor cells such that the mRNA is translated and the cells are killed.

In an embodiment, the exosome comprises as a receiver mannose, as a payload an mRNA molecule encoding glu-cocerebrosidase, and is useful for targeting the payload mRNA to macrophages in a subject with Gaucher's disease such that the mRNA is translated and the restorative enzyme is expressed, thus rescuing the recipient macrophage.

In some embodiments, the payload can be engineered for specific trafficking from the producer cell into the exosome. In some embodiments, the receiver or payload can be directed for trafficking by an addition of a molecule to the payload (e.g., conjugation or fusion of another molecule). In certain embodiments, the additional molecule can be appended via a linker. In certain embodiments, the payload can be directed for trafficking by modifying the payload composition (e.g., a nucleotide change for nucleic acid payloads or amino acid change for polypeptide payloads). In some embodiments a receiver can be directed for trafficking by modifying the payload sequence to share increased homology with part or all of a lipid listed in Table 3, or a nucleic acid listed in Table 7.

In some embodiments, a nucleic acid payload can be engineered for specific trafficking from the producer cell into the exosome. In certain embodiments, a nucleic acid payload (e.g., mRNA or miRNA) can comprise a sequence in the coding or noncoding region that targets the nucleic acid to the exosome. In certain embodiments, the noncoding region can include a 3' UTR or 5' UTR.

In some embodiments the payload of the exosome can be a membrane protein delivered to the plasma membrane or endosomal membrane of the recipient cell.

Exosomes can comprise two or more payloads, including mixtures, fusions, combinations and conjugates, of atoms, molecules, etc. as disclosed herein, for example including but not limited to, a nucleic acid combined with a polypep-tide; two or more polypeptides conjugated to each other; a protein conjugated to a biologically active molecule (which can be a small molecule such as a prodrug); and the like.

Suitable payloads include, without limitation, pharmaco-logically active drugs and genetically active molecules, including antineoplastic agents, anti-inflammatory agents, hormones or hormone antagonists, ion channel modifiers, and neuroactive agents. Examples of suitable payloads of therapeutic agents include those described in, "The Phar-macological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Elec-trolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antago-nists; Vitamins, Dermatology; and Toxicology, all incorpo-rated herein by reference. Suitable payloads further include toxins, and biological and chemical warfare agents, for example, see Somani, S. M. (ed.), Chemical Warfare Agents, Academic Press, New York (1992)).

In some embodiments, the payload is a therapeutic agent, such as a small molecule drug or a large molecule biologic. Large molecule biologics include, but are not limited to, a protein, polypeptide, or peptide, including, but not limited to, a structural protein, an enzyme, a cytokine (such as an interferon and/or an interleukin), a polyclonal or monoclonal antibody, or an effective part thereof, such as an Fv frag-ment, which antibody or part thereof, can be natural, syn-thetic or humanized, a peptide hormone, a receptor, or a signaling molecule.

Large molecule biologics are immunoglobulins, antibod-ies, Fv fragments, etc., that are capable of binding to antigens in an intracellular environment. These types of molecules are known as "intrabodies" or "intracellular anti-bodies." An "intracellular antibody" or an "intrabody" includes an antibody that is capable of binding to its target or cognate antigen within the environment of a cell, or in an environment that mimics an environment within the cell. Selection methods for directly identifying such "intrabod-ies" include the use of an in vivo two-hybrid system for selecting antibodies with the ability to bind to antigens inside mammalian cells. Such methods are described in PCT/GB00/00876, incorporated herein by reference. Tech-niques for producing intracellular antibodies, such as anti-β-galactosidase scFvs, have also been described in Mar-tineau et al., J Mol Biol 280:117-127 (1998) and Visintin et al., Proc. Natl. Acad. Sci. USA 96:11723-1728 (1999).

Large molecule biologics include but is not limited to, at least one of a protein, a polypeptide, a peptide, a nucleic acid, a virus, a virus-like particle, an amino acid, an amino acid analogue, a modified amino acid, a modified amino acid analogue, a steroid, a proteoglycan, a lipid and a carbohy-drate or a combination thereof (e.g., chromosomal material comprising both protein and DNA components or a pair or set of effectors, wherein one or more convert another to active form, for example catalytically).

A large molecule biologic can include a nucleic acid, including, but not limited to, an oligonucleotide or modified oligonucleotide, an antisense oligonucleotide or modified antisense oligonucleotide, an aptamer, a cDNA, genomic DNA, an artificial or natural chromosome (e.g., a yeast artificial chromosome) or a part thereof, RNA, including an siRNA, a shRNA, mRNA, tRNA, rRNA or a ribozyme, or a peptide nucleic acid (PNA); a virus or virus-like particles; a nucleotide or ribonucleotide or synthetic analogue thereof, which can be modified or unmodified.

The large molecule biologic can also be an amino acid or analogue thereof, which can be modified or unmodified or a non-peptide (e.g., steroid) hormone; a proteoglycan; a lipid; or a carbohydrate. If the large molecule biologic is a polypeptide, it can be loaded directly into a producer cell according to the methods described herein. Alternatively, an exogenous nucleic acid encoding a polypeptide, which sequence is operatively linked to transcriptional and trans-lational regulatory elements active in a producer cell at a target site, can be loaded.

Small molecules, including inorganic and organic chemi-cals, can also be used as payloads of the exosomes described herein.

In some embodiments, the small molecule is a pharma-ceutically active agent. Useful classes of pharmaceutically active agents include, but are not limited to, antibiotics, anti-inflammatory drugs, angiogenic or vasoactive agents, growth factors and chemotherapeutic (anti-neoplastic) agents (e.g., tumour suppressers).

If a prodrug is loaded into the exosome in an inactive form it is often useful that the exosome further comprises an activating polypeptide which converts the inactive prodrug to active drug form. In an embodiment, activating polypeptides include, but are not limited to, viral thymidine kinase (encoded by Genbank Accession No. J02224), carboxypeptidase A (encoded by Genbank Accession No. M27717), α-galactosidase (encoded by Genbank Accession No. M13571), β-glucuronidase (encoded by Genbank Accession No. M15182), alkaline phosphatase (encoded by Genbank Accession No. J03252 J03512), or cytochrome P-450 (encoded by Genbank Accession No. D00003 N00003), plasmin, carboxypeptidase G2, cytosine deaminase, glucose oxidase, xanthine oxidase, β-glucosidase, azoreductase, t-gutamyl transferase, β-lactamase and penicillin amidase.

Either the activating polypeptide or the exogenous gene encoding it can be transduced into a producer cell to generate a exosome. Both the prodrug and the activating polypeptide can be encoded by genes on the same exogenous nucleic acid. Furthermore, either the prodrug or the activating polypeptide of the prodrug can be transgenically expressed in a producer cell.

In an embodiment, the prodrug and/or the activating polypeptide of the prodrug are expressed in a target cell.

Imaging Agents

In certain embodiments, the exosomes are also be labeled with one or more positive markers that can be used to monitor over time the number or concentration of exosomes in vivo. Suitable fluorescent compounds include those that are approved by the Food & Drug Administration for human use including but not limited to fluorescein, indocyanin green, and rhodamine B. For example, producer cells or exosomes can be non-specifically labeled with fluorescein isothiocyanate (FITC; Bratosin et al., Cytometry 46:351-356 (2001)). For example, a solution of FITC-labeled lectins in phosphate buffered saline (PBS) with 0.2 mM phenylm-ethysulfonyl fluoride (PMSF) is added to an equal volume of producer cells or isolated exosomes in the same buffer. The cells or complexes are incubated with the FITC-labeled lectins for 1 h at 4° C. in the dark. The lectins bind to sialic acids and beta-galactosyl residues on the surface of the producer cells or exosomes.

Other dyes can be useful for tracking exosomes in vivo. A number of reagents can be used to non-specifically label an exosome. For example, producer cells or exosomes are optionally labeled with PKH26 Red (See, e.g., Bratosin, et al., (1997) Cytometry 30:269-274). Producer cells (e.g. $1-3 \times 10^7$ cells) are suspended in 1 ml of diluent and rapidly added to 1 ml or 2 μM PKH26 dissolved in the same diluent. The mixture is mixed by gentle pipetting and incubated at 25° C. for 2-5 min with constant stirring. The labeling can be stopped by adding an equal volume of human serum or compatible protein solution (e.g., 1% bovine serum albumin). After an additional minute, an equal volume of cell culture medium is added and the cells are isolated by centrifugation at 2000×g for 5 min. Cells or complexes are washed three times by repeated suspension in cell culture medium and centrifugation. PHK26-labeled exosomes can be monitored with a maximum excitation wavelength of 551 nm and a maximum emission wavelength of 567 nm.

Exosomes are optionally tracked in vivo using VivoTag 680 (VT680; VisEn Medical, Woburn, Mass., USA), a near-infrared fluorochrome with a peak excitation wavelength of 670±5 nm and a peak emission wavelength of 688±5 nm. VT680 also contains an amine reactive NHS ester which enables it to cross-link with proteins and peptides. The surface of producer cells or exosomes is optionally labeled with VT680 (See, e.g., Swirski, et al., (2007) PloS ONE 10:e1075). For example, $4 \times 10^6$ cells/ml are incubated with VT680 diluted in complete culture medium at a final concentration of 0.3 to 300 μg/ml for 30 min at 37° C. The cells are washed twice with complete culture medium after labeling. Cells or complexes can be non-specifically labeled based on proteins expressed on the surface of the producer cell or the exosome. Alternatively, a specific surface polypeptide (e.g., a receiver polypeptide) can be labeled with VT680. In some embodiments, a protein or peptide can be directly labeled with VT680 ex vivo and subsequently either attached to the surface of the cell or incorporated into the interior of the cell or complex using methods described herein. In vivo monitoring can, for example, be performed using the dorsal skin fold. Laser scanning microscopy can be performed using, for example, an Olympus IV 100 in which VT680 is excited with a red laser diode of 637 nm and detected with a 660/LP filter. Alternatively, multiphoton microscopy can be performed using, for example, a BioRad Radiance 2100 MP centered around an Olympus BX51 equipped with a 20×/0.95 NA objective lens and a pulsed Ti:Sapphire laser tuned to 820 nm. The latter wavelength is chosen because VT680 has a peak in its two-photon cross-section at 820 nm.

Alternatively or in addition, an exosome can be labeled with other red and/or near-infrared dyes including, for example, cyanine dyes such as Cy5, Cy5.5 and Cy7 (Amersham Biosciences, Piscataway, N.J., USA) and/or a variety of Alexa Fluor dyes including Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., USA). Additional suitable fluorophores include IRD41 and IRD700 (LI-COR, Lincoln, Nebr., USA), NIR-1 and 1C5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, Calif.). Quantum dots (Qdots) of various emission/excitation properties can also be used for labeling exosomes (See, e.g., Jaiswal et al., Nature Biotech. 21:47-51 (2003)). Many of these fluorophores are available from commercial sources either attached to primary or secondary antibodies or as amine-reactive succinimidyl or monosuccinimidyl esters, for example, ready for conjugation to a protein or proteins either on the surface or inside the exosome.

Magnetic nanoparticles are optionally used to track exosomes in vivo using high resolution MRI (Montet-Abou et al., Molecular Imaging 4:165-171 (2005)). Magnetic particles can be internalized by several mechanisms. Magnetic particles can be taken up by a producer cell or by an exosome through fluid-phase pinocytosis or phagocytosis. Alternatively, the magnetic particles can be modified to contain a surface agent such as, for example, a membrane translocating HIV TAT peptide which promotes internalization. In some instances, a magnetic nanoparticle such as, for example, Feridex IV®, an FDA approved magnetic resonance contrast reagent, are optionally internalized into a producer cell or exosome in conjunction with a transfection agent such as, for example, protamine sulfate (PRO), polylysine (PLL), and lipofectamine (LFA).

Surface Molecules or Markers

In some embodiments, the exosome comprises polypeptides on its surface selected from CD47, CD55, CD40, CD63, CD9, CD81, CD133 and CD59. In some embodiments, the exosome is modified to contain the one or more polypeptides. In some embodiments, the producer cell is modified to contain the one or more polypeptides. In some embodiments, the producer cell naturally contains the one or more polypeptides and exosomes derived therefrom also contain the polypeptides. The surface polypeptides can confer different functionalities to the exosome, e.g., specific targeting capabilities, delivery functions (e.g., fusion molecules), enzymatic functions, increased or decreased half-life in vivo, etc.

In some embodiments, the surface polypeptide can, e.g., stabilize the exosome, target the exosome to particular cells and tissues, engage the reticulo-endothelial system, protect the exosome from macrophages and other phagocytic cells, and/or evade other components of the innate immune system. Suitable polypeptides include, e.g., complement regulatory polypeptides, inhibitors of cell-mediated degradation (e.g., CD47, CD55, CD40, CD63, CD9, CD133 and CD59), and anti-inflammatory polypeptides. Alternatively or in addition, such polypeptides can shorten or control the half-life of the complex, including targeting to macrophages or other phagocytic cells. Suitable polypeptides can promote apoptosis or otherwise trigger opsonization.

For example, CD40 is a costimulatory protein found on antigen presenting cells and is required for their activation; CD63 is a cell surface glycoprotein that forms a complex with integrins; CD133 is thought to act as an organizer of cell membrane topology; and CD9 is a member of the transmembrane 4 superfamily, also known as the tetraspanin family that mediates signal transduction events.

As many drugs are systemically delivered to the blood circulatory system, the answer to the problem of effective drug delivery often focuses on maintaining the drug in the blood for extended periods of time. Thus, the development of long-circulating (long half-life) therapeutics that remain biologically available in the blood for extended time periods is an unmet need. The exosomes described herein can be modified to increase or decrease their half-life in circulation. In some embodiments, the half-life of the payload in circulation can be modified by altering the half-life of the exosome. In some instances, the half-life is increased and the increase can be, for instance from about 1.5-fold to 20-fold for a therapeutic agent payload maintained in the exosome when compared to a therapeutic agent not contained in the exosome and the half-life being measured in a serum-containing solution.

Residency of the exosome and/or the payload in the circulatory system, in certain embodiments, is determined by the presence or absence of certain polypeptides on the exosome. For example, the exosome can comprise a CD47, CD55, or CD59 polypeptide or a functional fragment thereof.

CD47 is a membrane protein that interacts with the myeloid inhibitory immunoreceptor SIRPα (also termed CD172a or SHPS-1) that is present, e.g., on macrophages. Engagement of SIRPα by CD47 provides a down-regulatory signal that inhibits host cell phagocytosis. For example, high levels of CD47 allow cancer cells to avoid phagocytosis despite the presence pro-phagocytic signals, such as high levels of calreticulin. CD47 also has further roles in cell adhesion, e.g., by acting as an adhesion receptor for THBS1 on producer cells and in the modulation of integrins. CD47 interaction with SIRPα further prevents maturation of immature dendritic cells, inhibits cytokine production by mature dendritic cells. CD47 interaction with SIRPγ mediates cell-cell adhesion, enhances superantigen-dependent T-cell-mediated proliferation and co-stimulates T-cell activation.

CD47 is a 50 kDa membrane receptor that has extracellular N-terminal IgV domain, five transmembrane domains, and a short C-terminal intracellular tail. There are four alternatively spliced isoforms of CD47 that differ only in the length of their cytoplasmic tail. In some embodiments, the exosome can comprise a CD47 or a functional fragment thereof comprising one or more of the extracellular N-terminal IgV domain, one, two, three, four, or five transmembrane domains, and/or the short C-terminal intracellular tail. The cytoplasmic tail can be found as four different splice isoforms ranging from 4 to 36 amino acids. The 16 amino acid form 2 is expressed in all cells of hematopoietic origin and in endothelial and epithelial cells. The 36 amino acid form 4 is expressed primarily in neurons, intestine, and testis. The 4 amino acid form 1 is found in epithelial and endothelial cells. The expression pattern of the 23 amino acid form 3 resembles that of form 4. In some embodiments, the exosome comprises CD47 or a functional fragment thereof that is of one of form 1, from 2, form 3, or from 4. In some embodiments, the exosome does not comprise form 2. In some embodiments, the exosome comprises a modified CD47, such as a conformational change. For example, a conformational change in CD47 is introduced so that the modified CD47 is capable of interacting with TSP-1. In an embodiment, the modified CD47 comprising the conformational change creates a different binding site for SIRPα. In some embodiments, the exosome comprises a modified CD47 polypeptide or a functional polypeptide fragment thereof comprising a conformational change. In certain embodiments, the exosome comprises a fusion of a CD47 isoform to the extracellular domain of a native producer cell polypeptide. For example, the N- or C-terminus of a native polypeptide of a producer cell can be fused to the CD47 polypeptide or functional fragment thereof, which can lead to a reduction of the SIRPα-mediated signal to macrophages to phagocytose the exosome.

In some embodiments, the producer cells naturally express CD47. In some embodiments, the natural levels of CD47 are altered in the producer cell, e.g., by overexpression or inhibition of CD47 expression using any suitable method, such as the introduction of exogenous nucleic acids (e.g., expression vectors, CD47 mRNA, CD47 siRNA and the like).

For example, exosomes that are administered to a subject can comprise elevated CD47 levels when compared to native levels of a suitable control. Elevated CD47 levels can be achieved, e.g., by exogenous expression by the producer cell line of CD47 from an exogenous nucleic acid, by loading of CD47 mRNA into the producer cell or directly into the exosome, or by conjugating CD47 polypeptide to the surface of the producer cell or directly to the surface of the exosome. Elevated CD47 levels are useful to increase the half-life of the population of exosomes in the circulatory system of the subject. The exosomes comprise a payload (such as a therapeutic agent) and optionally a receiver and increasing the half-life of the exosome can increase the half-life of the payload in circulation. This potentially increases the therapeutic window in which payload is active. In one instance, a population of $10^{11}$ exosomes comprises an adenosine deaminase payload and an exogenous CD47 polypeptide on its surface. When administered to a subject with an enzyme deficiency, such as ADA-SCID, the half-life of the exosome is extended beyond that of a complex not comprising exogenous CD47 polypeptide and the subject requires less frequent dosing. Half-life extension is a particular advantage when compared to current enzyme therapies not involving exosomes.

In some embodiments, CD47 is altered by heparin and/or chondroitin sulfate glycosaminoglycan (GAG) chains. In some embodiments, the exosome comprises CD47 as a proteoglycan. In some embodiments, the exosome comprises a CD47 proteoglycan that is conjugated to the complex. In an embodiment, the CD47 proteoglycan comprises heparin and/or chondroitin sulfate glycosaminoglycan (GAG) chains. In an embodiment, that CD47 proteoglycan has a size of greater than 150 kDa, 200 kDa or greater than 250 kDa. In an embodiment, CD47 comprises one or more GAG chains at Ser64.

In some embodiments, the residency of an exosome generated using producer cells can be further modulated by changing the amount or number of oxidized lipids on the membrane of the exosome. In an embodiment, the exosome comprises oxidized lipids in an amount effective to shorten its half-life. In some embodiments, the amount of oxidized lipids in the membrane are altered such that mobility of CD47 is increased or decreased, thereby aiding or hindering, respectively the ability of CD47 to cluster on the membrane. (See, Olsson, Department of Integrative Medical Biology, Section for Histology and Cell Biology, Umea University, Umea, Sweden, 2008).

CD55, also known as complement decay-accelerating factor or DAF, is a 70 kDa membrane protein. CD55 recognizes C4b and C3b fragments of the complement system that are created during C4 (classical complement pathway and lectin pathway) and C3 (alternate complement pathway) activation. It is thought that interaction of CD55 with cell-associated C4b and C3b proteins interferes with their ability to catalyze the conversion of C2 and factor B to active C2a and Bb and thereby prevents the formation of C4b2a and C3bBb, the amplification convertases of the complement cascade. CD55 is thought to block the formation of membrane attack complexes. CD55 can prevent lysis by the complement cascade. In some embodiments, the exosome comprises CD55 polypeptide or a functional polypeptide fragment thereof. In some embodiments, the exosome comprises an exogenous CD55 polypeptide and an exogenous CD47 polypeptide or functional polypeptide fragments thereof.

CD59 glycoprotein also known as MAC-inhibitory protein (MAC-IP), membrane inhibitor of reactive lysis (MIRL), protectin, or HRF is a protein that attaches to host cells via a glycophosphatidylinositol (GPI) anchor. When complement activation leads to deposition of C5b678 on host cells, CD59 can prevent C9 from polymerizing and forming the complement membrane attack complex. CD59 can prevent lysis by the complement cascade. In some embodiments, the exosome comprises CD59 polypeptide or a functional polypeptide fragment thereof. In some embodiments, the exosome comprises an exogenous CD59 polypeptide and an exogenous CD47 polypeptide or functional polypeptide fragments thereof.

In some embodiments, the exosome comprises one or more of an exogenous CD55 polypeptide, an exogenous CD59 polypeptide and/or an exogenous CD47 polypeptide or functional polypeptide fragments thereof in a desired amount, copy number and/or ratio sufficient to regulate the residency of the exosome in circulation.

Effective amounts of CD47, CD55, and CD59 include $10^2$, $10^3$, $10^4$, $10^5$, $10^6$, $10^7$, $10^9$ polypeptides per exosome. Alternatively, an effective amount is the amount capable of extending the exosome's half-life by 10%, 20%, 30%, 40%, 50%, 60%, 70%, 80%, 90%, 100%, 200%, 400%, 800%, 1,000%, or 10,000% relative to the half-life that the exosome would exhibit without the polypeptides.

Receivers

Optionally, the exosome comprises a receiver. In some embodiments, a receiver polypeptide comprises or consists essentially of a polypeptide. In some embodiments, a receiver comprises or consists essentially of a carbohydrate, a nucleic acid, a lipid, a small molecule or a combination thereof. In some embodiments, the receiver is synthetic. For example, the receiver is an exogenous polypeptide or molecule or is expressed from an exogenous nucleic acid.

In some embodiments, the receiver functions to "target", e.g., aggregate around, concentrate itself in, home to, undergo a transformation near, or otherwise engage a target molecule, cell or tissue of interest. In some embodiments, a receiver is capable of interacting with a target, e.g., to associate with, bind to, or fuse with a target, such as a target cell in sufficient proximity and for a sufficient duration for the exosome to bring about delivery of the payload to the target.

In some embodiments, the interaction of the receiver with a target comprises altering an activity of the target. In some embodiments, the interaction of the receiver with a target comprises altering the composition of the target. In some embodiments, the interaction of the complex with a target comprises reducing an activity of the target. In some embodiments, the interaction of the complex with a target comprises inactivating the target.

In some embodiments, the interaction of the receiver with a target comprises altering the RNA composition of the target. In some embodiments, the interaction of the complex with a target comprises inducing translation in the target of a payload RNA.

In some embodiments, receivers comprise polypeptides. Receiver polypeptides can range in size from 6 amino acids to 3000 amino acids and can exceed 6, 10, 15, 20, 25, 30, 35, 40, 50, 60, 70, 80, 90, 100, 150, 200, 300, 400 or can exceed 500 amino acids. Receiver polypeptides can range in size from about 20 amino acids to about 500 amino acids, from about 30 amino acids to about 500 amino acids or from about 40 amino acids to about 500 amino acids.

In some embodiments, the receiver polypeptide comprises a chimeric or fusion protein which can comprise two or more distinct protein domains. These chimeric receivers are heterologous or exogenous in the sense that the various domains are derived from different sources, and as such, are not found together in nature and can be encoded e.g., by exogenous nucleic acids. Receiver polypeptides can be produced by a number of methods, many of which are well known in the art and also described herein. For example, receiver polypeptides can be obtained by extraction (e.g., from isolated cells), by expression of an exogenous nucleic acid encoding the receiver polypeptide, or by chemical synthesis. Receiver polypeptides can be produced by, for example, recombinant technology, and expression vectors encoding the polypeptide introduced into host cells (e.g., by transformation or transfection) for expression of the encoded receiver polypeptide.

There are a variety of conservative changes that can generally be made to an amino acid sequence without altering activity. These changes are termed conservative substitutions or mutations; that is, an amino acid belonging to a grouping of amino acids having a particular size, charge or other characteristic can be substituted for another amino acid. Substitutions for an amino acid sequence can be selected from other members of the class to which the amino acid belongs. For example, the nonpolar (hydrophobic) amino acids include alanine, leucine, isoleucine, valine, proline, phenylalanine, tryptophan, methionine, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Conservative substitutions also include substituting optical isomers of the sequences for other optical isomers, specifically D amino acids for L amino acids for one or more residues of a sequence. Moreover, all of the amino acids in a sequence can undergo a D to L isomer substitution. Exemplary conservative substitutions include, but are not limited to, Lys for Arg and vice versa to maintain a positive charge; Glu for Asp and vice versa to maintain a negative charge; Ser for Thr so that a free ~OH is maintained; and Gln for Asn to maintain a free $NH_2$. Moreover, point mutations, deletions, and insertions of the polypeptide sequences or corresponding nucleic acid sequences can in some cases be made without a loss of function of the polypeptide or nucleic acid fragment. Substitutions can include, e.g., 1, 2, 3, or more residues. Any teaching of a specific amino acid sequence or an exogenous nucleic acid encoding the polypeptide or teaching of the name of the name thereof includes any conservative substitution point mutations, deletions, and insertions of those polypeptide sequences or corresponding nucleic acid sequences and any sequence deposited for the protein or gene in a database that can be made without a loss of function of the polypeptide or nucleic acid fragment.

Any of the methods described herein can be used to generate any of the polypeptides described herein (e.g., therapeutic polypeptides and surface or maker polypeptides) and application of these methods is not restricted to receiver polypeptides.

In some embodiments, the receiver polypeptide is associated with the membrane of the exosome. In other embodiments, the receiver polypeptide is not associated with the membrane of the exosome.

In an embodiment, the receiver comprises a polypeptide that comprises an amino acid sequence derived from an antibody. The antibody receiver can be expressed as a full-length protein or a fragment thereof. In an embodiment, the receiver comprises an antibody amino acid sequence that is specific for a desired target. In some embodiments, the antibody is a scFv. In other embodiments, the antibody is a nanobody.

In an embodiment, the receiver comprises a polypeptide that comprises an amino acid sequence derived from a scFv antibody. The scFv antibody receiver can be expressed as a full-length protein or a fragment thereof. The scFv antibody can be expressed as a fusion protein. Suitable scFv receiver polypeptides include, but are not limited to, those listed in Table 5.

The production of scFvs is known in the art. The scFv receiver can be made specific to any target molecule including, but not limited to, those in Table 6.

In certain embodiments, the receiver comprises a camelid-derived nanobody. Nanobodies are usually 12-15 kDa. They are considerably smaller than antibodies and scFv. Nanobodies can thus be easier to transfect, and the nanobody receiver will be more easily expressed, translated and or transported to the cell surface in a producer cell and ultimately the exosome derived therefrom. In certain embodiments, nanobody receivers are employed to minimize immunogenic effects caused by a specific receiver. Nanobodies because of their small size will offer reduced immunogenic potential. In certain embodiments, receiver nanobodies are employed because they have an increased ability to recognize hidden or uncommon epitopes compared to standard antibodies. For example, they can bind to small enzymatic cavities of a target and modulate the molecular behavior of the target.

In some embodiments, receivers comprise a protein-binding partner or a receptor on the surface of the exosome, which functions to target the exosome to a specific tissue space or to interact with a specific moiety on a target cell, either in vivo or in vitro. Suitable protein-binding partners include antibodies and functional fragments thereof, scaffold proteins, or peptides.

In some embodiments, the receiver is a molecule that promotes endocytosis in the target cell, e.g., by engaging receptors that stimulate receptor-mediated endocytosis. Suitable receivers for this purpose include, but are not limited to, transferrin, insulin, growth factors, epidermal growth factor, ligands for receptor tyrosine kinases, mannose, somatostatin, hormones and ligands of scavenger receptors.

In some embodiments, the receiver can be a molecule that promotes exosome fusion to the target cell, e.g., the target cell plasma membrane, the endosomal membrane or the lysosomal membrane, thus transferring the payload to the cytoplasm of the target cell. In some embodiments, the receiver is a coat protein, e.g., clathrin, coat protein complex (COP) 1, COP2; or a soluble N-ethylmaleimide-sensitive factor attachment protein receptor (SNARE), e.g., synaptobrevin, syntaxin, Tlg1p, SNAP-25, Vam3p, Vam7p; or a membrane fusion protein, e.g., a bacterial membrane fusion protein, a dynamin, DynA of *Bacillus subtilis*, HlyD; or a cell-penetrating polypeptide, e.g., a microbial pore forming protein, a poly-arginine polypeptide, an anti-microbial peptide, a microbial exotoxin or a microbial endotoxin.

In other embodiments, the receiver that promotes membrane fusion is an adhesion molecule (e.g., ICAM1), integrins (e.g., beta1 and beta2 integrins), tetraspanins (e.g., transferrin), phosphatidylserine or MFGE.

In some embodiments, the receiver mediates tissue targeting of the exosome. In some embodiments, the receiver mediates extravasation, intravasation or tissue penetration of the exosome. In certain embodiments, the receiver that mediates tissue targeting is a small peptide. In other embodiments, the receiver mediates tissue or cell penetration of the exosome.

In some embodiments, the receiver is a targeting molecule. In certain embodiments the targeting molecule can be an aptamer, a scFV, an antibody, a nanobody, a homing peptide, a folic acid, a cyclodextrin, a transferrin, a luteinizing hormone-releasing hormone or a glycoprotein.

In some embodiments, the receiver mediates exosome chemotaxis. In this aspect, the exosome is able to migrate to target tissue in response to cytokine or chemokine gradients.

In some embodiments, the receiver mediates angiogenesis. In some embodiments, angiogenesis mediated by the receiver enables improved tissue distribution or Pharmacokinetics of the exosome.

Targets

A suitable receiver can be chosen to interact with a specific target. Suitable targets include entities that are associated with a specific disease, disorder or condition. However, targets can also be chosen independent of a specific disease, disorder or condition.

In certain embodiments, suitable targets include, but are not limited to, those listed in Table 6.

In certain embodiments, the target is associated with a specific disease, disorder or condition such as those listed in Table 8 and Table 9.

In some embodiments, the exosome does not comprise a receiver and the exosome is capable of interacting with a target in the absence of a receiver.

In some embodiments, the target is a bacterium, for example *Enterococcus, Streptococcus,* or Mycobacteria, *Rickettsia, Mycoplasma, Neisseria meningitides, Neisseria gonorrheoeae, Legionella, Vibrio cholerae, Streptococci, Staphylococcus aureus, Staphylococcus epidermidis, Pseudomonas aeruginosa, Corynobacteria diphtheriae, Clostridium* spp., enterotoxigenic *Escherichia coli,* and *Bacillus anthracis.* Other pathogens for which bacteremia has been reported at some level include the following: *Rickettsia, Bartonella henselae, Bartonella quintana, Coxiella bumetii, chlamydia, Mycobacterium leprae, Salmonella; shigella; Yersinia enterocolitica; Yersinia pseudotuberculosis; Legionella pneumophila; Mycobacterium tuberculosis; Listeria monocytogenes; Mycoplasma* spp.; *Pseudomonas fluorescens; Vibrio cholerae; Haemophilus influenzae; Bacillus anthracis; Treponema pallidum; Leptospira; Borrelia; Corynebacterium diphtheriae; Francisella; Brucella melitensis; Campylobacter jejuni; Enterobacter; Proteus mirabilis; Proteus*; and *Klebsiella pneumoniae.*

In some embodiments, the target is a virus, including but limited to, those whose infection involves injection of genetic materials into host cells upon binding to cell surface receptors, viruses whose infection is mediated by cell surface receptors. Non-limiting examples of these viruses can be selected from Paramyxoviridae (e.g., pneumovirus, morbillivirus, metapneumovirus, respirovirus or rubulavirus), Adenoviridae (e.g., adenovirus), Arenaviridae (e.g., arenavirus such as lymphocytic choriomeningitis virus), Arteriviridae (e.g., porcine respiratory and reproductive syndrome virus or equine arteritis virus), Bunyaviridae (e.g., phlebovirus or hantavirus), Caliciviridae (e.g., Norwalk virus), Coronaviridae (e.g., coronavirus ortorovirus), Filoviridae (e.g., Ebola-like viruses), Flaviviridae (e.g., hepacivirus or flavivirus), Herpesviridae (e.g., simplexvirus, varicellovirus, cytomegalovirus, roseolovirus, or lymphocryptovirus), Orthomyxoviridae (e.g., influenza virus or thogotovirus), Parvoviridae (e.g., parvovirus), Picomaviridae (e.g., enterovirus or hepatovirus), Poxviridae (e.g., orthopoxvirus, avipoxvirus, or leporipoxvirus), Retroviridae (e.g., lentivirus or spumavirus), Reoviridae (e.g., rotavirus), Rhabdoviridae (e.g., lyssavirus, novirhabdovirus, or vesiculovirus), and Togaviridae (e.g., alphavirus or rubivirus). Specific examples of these viruses include human respiratory coronavirus, influenza viruses A-C, hepatitis viruses A to G and herpes simplex viruses 1-9.

In some embodiments, the target is a parasite, including but not limited to, for example, intestinal or blood-borne parasites, protozoa, trypanosomes; haemoprotozoa and parasites capable of causing malaria; enteric and systemic cestodes including taeniid cestodes; enteric coccidians; enteric flagellate protozoa; filarial nematodes; gastrointestinal and systemic nematodes and hookworms.

In some embodiments, the target is a fungus, including but not limited to, for example, *Candida albicans, Candida glabrata, Aspergillus, T. glabrata, Candida tropicalis, C. krusei* and *C. parapsilosis.*

In some embodiments, the target is a lipid, lipid complex or proteolipid complex.

In some embodiments, the target is a LFA (e.g., lymphocyte function-associated antigen 1), intercellular adhesion molecules (e.g., ICAM1), extracellular matrix proteins (e.g., fibronectin), phosphatidylserine receptors (e.g., T cell immunoglobulin domain, mucin domain proteins, TIM1/TIM4), lactaherin or integrins (e.g., avb3 or avb5).

In some embodiments, the target is an inflammatory molecule, a cytokine or a chemokine.

In some embodiments, the target is a carbohydrate, polysaccharide or amino acid.

In some embodiments, the target is a virus, a viral antigen, an envelope antigen or a capsid antigen.

In some embodiments, the target is a bacterium, a bacterial antigen, a bacterial surface antigen, a secreted bacterial toxin or a secreted bacterial antigen.

In some embodiments, the target is a fungus, a fungal antigen, a fungal cell surface antigen, a secreted fungal toxin or a secreted fungal antigen.

In some embodiments, the target is DNA or RNA.

In some embodiments, the target is a circulating cell, an inflammatory cell, a tumor cell or a metastatic cancer cell.

In some embodiments, the target is a mammalian cell, including but not limited to, for example, a human cell, a circulating cell, an immune cell, a neutrophil, an eosinophil, a basophil, a lymphocyte, a monocyte, a B cell, a T cell, a CD4+ T cell, a CD8+ T cell, a gamma-delta T cell, a regulatory T cell, a natural killer cell, a natural killer T cell, a macrophage, a Kupffer cell, a dendritic cell, a cancer cell, a cancer stem cell, a circulating tumor cell, a cancer cell from one of the following cancers including, but not limited to, ACUTE lymphoblastic leukemia (ALL), ACUTE myeloid leukemia (AML), anal cancer, bile duct cancer, bladder cancer, bone cancer, bowel cancer, brain tumours, breast cancer, cancer of unknown primary, cancer spread to bone, cancer spread to brain, cancer spread to liver, cancer spread to lung, carcinoid, cervical cancer, choriocarcinoma, chronic lymphocytic leukemia (CLL), chronic myeloid leukemia (CML), colon cancer, colorectal cancer, endometrial cancer, eye cancer, gallbladder cancer, gastric cancer, gestational trophoblastic tumours (GTT), hairy cell leukemia, head and neck cancer, Hodgkin lymphoma, kidney cancer, laryngeal cancer, leukemia, liver cancer, lung cancer, lymphoma, melanoma skin cancer, mesothelioma, men's cancer, molar pregnancy, mouth and oropharyngeal cancer, myeloma, nasal and sinus cancers, nasopharyngeal cancer, non-Hodgkin's lymphoma (NHL), oesophageal cancer, ovarian cancer, pancreatic cancer, penile cancer, prostate cancer, rare cancers, rectal cancer, salivary gland cancer, secondary cancers, skin cancer (non melanoma), soft tissue sarcoma, stomach cancer, testicular cancer, thyroid cancer, unknown primary cancer, uterine cancer, vaginal cancer and vulval cancer.

In some embodiments, the target is a non-circulating cell or tissue. In some embodiments, the target is a specific tissue including, but not limited to, endothelial tissues, connective tissues, muscle tissue, nervous tissue, and epithelial tissue. In some embodiments, the target is a specific organ systems based on an affinity for ligands associated with the tissues therein, including, but not limited to, the brain, liver, kidneys, gastrointestinal system, pancreas, spleen and lungs.

Pharmaceutical Compositions of the Invention

Aspects of the invention relate to use of preparations of exosomes for use as a medicament. In some embodiments, the exosomes are formulated for intravenous administration to the circulatory system of a mammalian subject. The methods of the invention include administering a therapeutically effective amount of exosomes. The exosomes of the invention can be formulated in pharmaceutical compositions. In some embodiments, the exosomes are formulated for intravenous administration to the circulatory system of a mammalian subject. The pharmaceutical compositions can comprise, in addition to one or more of the exosomes, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g., oral, intravenous, cutaneous or subcutaneous, nasal, intramuscular, intrathecal or intraperitoneal routes.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as manitol, sorbitol, sodium chloride can be added to the composition. Prolonged absorption of the injectable compositions can be brought about by including in the composition a compound which delays absorption, e.g., aluminum monostearate and gelatin.

Sterile injectable solutions can be prepared by incorporating the exosomes in an effective amount and in an appropriate solvent with one or a combination of ingredients enumerated herein, as desired. Generally, dispersions are prepared by incorporating the exosomes into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. In certain embodiments, exosomes are administered in the form of a depot injection or implant preparation which can be formulated in such a manner to permit a sustained or pulsatile release of the exosomes.

Systemic administration of compositions comprising exosomes can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the modified exosomes are formulated into ointments, salves, gels, or creams as generally known in the art.

The exosomes can also be prepared as pharmaceutical compositions in the form of suppositories (e.g., with conventional suppository bases such as cocoa butter and other glycerides) or retention enemas for rectal delivery.

In an embodiment, the pharmaceutical composition comprising exosomes is administered intravenously into a subject that would benefit from the pharmaceutical composition. In other embodiments, the composition is administered to the lymphatic system, e.g., by intralymphatic injection or by intranodal injection (See e.g., Senti et al., 2008 PNAS 105(46):17908), or by intramuscular injection, by subcutaneous administration, by direct injection into the thymus or into the liver.

In an embodiment, the pharmaceutical composition comprises exosomes and is administered as a liquid suspension. In an embodiment, the pharmaceutical composition is administered as a formulation that is capable of forming a depot following administration, and in a preferred embodiment, exosomes are slowly released into circulation or remain in depot form.

Typically, pharmaceutically acceptable compositions are highly purified to be free of contaminants, are biocompatible and not toxic, and are suited to administration to a subject. If water is a constituent of the carrier, the water is highly purified and processed to be free of contaminants, e.g., endotoxins.

The pharmaceutically acceptable carrier can be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate and/or mineral oil, but is not limited thereto. The pharmaceutical composition can further include a lubricant, a wetting agent, a sweetener, a flavor enhancer, an emulsifying agent, a suspension agent and/or a preservative.

The pharmaceutical compositions described herein comprise an exosome and optionally a pharmaceutically active or therapeutic agent. The therapeutic agent can be a biological agent, a small molecule agent, or a nucleic acid agent.

Dosage forms are provided that comprise a pharmaceutical composition comprising an exosome described herein. In some embodiments, the dosage form is formulated as a liquid suspension for intravenous injection.

Medical devices are provided that comprise a container holding a pharmaceutical composition comprising an exosome described herein and an applicator for intravenous injection of the pharmaceutical composition to a subject.

Medical kits are provided that comprise a pharmaceutical composition comprising an exosome described herein and a medical device for intravenous injection of the pharmaceutical composition to a subject.

In an embodiment, pharmaceutically acceptable suspensions of exosomes are packaged in a volume of approximately 1 ml to approximately 500 ml. In an embodiment, the packaging is a syringe or an IV bag suitable for transfusions. Administration of the suspension is carried out, e.g., by intravenous or intra-arterial injection, optionally using a drip from an IV bag or the like. The administration is typically carried out intravenously in the arm or via a central catheter. For administrations exceeding 50 ml, use of a drip is preferred.

In certain embodiments, pharmaceutical compositions for oral administration are in tablet, capsule, powder or liquid form. In certain embodiments, a tablet includes a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

In some embodiments, the pharmaceutical composition comprises one or more therapeutic agents and the exosomes described herein. In some embodiments, the exosomes are co-administered with of one or more separate therapeutic agents, wherein co-administration includes administration of the separate therapeutic agent before, after or concurrent with administration of the exosome.

In certain embodiments, supplementary therapeutic agents are incorporated into the compositions.

The pharmaceutically useful compound according to the present invention that is to be given to an individual, administration is preferably in a "therapeutically effective amount" or "prophylactically effective amount" (as the case can be, although prophylaxis can be considered therapy), this being sufficient to show benefit to the individual. The dosages of the exosomes, therapeutic exosomes and non-therapeutic exosomes are any dose that yields therapeutic benefit in the subject. The actual amount administered, and rate and time-course of administration, will depend on the nature and severity of the condition being treated. Prescription of treatment, e.g., decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

In certain embodiments, the dosages of either the non-therapeutic exosomes, therapeutic exosomes or both the non-therapeutic exosomes and therapeutic exosomes is between Ing to 10 ng, 10 ng to 100 ng, 100 ng to 1.0 µg, 1 µg to 5 µg, 5 µg to 10 µg, 10 µg-50 µg, 50 µg to 75 µg, 75 µg to 100 µg, 100 µg to 150 µg, 150 µg to 200 µg, 200 µg to 300 µg, 300 µg to 500 µg, 500 µg to 1 mg, or 1 mg to 10 mg.

In certain embodiments, the dosage of the non-therapeutic exosome is greater than the dosage of the therapeutic exosomes. In certain embodiments, the dosage of the non-therapeutic exosome is the same as the therapeutic exosomes. In some embodiments, the dosage of the non-therapeutic exosome is between 1.1-fold to 1.5-fold, 1.0-fold to 2.0-fold, 2.0-fold to 3.0-fold, 3.0-fold to 4.0-fold, 4.0-fold to 5.0-fold, 5.0-fold to 10.0-fold, 10.0-fold to 20.0-fold, 10.0-fold to 100-fold or 100-fold to 1,000-fold greater than the dosage of the therapeutic exosomes. In certain embodiments, the dosage of the non-therapeutic exosome is less than the dosage of the therapeutic exosome. In certain embodiments, the dosage of the non-therapeutic exosomes is between 1.1-fold to 1.5-fold, 1.0-fold to 2.0-fold, 2.0-fold to 3.0-fold, 3.0-fold to 4.0-fold, 4.0-fold to 5.0-fold, 5.0-fold to 10.0-fold, 10.0-fold to 20.0-fold, 10.0-fold to 100-fold or 100-fold to 1,000-fold less than the dosage of the therapeutic exosomes.

A composition can be administered alone or in combination with other treatments, either simultaneously or sequentially dependent upon the condition to be treated.

Methods of Making Exosomes

Provided herein are methods for producing isolated exosomes and pharmaceutical preparations thereof.

In some embodiments, the methods comprise: a) providing a producer cell capable of generating an exosome, b) obtaining from the producer cell the exosome, c) modifying the exosome with a payload, and d) isolating the modified exosome.

In some embodiments, the methods comprise: a) providing a producer cell capable of generating an exosome, b) modifying the producer cell with a payload, c) obtaining from the producer cell the exosomes, and d) isolating the modified exosomes.

Optionally, the isolated exosomes can be formulated into a pharmaceutical composition described herein. If desired, the activity of the pharmaceutical composition is tested or analyzed. Testing can include one or more of: i) analyzing the presence or activity of the payload, ii) analyzing the potency of the exosome in a phenotypic or functional assay iii) detecting the presence or absence of one or more biomarkers from the producer cell, iv) analyzing the size distribution of the exosomes, and/or v) analyzing the membrane composition of the exosomes.

If desired, the producer cell can be modified to comprise a receiver. Alternatively or in addition, the exosome is modified to comprise a receiver.

In some embodiments, the exosomes are released by the producer cells into a culture medium. The exosomes can be generated through a variety of cellular mechanisms including the endosomal sorting complexes required for transport I and II (ESCRT I and II), alternate endosome production pathways derived thereof, or mechanistic perturbation or disruption of the producer cell membrane, such as microfluidic compression or lysis, exposure to chemical stresses such as pH or apoptosis.

In some embodiments, the producer cell is a mammalian cell that is isolated or derived from a mammalian cell line. The exosomes can be derived from various cell lines, including eukaryotes, prokaryotes, archae, fungi and protists.

In some embodiments, generating an exosome comprises using isolated optionally cultured producer cells that are autologous and/or allogeneic to the subject in which the exosome is administered.

The producer cell can be cultured. Cultured producer cells can be scaled up from bench-top scale to bioreactor scale. For example, the producer cells are cultured until they reach saturation density, e.g., $1\times10^5$, $1\times10^6$, $1\times10^7$ or greater than $1\times10^7$ per ml. Optionally, upon reaching saturation density, the producer cells can be transferred to a larger volume of fresh medium. The producer cells can be cultured in a bioreactor, such as, e.g., a Wave-type bioreactor, a stirred-tank bioreactor. Various configurations of bioreactors are known in the art and a suitable configuration can be chosen as desired. Configurations suitable for culturing and/or expanding populations of producer cells can easily be determined by one of skill in the art without undue experimentation. The bioreactor can be oxygenated. The bioreactor can optionally contain one or more impellers, a recycle stream, a media inlet stream, and control components to regulate the influx of media and nutrients or to regulate the outflux of media, nutrients, and waste products.

In some embodiments, the bioreactor is a Wave bioreactor or a impeller-driven agitator. The bioreactor can be aerated by means of a sparger. In an embodiment, the bioreactor is disposable. In an embodiment, the bioreactor is CIP (cleaned in place). The final number of producer cells that can be obtained in a bioreactor setting as described herein can be greater than $10^9$, $10^{10}$, $10^{11}$, $10^{12}$, $10^{13}$ or greater than $10^{13}$ cells. The density of producer cells can be monitored during culture by measuring cell density by hemacytometer counting or by optical density reading at 600 nm. Optionally, the culture process is monitored for pH levels, oxygenation, agitation rate and/or recycle rate.

In some embodiments, the producer cells can be treated with chemicals, hormones, metabolites, nucleic acids, proteins, enzymes, lipids, nutrients, micronutrients or any other molecule to affect the cell's phenotype or profile of exosomes.

In some embodiments, the producer cells can be treated with a molecule, e.g., a DNA molecule, an RNA molecule, a mRNA, an siRNA, a microRNA, a lncRNA, a shRNA, a hormone or a small molecule, that activates or inhibits expression of one or more genes.

Producer cell inputs, including but not limited to, nutrients, micronutrients, metabolites, amino acids, sugars, and fatty acids can be increased or decreased. For example, producer cells can be grown in hypoxic conditions prior to and during isolation of exosomes.

The producer cells can be treated with physical stimuli, including but not limited to, irradiation, pressure, shear stress, mixing, turbulence, and shaking.

In an embodiment, the producer cell is differentiated from a starter or precursor cell. In this embodiment, the differentiation state of the producer cell is assessed by an in vitro assay. Suitable in vitro assays include measuring the number of cells, protein content or expression level, e.g., of a biomarker (e.g., differentiation marker), mRNA content or expression level, e.g., of a biomarker (e.g., a differentiation marker), lipid content, partition of a substrate, catalytic activity, or metabolic activity.

In some embodiments, the producer cells are cultured and the differentiation state of the cells and/or resulting exosomes is assessed at multiple time points over the course of the culture process.

In certain embodiments, a producer cell expresses (naturally or upon modification) a polypeptide (e.g., a receiver polypeptide, a therapeutic polypeptide and/or a surface marker polypeptide). In some embodiments, exosomes derived from the producer cells comprise the polypeptide that is expressed by the producer cell. The polypeptide can be exhibited on the surface of the exosome or can reside within the interior space of the exosome.

In certain embodiments, the polypeptide (e.g., a receiver polypeptide, a therapeutic polypeptide and/or a surface marker polypeptide) is conjugated to the producer cell or the exosome. The polypeptide usually is conjugated to the surface of the producer cell or exosome. Conjugation can be achieved chemically or enzymatically, by methods known in the art.

In certain embodiments, the polypeptide (e.g. a receiver polypeptide, a therapeutic polypeptide and/or a surface marker polypeptide) is loaded into the producer cell or exosome. In some embodiments, the polypeptide is not loaded into or onto the producer cell or exosome.

In some embodiments, the exosome comprises a polypeptide (e.g. a receiver polypeptide, a therapeutic polypeptide and/or a surface marker polypeptide) that is optionally i) expressed in the producer cell from an exogenous nucleic acid, ii) conjugated to the producer cell or the exosome, iii) loaded into or onto the producer cell or the exosome, and any combination of i), ii) and iii).

A non-polypeptide payload (e.g., a nucleic acid, such as an RNA, e.g., siRNA, miRNA, shRNA, etc., a therapeutic small molecule or a toxin) can be i) expressed in the producer cell from an exogenous nucleic acid, ii) conjugated to the producer cell or the exosome, iii) loaded into or onto the producer cell or the exosome, and any combination of i), ii) and iii), as applicable for the respective payload.

In some embodiments, the exosome is generated by contacting a suitable producer cell with an exogenous nucleic acid encoding the payload, receiver of surface marker. In some embodiments, the nucleic acid is a DNA. In some embodiments, the nucleic acid is a RNA.

A payload, receiver or surface marker can be expressed by a producer cell from a transgene or mRNA introduced into a producer cell by electroporation, chemical or polymeric transfection, viral transduction, mechanical membrane disruption, or other method. The producer cells can be modified e.g., by transfection of single or multiple copies of genes, transduction with a virus, or electroporation in the presence of DNA or RNA. In some embodiments, the exosome derived from the producer cell comprises the payload, receiver or surface marker that is expressed by the producer cell.

A payload can be expressed by a target cell from a transgene or mRNA introduced into an exosome by electroporation, chemical or polymeric transfection, viral transduction, mechanical membrane disruption, or other method when the target cell is contacted with the exosome.

In some instances, the exogenous nucleic acid is an RNA molecule, or a DNA molecule that encodes for an RNA molecule, that silences or represses the expression of a target gene. For example, the molecule can be a small interfering RNA (siRNA), an antisense RNA molecule or a short hairpin RNA (shRNA) molecule.

Messenger RNA can be derived from in vitro transcription of a cDNA plasmid construct containing the coding sequence corresponding to the payload, surface marker or receiver polypeptide. For example, the cDNA sequence corresponding to the polypeptide (e.g., a receiver polypeptide, a therapeutic polypeptide and/or a surface marker polypeptide) can be inserted into a cloning vector containing a promoter sequence compatible with specific RNA polymerases. For example, the cloning vector ZAP Express R pBK-CMV (Stratagene, La Jolla, Calif., USA) contains T3 and T7 promoter sequence compatible with T3 and T7 RNA polymerase, respectively. For in vitro transcription of sense mRNA, the plasmid is linearized at a restriction site downstream of the stop codon(s) corresponding to the end of the coding sequence of the receiver polypeptide. The mRNA is transcribed from the linear DNA template using a commercially available kit such as, for example, the RNAMaxx® High Yield Transcription Kit (from Stratagene, La Jolla, Calif., USA). In some instances, it can be desirable to generate 5'-m7GpppG-capped mRNA. As such, transcription of a linearized cDNA template can be carried out using, for example, the mMESSAGE mMACHINE High Yield Capped RNA Transcription Kit from Ambion (Austin, Tex., USA). Transcription can be carried out in a reaction volume of 20-100 µl at 37° C. for 30 min to 4 h. The transcribed mRNA is purified from the reaction mix by a brief treatment with DNase I to eliminate the linearized DNA template followed by precipitation in 70% ethanol in the presence of lithium chloride, sodium acetate or ammonium acetate. The integrity of the transcribed mRNA can be assessed using electrophoresis with an agarose-formaldehyde gel or commercially available Novex pre-cast TBE gels (e.g., Novex, Invitrogen, Carlsbad, Calif., USA).

Methods for transferring expression vectors into producer cells that are suitable to produce the exosomes described herein include, but are not limited to, viral mediated gene transfer, liposome mediated transfer, transformation, gene guns, transfection and transduction, e.g., viral mediated gene transfer such as the use of vectors based on DNA viruses such as adenovirus, adenoassociated virus and herpes virus, as well as retroviral based vectors. Examples of modes of gene transfer include e.g., naked DNA, $CaPO_4$ precipitation, DEAE dextran, electroporation, protoplast fusion, lipofection and cell microinjection.

Viral gene transfer can be used to transfect the producer cells with DNA encoding a payload (e.g., polypeptide or RNA), surface marker polypeptide or receiver polypeptide. A number of viruses can be used as gene transfer vehicles including Moloney murine leukemia virus (MMLV), adenovirus, adeno-associated virus (AAV), herpes simplex virus (HSV), lentiviruses such as human immunodeficiency virus 1 (HIV 1) and spumaviruses such as foamy viruses, for example (See, e.g., Osten et al., HEP 178:177-202 (2007)). Retroviruses, for example, efficiently transduce mammalian cells including human cells and integrate into chromosomes, conferring stable gene transfer.

Optionally, a fluorescent tracking molecule such as, for example, green fluorescent protein (GFP) can be transfected using a viral-based approach (Tao et al., Stem Cells 25:670-678 (2007)). Ecotopic retroviral vectors containing DNA encoding the enhanced green fluorescent protein (EGFP) or a red fluorescent protein (e.g., DsRed-Express) are packaged using a packaging cell such as, for example, the Phoenix-Eco cell line (distributed by Orbigen, San Diego, Calif). Packaging cell lines stably express viral proteins needed for proper viral packaging including, for example, gag, pol, and env. Supernatants from the Phoenix-Eco cells into which viral particles have been shed are used to transduce producer cells. In this instance, the percentage of cells expressing EGFP or DsRed-Express can be assessed by FACS. Other reporter genes that can be used to assess transduction efficiency include, for example, beta-galactosidase, chloramphenicol acetyltransferase, and luciferase as well as low-affinity nerve growth factor receptor (LNGFR), and the human cell surface CD24 antigen (Bierhuizen et al., Leukemia 13:605-613 (1999)).

Nonviral vectors can be used to introduce genetic material into suitable producer cell to generate exosomes. Nonviral-mediated gene transfer differs from viral-mediated gene transfer in that the plasmid vectors contain no proteins, are less toxic and easier to scale up, and have no host cell preferences. A number of delivery methods can be used to transfer nonviral vectors into suitable producer cells including chemical and physical methods.

Nonviral vectors can be introduced into suitable producer cells using synthetic macromolecules such as cationic lipids and polymers (Papapetrou et al., Gene Therapy 12:S118-S130 (2005)). Cationic liposomes, for example form complexes with DNA through charge interactions. The positively charged DNA/lipid complexes bind to the negative cell surface and are taken up by the cell by endocytosis. For example, the plasmid DNA (approximately 0.5 g in 25-100 μL of a serum free medium, such as, for example, OptiMEM (Invitrogen, Carlsbad, Calif.)) is mixed with a cationic liposome (approximately 4 μg in 25 μL of serum free medium) such as the commercially available transfection reagent Lipofectamine™ (Invitrogen, Carlsbad, Calif) and allowed to incubate for at least 20 min to form complexes. The DNA/liposome complex is added to suitable producer cell and allowed to incubate for 5-24 h, after which time transgene expression can be assayed. Alternatively, other commercially available liposome transfection agents can be used (e.g., in vivo GeneSHUTTLE™, Qbiogene, Carlsbad, Calif).

Alternatively or in addition, a cationic polymer such as, for example, polyethylenimine (PEI) can be used to transfect producer cells. Plasmid DNA is incubated with branched or linear PEIs varying in size from 0.8 K to 750 K (Sigma Aldrich, Saint Louis, Mo., USA; Fermetas, Hanover, Md., USA). PEI is prepared as a stock solution at 4.2 mg/ml distilled water and slightly acidified to pH 5.0 using HCl. The DNA can be combined with the PEI for 30 min at room temperature at various nitrogen/phosphate ratios based on the calculation that 1 μg of DNA contains 3 nmol phosphate and 1 μl of PEI stock solution contains 10 nmol amine nitrogen. The producer cells are seeded with the DNA/cationic complex, centrifuged at 280×g for 5 min and incubated in culture medium for 4 or more hours until transgene expression is assessed.

A plasmid vector can be introduced into a producer cell or an exosome using a physical method such as particle-mediated transfection, "gene gun", biolistics, or particle bombardment technology (Papapetrou, et al., (2005) Gene Therapy 12:S118-S130). In this instance, exogenous nucleic acid is absorbed onto gold particles and administered to cells or complexes by a particle gun. A reporter gene such as, for example, beta-galactosidase, chloramphenicol acetyltransferase, luciferase or green fluorescent protein can be used to assess efficiency of transfection.

Optionally, electroporation methods can be used to introduce a plasmid vector into suitable producer cell or exosome. Electroporation creates transient pores in the cell membrane, allowing for the introduction of various molecules into the cells and complexes including, for example, DNA and RNA as well as polypeptides and non-polypeptide therapeutic agents (e.g., therapeutic small molecules). Electroporation can be done using, for example, an ECM 600 electroporator (Genetronics, San Diego, Calif., USA). A number of alternative electroporation instruments are commercially available and can be used for this purpose (e.g., Gene Pulser Xcell™, BioRad, Hercules, Calif; Cellject Duo, Thermo Science, Milford, Mass.).

In some embodiments, an episomal vector which can persist in the host nucleus as autonomously replicating genetic units without integration into chromosomes (Papapetrou et al., Gene Therapy 12:S118-S130 (2005)) can be used to modify producer cells. These vectors exploit genetic elements derived from viruses that are normally extrachromosomally replicating in cells upon latent infection such as, for example, EBV, human polyomavirus BK, bovine papilloma virus-1 (BPV-1), herpes simplex virus-1 (HSV) and Simian virus 40 (SV40). Mammalian artificial chromosomes can also be used for nonviral gene transfer (Vanderbyl et al., Exp. Hematol. 33:1470-1476 (2005)).

Exogenous nucleic acids encoding payloads, receiver or surface molecules can be assembled into expression vectors by standard molecular biology methods known in the art, e.g., restriction digestion, overlap-extension PCR and Gibson assembly.

In some embodiments, the exosome comprises a payload, receiver or surface marker that is chemically conjugated. Chemical conjugation can be accomplished by covalent bonding of the payload, receiver or surface marker to another molecule, with or without use of a linker. The formation of such conjugates is within the skill of artisans and various techniques are known for accomplishing the conjugation, with the choice of the particular technique being guided by the materials to be conjugated. The addition of amino acids to the polypeptide (C- or N-terminal) which contain ionizable side chains, e.g., aspartic acid, glutamic acid, lysine, arginine, cysteine, histidine, or tyrosine, and are not contained in the active portion of the polypeptide sequence, serve in their unprotonated state as a potent nucleophile to engage in various bioconjugation reactions with reactive groups attached to polymers, e.g., homo- or hetero-bi-functional PEG (e.g., Lutolf and Hubbell, Biomacromolecules 2003; 4:713-22, Hermanson, Bioconjugate Techniques, London. Academic Press Ltd; 1996). Conjugation is not restricted to polypeptides but is applicable also for non-polypeptides, e.g., lipids, carbohydrates, nucleic acids, and small molecules.

In an embodiment, the payload, receiver or surface marker can be bound to the surface of an exosome through a biotin-streptavidin bridge. Any surface membrane proteins of an exosome can be biotinylated using an amine reactive biotinylation reagent such as, for example, EZ-Link Sulfo-NHS-SS-Biotin (sulfosuccinimidyl 2-(biotinamido)-ethyl-1, 3-dithiopropionate; Pierce-Thermo Scientific, Rockford, Ill., USA; See, e.g., Jaiswal et al., Nature Biotech. 21:47-51 (2003)). For example, exosomes can be incubated for 30 min at 4° C. in 1 mg/ml solution of sulfo-NHS-SS in phosphate-buffered saline. Excess biotin reagent is removed by washing the complexes with Tris-buffered saline. The biotinylated complexes are then reacted with the biotinylated payload, receiver or surface marker in the presence of streptavidin to form the conjugated exosome.

In some embodiments, the exosome comprises a payload, receiver or surface marker that is enzymatically conjugated, including using transpeptidases, sortases, and isopeptidases. These methods include enzymatic strategies such as, e.g., transpeptidase reaction mediated by a sortase enzyme to connect one polypeptide containing the acceptor sequence LPXTG or LPXTA with a polypeptide containing the N-terminal donor sequence GGG, see e.g., Swee et al., PNAS 2013. The methods also include combination methods, such as e.g., sortase-mediated conjugation of Click Chemistry handles (an azide and an alkyne), respectively, followed by a cyclo-addition reaction to chemically bond the antigen to the cell, see e.g., Neves et al., Bioconjugate Chemistry, 2013.

In certain embodiments, the payload, receiver or surface marker is loaded into the producer cell or exosome. A number of methods can be used to load a payload, receiver or surface marker into a producer cell or exosome. Suitable methods include, for example, hypotonic lysis, hypotonic dialysis, osmosis, osmotic pulsing, osmotic shock, ionophoresis, electroporation, sonication, microinjection, calcium precipitation, membrane intercalation, lipid mediated transfection, detergent treatment, viral infection, diffusion, receptor mediated endocytosis, use of protein transduction domains, particle firing, membrane fusion, freeze-thawing, mechanical disruption and filtration. Any one such method or a combination thereof can be used to load exosomes or producer cells.

Generally, any method that induces controlled injury can be used to load an agent, e.g., a payload, receiver or surface marker into or onto a producer cell or exosome. The controlled injury of the membrane of the producer cell or exosome can be caused by, for example, pressure induced by mechanical strain or shear forces, subjecting the cell to deformation, constriction, rapid stretching, rapid compression or pulse of high shear rate. The controlled injury leads to uptake of material, e.g., a payload, receiver or surface marker into the interior of the exosome or the cytoplasm of the producer cell from the surrounding cell medium. Any suitable controlled injury method can be used to generate the exosomes described herein.

Controlled cell injury as used herein includes: i) virus-mediated transfection (e.g., Herpes simplex virus, Adeno virus, Adeno-associated virus, Vaccinia virus, or Sindbis virus), ii) chemically-mediated transfection, e.g., cationic polymer, calcium phosphate, cationic lipid, polymers, and nanoparticles, such as cyclodextrin, liposomes, cationic liposomes, DEAE-dextran, polyethyleneimine, dendrimer, polybrene, calcium phosphate, lipofectin, DOTAP, lipofectamine, CTAB/DOPE, DOTMA; and iii) physically-mediated transfection, including direct injection, biolistic particle delivery, electroporation, laser-irradiation, sonoporation, magnetic nanoparticles, and controlled deformation (e.g., cell squeezing), as exemplified by microneedle, nano-needle, femtosyringe, atomic-force microscopy (AFM) tip, gene gun (e.g., gold nanoparticles), AmaxaNucleofector, phototransfection (multi-photon laser), impalefection, and magnetofection and other suitable methods known in the art.

For hypotonic lysis, producer cells or exosomes are exposed to low ionic strength buffer causing them to burst allowing loading of an agent, e.g., a payload, receiver or surface marker. Alternatively, controlled dialysis against a hypotonic solution to swell the cells or complexes and create pores in the cell or complex membrane is used. The cells or complexes are subsequently exposed to conditions that allow resealing of the membrane.

For electroporation, producer cells or exosomes are exposed to an electrical field which causes transient holes in the cell or complex membrane, allowing loading of an agent, e.g., a payload, receiver or surface marker.

For sonication, producer cells or exosomes are exposed to high intensity sound waves, causing transient disruption of the cell or complex membrane allowing loading of an agent, e.g., a payload, receiver or surface marker.

For detergent treatment, producer cells or exosomes are treated with a mild detergent which transiently compromises the cell or complex membrane by creating holes allowing loading of an agent, e.g., a payload, receiver or surface marker. After cells or complexes are loaded, the detergent is washed away thereby resealing the membrane.

For receptor mediated endocytosis, producer cells or exosomes that have a surface receptor which upon binding of the receiver or payload (e.g., therapeutic agent) induces internalization of the receptor and the associated receiver or payload.

For mechanical firing, producer cells or exosomes can be bombarded with a payload, receiver or surface marker attached to a heavy or charged particle such as, for example, gold microcarriers and are mechanically or electrically accelerated such that they traverse the cell membrane. Microparticle bombardment can be achieved using, for example, the Helios Gene Gun (from e.g., Bio-Rad, Hercules, Calif., USA).

In some embodiments, producer cells or exosomes can be loaded with a payload, receiver or surface marker by fusion with a synthetic vesicle such as, for example, a liposome. In this instance, the vesicles themselves are loaded with the payload, receiver or surface marker using one or more of the methods described herein or known in the art. Alternatively, the payload, receiver or surface marker can be loaded into the vesicles during vesicle formation. The loaded vesicles are then fused with the producer cells or exosomes under conditions that enhance membrane fusion. Fusion of a liposome, for example, can be facilitated using various inducing agents such as, for example, proteins, peptides, polyethylene glycol (PEG), and viral envelope proteins or by changes in medium conditions such as pH.

For filtration, producer cells or exosomes and the payload, receiver or surface marker can be forced through a filter of pore size smaller than the cell or complex causing transient disruption of the cell membrane and allowing the payload, receiver or surface marker to enter the cell or complex.

For freeze/thawing, producer cells or exosomes are subjected to several freeze thaw cycles, resulting in cell membrane disruption allowing loading of an agent, e.g., a payload, receiver or surface marker.

In certain embodiments, generating an exosome comprises the step of contacting an isolated membrane derived from a producer cell with a payload (e.g., a therapeutic agent). In some embodiments, generating an exosome comprises the step of contacting an isolated membrane derived from a producer cell with a receiver. In some embodiments, generating an exosome comprises the step of contacting an isolated membrane derived from a producer cell with a payload (e.g., a therapeutic agent) and a receiver Methods of Isolating Exosomes The exosomes can be isolated from the producer cells. It is contemplated that all known manners of isolation of exosomes are deemed suitable for use herein. For example, physical properties of exosomes can be employed to separate them from a medium or other source material, including separation on the basis of electrical charge (e.g., electrophoretic separation), size (e.g., filtration, molecular sieving, etc), density (e.g., regular or gradient centrifugation) and Svedberg constant (e.g., sedimentation with or without external force, etc). Alternatively, or additionally, isolation can be based on one or more biological properties, and include methods that can employ surface markers (e.g., for precipitation, reversible binding to solid phase, FACS separation, specific ligand binding, non-specific ligand binding, etc.). In yet further contemplated methods, the exosomes can also be fused using chemical and/or physical methods, including PEG-induced fusion and/or ultrasonic fusion.

Isolation (and enrichment) can be done in a general and non-selective manner (typically including serial centrifugation). Alternatively, isolation and enrichment can be done in a more specific and selective manner (e.g., using producer cell-specific surface markers). For example, specific surface markers can be used in immunoprecipitation, FACS sorting and bead-bound ligands for magnetic separation etc.

In some embodiments, size exclusion chromatography can be utilized to isolate the exosomes. Size exclusion chromatography techniques are known in the art. Exemplary, non-limiting techniques are provided herein. In some embodiments, a void volume fraction is isolated and comprises the exosomes of interest. Further, in some embodiments, the exosomes can be further isolated after chromatographic separation by centrifugation techniques (of one or more chromatography fractions), as is generally known in the art. In some embodiments, for example, density gradient centrifugation can be utilized to further isolate the exosomes. Still further, in some embodiments, it can be desirable to further separate the producer cell-derived exosomes from exosomes of other origin. For example, the producer cell-derived exosomes can be separated from non-producer cell-derived exosomes by immunosorbent capture using an antigen antibody specific for the producer cell In some embodiments, the isolation of exosomes can involve combinations of methods that include, but are not limited to, differential centrifugation, size-based membrane filtration, concentration and/or rate zonal centrifugation.

Methods of Characterizing Exosomes

In some embodiments, exosomes are isolated and characterized by metrics including, but not limited to, size, shape, morphology, or molecular compositions such as nucleic acids, proteins, metabolites and lipids.

Exosomes can be assessed by methods known in the art including, but not limited to, transcriptomics, sequencing, proteomics, mass spectrometry or HPLC. Exosomes can further be assessed by methods that include, but are not limited to, electron microscopy, flow cytometry and Western blotting.

The composition of nucleotides associated with an isolated exosome composition (including RNAs and DNAs) can be measured using a variety of techniques that are well known to those of skill in the art (e.g., quantitative or semi-quantitative RT-PCR, Northern blot analysis and solution hybridization detection). In a particular embodiment, the level of at least one RNA is measured by reverse transcribing RNA from the exosome composition to provide a set of target oligodeoxynucleotides, hybridizing the target oligodeoxynucleotides to one or more RNA-specific probe oligonucleotides (e.g., a microarray that comprises RNA-specific probe oligonucleotides) to provide a hybridization profile for the exosome composition and comparing the exosome composition hybridization profile to a hybridization profile generated from a control sample. An alteration in the signal of at least one RNA in the test sample relative to the control sample is indicative of the RNA composition.

Also, a microarray can be prepared from gene-specific oligonucleotide probes generated from known RNA sequences. The array can contain two different oligonucleotide probes for each RNA, one containing the active, mature sequence and the other being specific for the precursor of the RNA (for example miRNA and pre-miRNAs). The array can also contain controls, such as one or more mouse sequences differing from human orthologs by only a few bases, which can serve as controls for hybridization stringency conditions. tRNAs and other RNAs (e.g., rRNAs, mRNAs) from both species can also be printed on the microchip, providing an internal, relatively stable, positive control for specific hybridization. One or more appropriate controls for non-specific hybridization can also be included on the microchip. For this purpose, sequences are selected based upon the absence of any homology with any known RNAs.

The microarray can be fabricated using techniques known in the art. For example, probe oligonucleotides of an appropriate length, e.g., 40 nucleotides, are 5-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary RNAs, in the exosome preparation. According to an embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding RNA in the exosomes.

The identity of the producer cells or exosomes can be assessed by in vitro assays. For example, the identity of the producer cells or exosomes is assessed by counting the number of cells or complexes in a population, e.g., by microscopy, by flow cytometry, or by hemocytometry. Alternatively or in addition, the identity of the producer cells or exosomes is assessed by analysis of protein content of the cell or complex, e.g., by flow cytometry, Western blot, immunoprecipitation, fluorescence spectroscopy, chemiluminescence, mass spectrometry, or absorbance spectroscopy. In an embodiment, the protein content assayed is a surface protein, e.g., a differentiation marker, a receptor, a co-receptor, a transporter, a glycoprotein. In some embodiments, the identity of the producer cells or exosomes is assessed by analysis of the receiver content of the cell or complex, e.g., by flow cytometry, Western blot, immunoprecipitation, fluorescence spectroscopy, chemiluminescence, mass spectrometry or absorbance spectroscopy. For example, the identity of the producer cells or exosomes can be assessed by the mRNA content of the cells or complexes, e.g., by RT-PCR, flow cytometry or northern blot. The identity of the producer cells can be assessed by nuclear material content, e.g., by flow cytometry, microscopy, or southern blot, using, e.g., a nuclear stain or a nucleic acid probe. Alternatively or in addition, the identity of the producer cells or exosomes is assessed by lipid content of the cells or complexes, e.g., by flow cytometry, liquid chromatography or by mass spectrometry.

Methods of Using Exosomes

Provided are compositions, methods, kits, and reagents for treatment or prevention of diseases or conditions in humans and other mammals. In some embodiments, pharmaceutical compositions comprising exosomes can be used for therapeutic purposes, such as the treatment or prevention of disease, disorder or condition.

Provided herein are methods of targeting a cell or tissue to treat or prevent a disease, disorder or condition. The subject can suffer from the disease, disorder or condition or can be at risk of developing the disease, disorder or condition. The methods provided herein include the administration of suitable exosomes described herein in an amount effective to substantially deliver the payload to the target cell or tissue, thereby preventing or treating the disease, disorder or condition. In some embodiments, the exosome is formulated as a pharmaceutical composition. In some embodiments, the pharmaceutical composition is formulated for intravenous injection to the subject. The compositions can be administered once to the subject. Alternatively, multiple administrations can be performed over a period of time. For example, two, three, four, five, or more administrations can be given to the subject. In some embodiments, administrations can be given as needed, e.g., for as long as symptoms associated with the disease, disorder or condition persist. In some embodiments, repeated administrations can be indicated for the remainder of the subject's life. Treatment periods can vary and could be, e.g., no longer than a year, six months, three months, two months, one month, two weeks, one week, three days, two days, or no longer than one day.

In some embodiments, the pharmaceutical composition is administered at a frequency sufficient to effectively increase the concentration of payload in the target cell or tissue above a level that is associated with a symptom of the disease, disorder or condition.

In some embodiments, the time interval between repeated administrations within a treatment period is no longer than the period in which the number of exosomes in circulation is reduced to less than about 5%, 10%, 15%, 20%, 25%, 30%, 35%, 40%, 45%, 50%, 55%, 60%, 65%, 70%, 75%, 80%, 85%, 90%, or 95% of the number of exosomes present in the administered pharmaceutical composition.

In certain embodiments, the non-therapeutic exosome is administered separately to and at a different dosage than the therapeutic exosomes. In certain embodiments, the dosage of the non-therapeutic exosome is greater than the dosage of the therapeutic exosome.

In certain embodiments, the dosage of the non-therapeutic exosome is the same as the therapeutic exosome. In some embodiments, the dosage of the non-therapeutic exosome is between 1.1-fold to 1.5-fold, 1.0-fold to 2.0-fold, 2.0-fold to 3.0-fold, 3.0-fold to 4.0-fold, 4.0-fold to 5.0-fold, 5.0-fold to 10.0-fold, 10.0-fold to 20.0-fold, 10.0-fold to 100-fold or 100-fold to 1,000-fold greater than the dosage of the therapeutic exosome. In certain embodiments, the dosage of the non-therapeutic exosome is less than the dosage of the therapeutic exosome. In certain embodiments, the dosage of the non-therapeutic exosome is between 1.1-fold to 1.5-fold, 1.0-fold to 2.0-fold, 2.0-fold to 3.0-fold, 3.0-fold to 4.0-fold, 4.0-fold to 5.0-fold, 5.0-fold to 10.0-fold, 10.0-fold to 20.0-fold, 10.0-fold to 100-fold or 100-fold to 1,000-fold less than the dosage of the therapeutic exosome.

In certain embodiments, the non-therapeutic exosome is administered concurrently to the therapeutic exosome. In certain embodiments, the non-therapeutic exosomes and the therapeutic exosomes are co-formulated as a single pharmaceutical composition.

In certain embodiments, the non-therapeutic exosomes are administered between 1 minute and 48 hours prior to the administration of the therapeutic exosomes. In particular embodiments, the non-therapeutic exosomes are administered 1 min to 5 min, 5 min to 10 min, 10 min to 15 min, 15 min to 20 min, 20 min to 25 min, 25 min to 30 min, 30 min to 45 min, 45 min to 60 min, 60 min to 120 min, 2 h to 3 h, 3 h to 5 h, 5 h to 10 h, 2 h to 12 h, 12 h to 18 h, 18 h to 24 h, 24 h to 48 h or 48 h to one week prior to administration of the therapeutic exosomes.

In certain embodiments, the non-therapeutic exosomes, the therapeutic exosomes or both the non-therapeutic exosomes and therapeutic exosomes are administered as repeated administration steps.

In certain embodiments, a plurality of distinct exosomes harboring distinct receivers, payloads or both distinct receivers or payloads are administered either concurrently or separately.

An effective amount of the composition is provided based, at least in part, on the target tissue, target cell type, means of administration, physical characteristics of the exosome (e.g., size, and in some cases the extent of molecules to be delivered) and other determinants. In general, an effective amount of the composition provides efficient cellular response of the target cell. Increased efficiency can be demonstrated by increased cell transfection (i.e., the percentage of cells transfected with the exosome constituents), increased cellular response or reduced innate immune response of the host subject.

The dosing and frequency of the administration of the exosomes and pharmaceutical compositions thereof can be determined, e.g., by the attending physician based on various factors such as the severity of disease, the patient's age, sex and diet, the severity of any inflammation, time of administration and other clinical factors. In an example, an intravenous administration is initiated at a dose which is minimally effective, and the dose is increased over a preselected time course until a positive effect is observed. Subsequently, incremental increases in dosage are made limiting to levels that produce a corresponding increase in effect while taking into account any adverse effects that can appear.

In certain embodiments, doses of exosomes are adminis- tered at intervals such as once daily, every other day, once weekly, twice weekly, once monthly or twice monthly.

In some embodiments, the compositions are administered at least twice over a treatment period such that the disease, disorder or condition is treated, or a symptom thereof is ameliorated. In some embodiments, the compositions are administered at least twice over a treatment period such that the disease, disorder or condition is treated or a symptom thereof is prevented. In some embodiments, the pharmaceutical composition is administered a sufficient number of times over a treatment period such that a sufficient amount of payload is delivered to the target cell or tissue during the treatment period. In some embodiments, the pharmaceutical composition is administered a sufficient number of times over a treatment period such that a sufficient amount of payload is delivered to the target cell or tissue during the treatment period such that one or more symptoms of the disease, disorder or condition is prevented, decreased, ame- liorated or delayed. In some embodiments, increasing the payload concentration in the target cell or tissue includes increasing the peak concentration, while in others it includes increasing the average concentration. In some embodiments, a substantial increase during the treatment period can be determined by comparing a pretreatment or post-treatment period in the human subject, or by comparing measurements made in a population undergoing treatment with a matched, untreated control population.

In some embodiments, the pharmaceutical composition is administered a sufficient number of times per treatment period such that the concentration of payload in the target cell or tissue is increased for at least about one week, two weeks, three weeks, four weeks, one month, two months, three months, four months, five months, six months or greater than six months. In some embodiments, the pharmaceutical composition is administered a sufficient number of times per treatment period such that the concentration of payload in the target cell or tissue is increased for a period of time at least as long as the treatment period.

In some embodiments, the exosomes are administered, e.g., intravenously to the circulatory system or a tissue of a mammalian subject, such as a human. In some embodi- ments, the exosomes provide a natural barrier between a payload (e.g., therapeutic agent) and the immune system. In some embodiments, the exosomes are capable of residing in the circulatory system or tissue of a subject for an extended period of time allowing delivery of a more efficient thera- peutic effect than what can be achieved by delivery through other methods currently used.

In certain embodiments, the exosomes are optionally modified by contacting with sialyltransferase prior to admin- istration. Sialyltransferases are enzymes that transfer sialic acid to nascent oligosaccharide. Each sialyltransferase is specific for a particular sugar substrate. Sialyltransferases add sialic acid to the terminal portions of the sialylated glycolipids (gangliosides) or to the N- or O-linked sugar chains of glycoproteins. In certain embodiments, contacting exosomes with sialyl transferase prevents removal of the exosomes by the liver. In certain embodiments, contacting exosomes with sialyl transferase prevents removal of the exosomes by the liver by modulation of the binding of exosomes and liver cells that is mediated through asialogly- coprotein receptor.

In certain embodiments, the exosomes are optionally administered either concurrently or sequentially with an agent that inhibits phagocytosis by inhibiting, impeding or preventing the phagocytosis of exosomes by phagocytes. Agents that inhibit phagocytosis include but are not limited to, CD47 on the exosome surface.

Exosomes can interact with a target cell in a tissue or circulatory system of the subject. In some embodiments, the composition or phenotype of the target cell is modified subsequent to its interaction with the complex. In some embodiments, the modification of the target cell leads to a reduction in disease burden, can alleviate a symptom of the disease or has some other treatment effect.

In some embodiments, exosomes interact with a target cell and increase the concentration of a therapeutic agent in the target cell. In some embodiments, a therapeutic agent is delivered to the cytoplasm of the target cell. In some embodiments, the therapeutic agent is a functional mRNA which can be translated in the cytoplasm of the target cell. A resulting polypeptide can be functional and modulate signaling or regulatory behavior, morphology or growth of the target cell.

Provided are methods of treating a disease, disorder or condition comprising administering to a subject in need thereof a pharmaceutical composition comprising the exo- somes described herein, optionally in form of the dosage form described herein, in an amount effective to treat the disease, disorder or condition.

In some embodiments, the preparations comprise exo- somes comprising a payload that is capable, upon contact, of killing or restoring the functionality of an infected, impaired or dysregulated cell or tissue that is associated with the disease, disorder or condition. In some embodiments, the exosome facilitates the contacting of the infected, impaired or dysregulated cell or tissue with the payload in sufficient proximity and for a sufficient duration to bring about the killing or restoring the functionality of the infected, impaired or dysregulated cell or tissue. In some embodi- ments, an infected or dysregulated cell or tissue is killed thereby treating the disease, disorder or condition. In other embodiments an impaired or dysregulated cell or tissue is restored thereby treating the disease, disorder or condition. For example, an impaired enzyme function can be restored or a dysregulated enzyme function regulated.

In some embodiments, pharmaceutical compositions comprising exosomes can be used for treatment of any of a variety of diseases, disorders, and/or conditions, including but not limited to one or more of the following: autoimmune disorders (e.g., diabetes, lupus, multiple sclerosis, psoriasis, rheumatoid arthritis); inflammatory disorders (e.g., arthritis, pelvic inflammatory disease); infectious diseases (e.g., viral infections (e.g., HIV, HCV, RSV), bacterial infections, fun- gal infections, sepsis); neurological disorders (e.g., Alzheimer's disease, Huntington's disease; autism; Duch- enne muscular dystrophy); cardiovascular disorders (e.g., atherosclerosis, hypercholesterolemia, thrombosis, clotting disorders, angiogenic disorders such as macular degenera- tion); proliferative disorders (e.g., cancer, benign neo- plasms); respiratory disorders (e.g., chronic obstructive pul- monary disease); digestive disorders (e.g. inflammatory bowel disease, ulcers); musculoskeletal disorders (e.g. fibromyalgia, arthritis); endocrine, metabolic, and nutritional disorders (e.g., diabetes, osteoporosis); urological disorders (e.g., renal disease); psychological disorders (e.g., depression, schizophrenia); skin disorders (e.g., wounds, eczema); and blood and lymphatic disorders (e.g., anemia, hemophilia).

In an embodiment, the exosome is administered to a subject in need thereof to treat cancers. Such cancers include, but are not limited to, pancreatic cancers, biliary tract cancer, liver cancer, breast cancer, glioma, lung cancer, leukemias, gastrointestinal cancers, neuroendocrine tumors, throat cancers, melanoma, colon cancer, prostate cancer, ovarian cancer, testicular cancer, ocular cancer and kidney cancer.

In an embodiment, the exosome is administered to a subject in need thereof treat autoimmune disease. Such autoimmune diseases include, but are not limited to, multiple sclerosis, peripheral neuritis, Sjogren's syndrome, rheumatoid arthritis, graft versus host disease, alopecia, Autoimmune pancreatitis, Behcet's disease, Bullous pemphigoid, Celiac disease, Devic's disease (neuromyelitis optica), Glomerulonephritis, IgA nephropathy, assorted vasculitides, scleroderma, diabetes, arteritis, vitiligo, ulcerative colitis, irritable bowel syndrome, psoriasis, uveitis and systemic lupus erythematosus.

In an embodiment, the exosome is administered to a subject in need thereof to treat neurodegenerative diseases and brain-related conditions. Such indications include, but are not limited to, Parkinson's disease, Alzheimer's, stroke, aneurysms, neuroencephalitis and ALS.

In an embodiment, the exosome is administered to a subject in need thereof to treat a disease, disorder or condition selected from Table 8 and Table 9.

Diseases, disorders and conditions associated with target cells or tissues that can be treated or prevented by administering exosomes include, but are not limited to: diseases associated with infectious agents or pathogens (e.g., bacterial, fungal, viral, parasitic infections), disease associated with toxic proteins, diseases associated with the accumulation of lipids, diseases associated with apoptotic, necrotic, aberrant or oncogenic mammalian cells and metabolic diseases.

In some embodiments, provided are methods of treating diseases, including, but not limited to, metabolic diseases, cancers, clotting and anti-clotting diseases. The methods include administering to a subject in need thereof a pharmaceutical composition of exosomes in an amount sufficient to treat the metabolic disease, the cancer, the clotting disease or anti-clotting disease of the subject.

Diseases, disorders and conditions associated with targets in the circulatory system that can be treated or prevented by administering exosomes are described herein.

Diseases, disorders and conditions associated with targets in the circulatory system that can be treated or prevented by administering exosomes include, but are not limited to: diseases associated with infectious agents or pathogens (e.g., bacterial, fungal, viral, parasitic infections), diseases associated with apoptotic, necrotic, aberrant or oncogenic mammalian cells and metabolic diseases.

Provided herein, in some embodiments, are methods for the treatment or prevention of diseases or conditions that are associated with molecules or entities that reside, at least in part, in specific target cells or tissues. The methods comprise, in certain embodiments, administering to a subject in need thereof exosomes in an amount effective to treat or prevent the disease or condition that is associated with molecules or entities that reside, in specific target cells or tissues.

Provided herein are methods of inducing in vivo delivery of exosomes in a mammalian subject in need thereof. Therein, an effective amount of a composition containing an exosome is administered to the subject using the delivery methods described herein. The exosome is provided in an amount such that the exosome is localized into a cell of the subject. The cell in which the exosome is localized, or the tissue in which the cell is present, can be targeted with one or more than one rounds of exosome administration.

Provided herein are methods of transplanting cells containing or producing exosomes to a mammalian subject. Administration of cells to mammalian subjects is known to those of ordinary skill in the art, such as local implantation (e.g., topical or subcutaneous administration), organ delivery or systemic injection (e.g., intravenous injection or inhalation), as is the formulation of cells in pharmaceutically acceptable carrier.

Provided are methods of inducing a cellular response using the exosomes described herein. Such response can be in vivo, ex vivo, in culture, or in vitro. For example, a target cell population is contacted with an effective amount of a composition containing an exosome. The population is contacted under conditions such that the exosome is localized into one or more cells of the cell population.

In an embodiment, the exosome is administered as part of a treatment regimen that further includes administration of a second, standard-of-care therapy.

In certain embodiments, the administered exosome directs up-regulation of (via expression in the cell, delivery in the cell, or induction within the cell) of one or more polypeptides that provide a functional activity which is substantially absent in the target cell to which the polypeptide is delivered. For example, the missing functional activity can be enzymatic, structural, or gene regulatory in nature. In related embodiments, the administered exosome directs up-regulation of one or more polypeptides that increases (e.g., synergistically) a functional activity which is present but substantially deficient in the target cell in which the polypeptide is up-regulated.

In certain embodiments, the administered exosome directs up-regulation of (via expression in the cell, delivery in the cell, or induction within the cell) of one or more polypeptides that replace a polypeptide (or multiple polypeptides) that is substantially absent in the target cell in which the polypeptide is up-regulated. Such absence can be due to genetic mutation of the encoding gene or regulatory pathway thereof. In some embodiments, the polypeptide increases the level of an endogenous protein in the cell to a desirable level; such an increase can bring the level of the endogenous protein from a subnormal level to a normal level, or from a normal level to a super-normal level.

Alternatively, the polypeptide functions to antagonize the activity of an endogenous protein present in, on the surface of, or secreted from the cell. Usually, the activity of the endogenous protein is deleterious to the subject, for example, due to mutation of the endogenous protein resulting in altered activity or localization. Additionally, the polypeptide antagonizes, directly or indirectly, the activity of a biological moiety present in, on the surface of or secreted from the cell. Examples of antagonized biological moieties include lipids (e.g., cholesterol), a lipoprotein (e.g., low density lipoprotein), a nucleic acid, a carbohydrate, a protein toxin such as shiga and tetanus toxins or a small molecule toxin such as botulinum, cholera and diphtheria toxins. Additionally, the antagonized biological molecule can be an endogenous protein that exhibits an undesirable activity, such as a cytotoxic or cytostatic activity.

Modulation of Cell Fate

Provided are methods of inducing an alteration in cell fate in a target mammalian cell. The target mammalian cell can be a precursor cell and the alteration can involve driving differentiation into a lineage, or blocking such differentiation. Alternatively, the target mammalian cell can be a differentiated cell, and the cell fate alteration includes driving de-differentiation into a pluripotent precursor cell, or blocking such de-differentiation, such as the dedifferentiation of cancer cells into cancer stem cells. In situations where a change in cell fate is desired, effective amounts of exosomes encoding a cell fate inductive molecule or signal as a payload is introduced into a target cell under conditions such that an alteration in cell fate is induced. In some embodiments, the exosomes are useful to reprogram a subpopulation of cells from a first phenotype to a second phenotype. Such a reprogramming can be temporary or permanent. Optionally, the reprogramming induces a target cell to adopt an intermediate phenotype.

Additionally, the methods can be used to generate induced pluripotent stem cells (iPS cells). The use of iPS cells generated using the methods described herein is expected to have a reduced incidence of teratoma formation.

Also provided are methods of reducing cellular differentiation in a target cell population. For example, a target cell population containing one or more precursor cell types is contacted with a composition having an effective amount of an exosome composition, under conditions such that the exosome reduces the differentiation of the precursor cell. In non-limiting embodiments, the target cell population contains injured tissue in a mammalian subject or tissue affected by a surgical procedure. The precursor cell is, e.g., a stromal precursor cell, a neural precursor cell or a mesenchymal precursor cell.

Targeting Diseased Cells

Provided herein are methods for targeting pathogenic or diseased cells or tissues, including cancer cells, using exosomes that deliver cytotoxic or cytostatic molecules. The molecule can be delivered into the target pathogenic cell exclusively or preferentially to reduce off-target effects of the therapeutic. Receivers described herein can be used that are capable of targeting the exosomes preferentially to the target pathogenic cell.

Methods of Gene Silencing

The exosome compositions described herein are useful to silence (e.g., prevent or substantially reduce) expression of one or more target genes in a target cell population. An exosome containing or encoding a polypeptide capable of directing sequence-specific histone H3 methylation is introduced into the target cells under conditions such that the polypeptide is translated and reduces gene transcription of a target gene via histone H3 methylation and subsequent heterochromatin formation. In some embodiments, the silencing mechanism is performed on a cell population present in a mammalian subject. By way of non-limiting example, a useful target gene is a mutated Janus Kinase-2 family member, wherein the mammalian subject expresses the mutant target gene suffers from a myeloproliferative disease resulting from aberrant kinase activity.

Administration of exosomes carrying siRNAs are also provided herein. As has been previously demonstrated in yeast, sequence-specific trans-silencing is an effective mechanism for altering cell function. While this mechanism functions in cis- with centromeric regions of DNA, sequence-specific trans silencing is possible through co-transfection with double-stranded siRNAs for specific regions of DNA and concomitant RNAi-directed silencing of the siRNA ribonuclease Eri1 (Buhler et al. Cell 2006, 125, 873-886).

Modulation of Biological Pathways

The efficient delivery of molecules (payloads) via exosomes into cells provides a desirable mechanism of modulating target biological pathways. Such modulation includes antagonism or agonism of a given pathway. In an embodiment, a method is provided for antagonizing a biological pathway in a target cell by contacting the cell with an effective amount of an exosome composition comprising a polypeptide or comprising a functional nucleic acid (e.g., mRNA) which encodes a polypeptide, under conditions such that the peptide is localized into the target cell or the polypeptide is capable of being translated in the cell from the nucleic acid, wherein the polypeptide inhibits the activity of another polypeptide functional in the biological pathway. Exemplary biological pathways are those defective in an autoimmune or inflammatory disorder such as multiple sclerosis, rheumatoid arthritis, psoriasis, lupus erythematosus, ankylosing spondylitis colitis, or Crohn's disease; in particular, antagonism of the IL-12 and IL-23 signaling pathways are of particular utility. (See Kikly K, Liu L, Na S, Sedgwick J D (2006) Curr. Opin. Immunol. 18 (6): 670-5). Further, provided are modified nucleic acids encoding an antagonist for chemokine receptors; chemokine receptors CXCR-4 and CCR-5 are required for, e.g., HIV entry into host cells (Arenzana-Seisdedos F et al. (1996) Nature 383:400).

Alternatively, provided are methods of agonizing a biological pathway in a target cell. Exemplary agonized biological pathways include pathways that modulate cell fate determination. Such agonization is reversible or, alternatively, irreversible.

In some embodiments, contacting a target cell with an exosome modulates a biological pathway that causes a cytotoxic cellular response. In some embodiments, the polypeptide is a protein cytotoxic to the target cell.

In some embodiments, exosomes can similarly carry metabolites, lipids, or small molecules that modulate the activity of a biological pathway. Such molecules can be recombinant, synthesized or natively isolated.

Methods of Nucleic Acid Delivery

Methods are provided to enhance nucleic acid delivery from exosomes into a cell population, in vivo, ex vivo, or in culture. For example, a cell culture containing a plurality of target cells (e.g., eukaryotic cells such as yeast or mammalian cells) is contacted with a composition comprising an exosome having at least one nucleic acid, which optionally has a translatable region. The nucleic acid within the exosome composition exhibits enhanced retention in the target cell relative to a corresponding free nucleic acid. The retention of the nucleic acid within the exosome composition is greater than the retention of the free nucleic acid. In some embodiments, it is at least about 50%, 75%, 90%, 95%, 100%, 150%, 200% or more than 200% greater than the retention of the free nucleic acid. Such retention advantage can be achieved by one round of transfection with the nucleic acid within an exosome composition, or can be obtained following repeated rounds of transfection.

In some embodiments, the nucleic acid within the exosome composition is delivered to a target cell population with one or more additional nucleic acids. Such delivery can be at the same time, or the nucleic acid within the exosome composition is delivered prior to delivery of the one or more additional nucleic acids. The additional one or more nucleic acids can be within the same or within a separate exosome composition or free nucleic acids. It is understood that the initial presence of the nucleic acid within an exosome composition does not substantially induce an innate immune response of the target cell population and, moreover, that the innate immune response will not be activated by the later presence of the additional nucleic acids. In this regard, the nucleic acid within the exosome composition cannot itself contain a translatable region, if the protein desired to be present in the target cell population is translated from the additional nucleic acid.

The nucleic acid within the exosome composition can have at least one nucleoside modification or can be unmodified.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., dosages, amounts, temperatures, dosing schedules etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. Sec, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ *Ed.* (Plenum Press) Vols A and B (1992).

Methods

Production, isolation and formulation of exosomes for intravenous injection are performed as described above. Methods described herein can be carried out as known in the art and described in PCT Application No. PCT/US14/65304 SYNTHETIC MEMBRANE-RECEIVER COMPLEXES incorporated in its entirety by reference herein.

Example 1: Administration of Unlabeled Exosomes Prior to Labeled Exosomes to Determine Alterations in Tissue-Specific Uptake To determine whether exosome pre-treatment could lead to increased uptake in tissues beyond the liver and spleen, the following experiment was performed. Conditioned culture media from 293T cells was collected and centrifuged at 300-800×g for 5 minutes at room temperature to remove cells and large debris. Media supernatant was then supplemented with 1000 U/L Benzonase® and incubated at 37° C. for 1 hour in a water bath. Supernatant was collected and centrifuged at 16,000×g for 30 minutes at 4° C. to remove residual cell debris and other large contaminants. Supernatant was then ultracentrifuged at 133,900×g for 3 hours at 4° C. to pellet the exosomes. Supernatant was discarded and residual media was aspirated from the bottom of the tube. The pellet was then resuspended in 200-1000 µL PBS (—Ca—Mg).

To further enrich exosome populations, the pellet was processed via sucrose density gradient purification as defined in Table 1 below:

TABLE 1

| Sucrose Density Gradient: | | |
|---|---|---|
| Working Percentage (%) | 65% Stock Vol. (mL) | Milli-Q Vol. (mL) |
| 50 | 3.85 | 1.15 |
| 40 | 3.08 | 1.92 |
| 25 | 1.92 | 3.08 |
| 10 | 0.46 | 2.54 |

The gradient was spun at 200,000×g for 16 hours at 4° C. in a 12 mL Ultra-Clear™ (Beckman Coulter catalogue #344059) tube placed in a SW 41 Ti rotor to separate the exosome fraction.

The exosome layer was gently removed from the top layer and diluted in ~32.5 mL PBS in a 38.5 mL Ultra-Clear™ (Beckman Coulter catalogue #344058) tube and ultracentrifuged again at 133,900×g for 3 hours at 4° C. to pellet the purified exosomes. The resulting pellet was resuspended in a minimal volume of PBS (~200 µL) and stored at 4° C.

To radiolabel the purified exosomes for in vivo imaging, $1 \times 10^{11}$ purified exosomes in 100 µL were diluted with HEPES (200 µL, 0.1 M, pH 8.5) and conjugated to p-SCN-Bn-DFO (5 µg) for one hour at 37° C. followed by overnight incubation at 4° C., separately. DFO-exosomes were incubated with 89Zr (7.5 mCi) diluted in HEPES (100 µL, 1 M, pH 7.3) for one hour at 37° C. and purified on a qEv column. This resulted in a total yield (0.4 mCi of 89Zr-DFO-exosomes in up to 0.8 mL PBS at 100 µCi/$1 \times 10^{10}$ exosomes. Quality control (HPLC) was performed prior to release to ensure >95% RCP.

In Vitro Stability

Exosomes (20 Ci/$2 \times 10^{10}$) were incubated at room temperature in:
   a. Formulation buffer
   b. Mouse serum (10% v/v exosome solution in serum, if possible) 2 hours after initiation of incubation solutions were injected into HPLC to determine stability of tracer.

In Vivo Imaging

Mice (SKH-1, n=8, age 5-8 weeks) were randomized into two groups, weighed and injected (with the second group injected immediately after the first group's dynamic scan was over) with $1 \times 10^{10}$/g exosomes to give a minimum radioactive dose of 100 µCi/mouse. Both groups are injected intravenously. Group 1 was injected with the radiolabeled exosomes only while group 2 was injected first with unlabeled 293SF exosomes and 5 minutes later with the radiolabeled exosomes (Table 2).

Mice received a whole body PET/CT scan in a 4-mouse hotel using the following schedule: static imaging at 4 h (20 min), 24 h (Thursday, 20 min). Each imaging time point was followed by CT for anatomical reference.

After the last imaging time point, mice were euthanized and the following organs were collected, weighed and counted in the gamma counter: Blood, lung (both), liver (lobe), spleen, pancreas, kidney (both), stomach (whole, emptied), small intestine (whole, emptied), large intestine (whole, emptied) muscle, brain and tail.

Organs were allowed to decay for 2-3 days when counts were extremely high, and were counted again.

TABLE 2

| | | | | | |
|---|---|---|---|---|---|
| In Vivo Imaging | | | | | |
| Group (mouse # and type) | Blocking | Tracer | Injection route | Imaging | Imaging time points |
| 1 (n = 4, SKH-1) | N/A | $^{89}$Zr-DFO-exosomes (293T, 100 μCi, <150 μL) | IV | Whole body PET/CT using a 4 mouse hotel | 4 h and 24 h (20 min) |
| 2 (n = 4, SKH-1) | 293SF exosomes (1 × 10$^{12}$, <100 μL) 5 minutes before tracer | | | | |

Results

Figure 3:
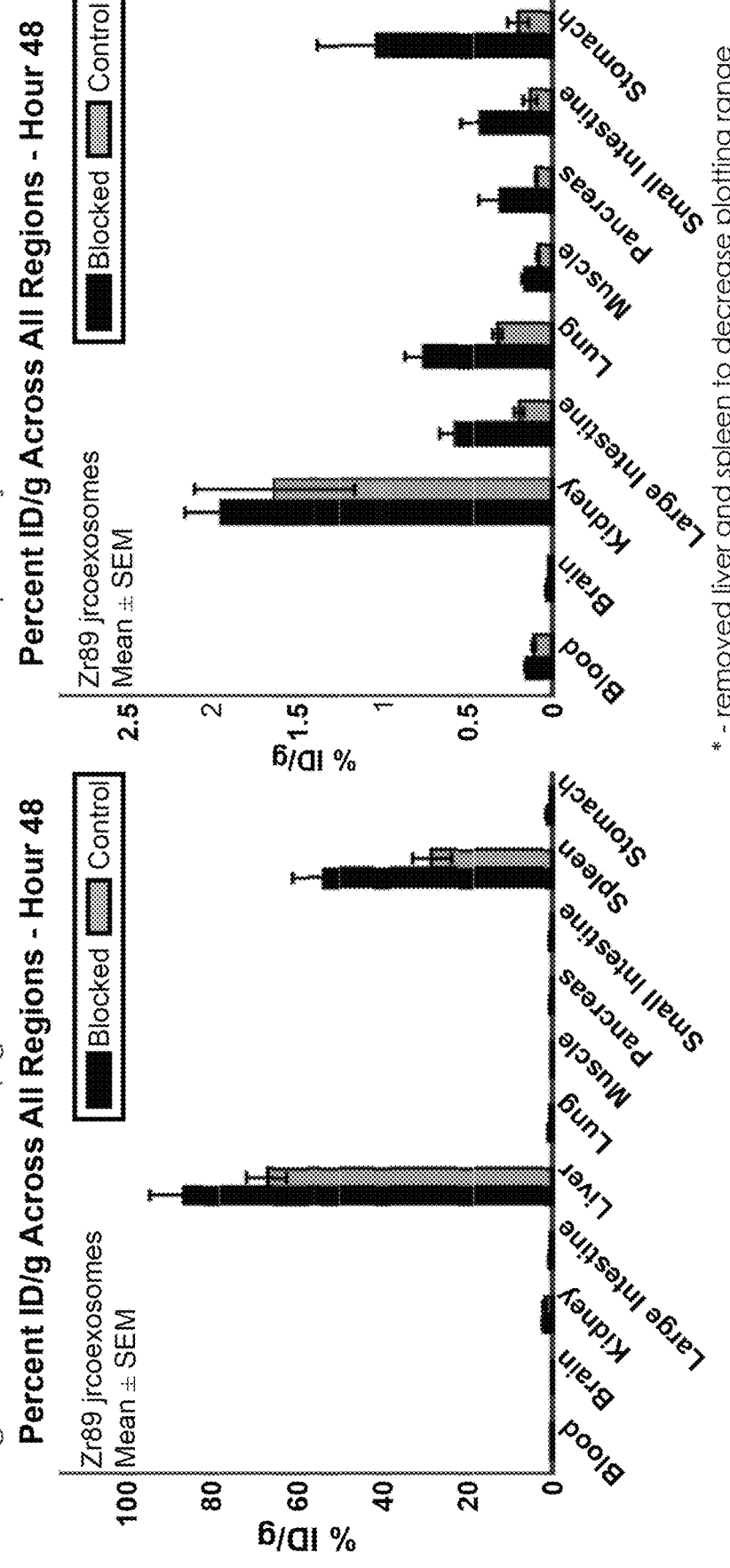
FIG. 3 is a chart showing the amount of $^{89}$Zr-DFO taken up by various mouse tissues 48 hours after treatment with either $^{89}$Zr-DFO-labeled exosomes (Control) or unlabeled exosomes followed by $^{89}$Zr-DFO-labeled exosomes (Blocked). $^{89}$Zr-DFO levels are shown in percent injected dose per gram of organ weight. The chart at right shows the same data replotted after removing liver and spleen levels.
Figure 4:
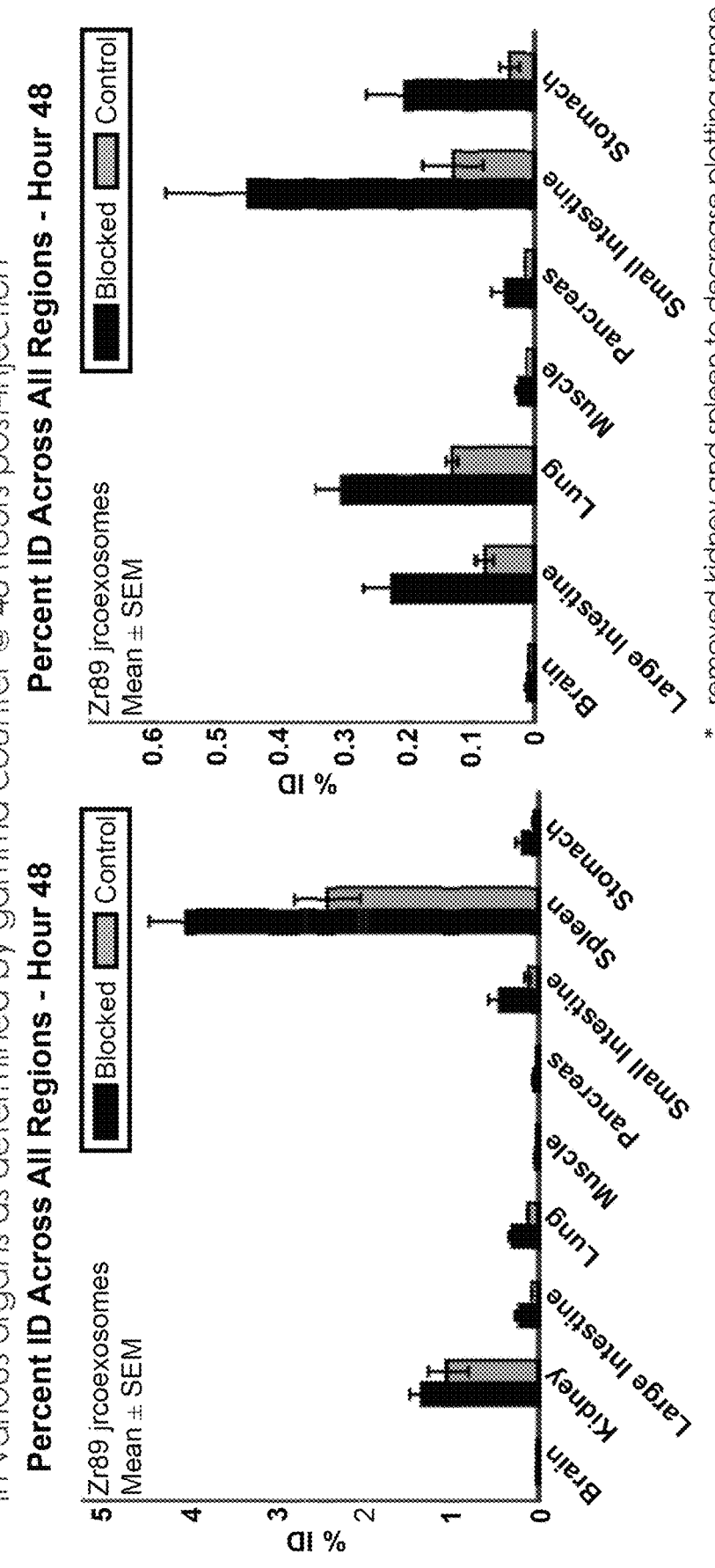
FIG. 4 is a chart showing the amount of $^{89}$Zr-DFO taken up by various mouse tissues 48 hours after treatment with either $^{89}$Zr-DFO-labeled exosomes (Control) or unlabeled exosomes followed by $^{89}$Zr-DFO-labeled exosomes (Blocked). $^{89}$Zr-DFO levels are shown as percent of total injected dose. The chart at right shows the same data replotted after removing kidney and spleen levels.

The two cohorts of treated mice were imaged 4 hours, 24 hours, and 48 hours after treatment. Whole body PET/CT imaging revealed robust delivery to the livers of all mice analyzed (FIGS. 1 and 2). Organs were dissected and analyzed by radiographic gamma counter, which revealed a marked increase in exosome uptake by nearly all tissues in mice that were pre-treated with unlabeled exosomes (FIGS. 3 and 4). Notably, exosomes were taken up to a much greater extent by lung, small intestine, large intestine, stomach and pancreas when mice were pre-treated with unlabeled exosomes (FIGS. 3 and 4). These results demonstrate that an in vivo bolus dose of exosomes facilitates bypass of liver and spleen, and allows for an increased uptake of downstream tissues.

Example 2: Administration of Unlabeled, Non-Therapeutic Exosomes Prior to Labeled Exosomes in Mice to Determine Localization to Endothelium and Delivery of RNA The exosome populations are intravenously administered to mice via tail-vein injections using a syringe. Unlabeled exosomes are diluted to a density of 10$^6$ exosomes/ml and DiI-C16-labeled exosomes harboring Cy3-labeled GAPDH siRNA are diluted to a density of 10' exosomes/ml using standard saline buffer at 37° C. such that 1 ml of volume, are delivered per tail vein injection. The exosome solutions are loaded into a 5 cc syringe, 26 gauge needle and injected into the subject through the tail vein.

At 8 weeks of age, mice received tail-vein injections of unlabeled exosomes and DiI-C16-labeled exosomes harboring Cy3-labeled GAPDH siRNA or DiI-C16-labeled exosomes harboring Cy3-labeled GAPDH siRNA alone. 1 mL or 106 exosomes of unlabeled exosomes are injected 15, 30 or 60 minutes prior to injection of 1 mL or 105 exosomes of DiI-C16-labeled exosomes harboring Cy3-labeled GAPDH siRNA. 6, 12 or 24 hours after injection of the DiI-C16-labeled exosomes harboring Cy3-labeled GAPDH siRNA, murine thoracic aorta endothelium is isolated, washed with PBS five times to remove contaminated exosomes, and then viewed under fluorescence microscopy. For measurement of GAPDH RNA levels, total RNA is extracted from thoracic aorta by using TRIzol Reagent (Invitrogen) according to the manufacturer's instructions. RNA samples are then subjected to TaqMan miRNA assays and real-time PCR.

Example 3: Administration of Exosomes Containing Let-7a miRNA in a Human Tumor Xenograft Model for Tracking Tissue Distribution of Exosomes and Tumor Growth Platelets are Transfected with Synthetic Let-7a. Fluorescently-Labeled Exosomes containing Let-7a, and exosomes from untransfected platelets are purified from culture supernatants according to methods described above. Luciferase-expressing HCC70 cells (2×106) are injected subcutaneously into the mammary fat pads of 5-week-old RAG2$^{-/-}$ mice. Four weeks after transplantation, tumors were sized using an IVIS (Xenogen, Hopkinton, MA). Experimental mice with mammary fat pad transplanted luciferase-expressing HCC70 cells are intravenously injected with 150 μg of purified exosomes lacking Let-7a, and after 60 minutes, 150 μg of purified fluorescently-labeled exosomes expressing Let-7a are administered intravenously. Control mice with mammary fat pad transplanted luciferase-expressing HCC70 cells are intravenously injected with saline, and after 60 minutes, 150 μg of purified fluorescently-labeled exosomes expressing Let-7a are administered intravenously. Administration of either purified exosomes lacking Let-7a followed by administration of purified exosomes expressing Let-7a for experimental mice and administration of saline, followed by administration of 150 μg of purified exosomes expressing Let-7a for control mice is performed thrice per week for 4 weeks. Let-7a levels in the exosome samples are evaluated using TaqMan miRNA assays and real-time PCRs. Mice are handled according to the Ethical Guidelines of our institution. Tumor size is monitored every other day using an IVIS. Five weeks post-administration of the first dose of exosomes, mice are euthanized and mammary tumor samples are subjected to immunohistochemistry, TaqMan miRNA assays and real-time PCR.

In Vivo Imaging of Xenograft Tumors

Mice are anesthetized via isoflurane inhalation, and intraperitoneally injected with 100 μl of 7.5 mg/ml luciferin solution (Promega). Bioluminescence imaging is initiated with an IVIS (Xenogen) 10 minutes post injection. The region of interest was defined manually, and bioluminescence data are expressed as photon flux values (photons/s/cm2/steradian). Background photon flux is defined using an area of the tumor that did not receive an intraperitoneal injection of luciferin. All bioluminescence data is collected and analyzed using an IVIS.

In Vivo Imaging of Fluorescently Labeled Exosomes

A stock solution of the lipophilic near-infrared dye Xeno-Light DiR (Caliper Life Sciences, Hopkinton, MA) is prepared in ethanol. A 300-μmol/l working solution is prepared in diluent-C solution (Sigma-Aldrich). Exosomes isolated from culture supernatant-derived platelets are incubated with 2 μmol/l DiR for 30 minutes. The exosomes are then washed with 10 ml of phosphate-buffered saline, subjected to ultracentrifugation, and injected intravenously into RAG2P mice (4 μg of exosomes/mouse). Migration of fluorescently labeled exosomes in murine organs is detected using an IVIS 24 hours post injection.

Example 4: Targeting Exosomes to the Brain In Vivo

Exosomes are engineered by modifying a parent cell with a receiver that targets the complex to a specific tissue for payload delivery. In this example, a parent cell is transfected with a receiver comprising a membrane protein linked to a neuron-specific peptide, which targets isolated exosomes (generated by the parent cell) to the brain tissue. Recipient neurons specifically receive a functional RNA payload (either BACE1 siRNAs or GAPDH siRNA) that is contacted with the exosome prior to administration.

Exosomes with encapsulated siRNA are prepared by electroporation of 150 g of Cy3-labeled scrambled siRNA or 150 g each of two Cy3-labeled BACE1 siRNAs. siRNA-transfection reagent complexes are prepared with cationic liposome-based in vivo transfection reagent as per manufacturer's protocol (Altogen Biosystems). Exosomes for in vivo experiments are spun down and resuspended in 80 μl of 5% glucose immediately before tail vein injection. 150 μg of exosomes with encapsulated 150 μg of Cy3-labeled scrambled siRNA or 150 g of exosomes with encapsulated Cy3-labeled BACE1 siRNAs are injected per animal.

Alternatively, animals are injected with exosomes lacking Cy3-labeled GAPDH siRNA and exosomes harboring Cy3-labeled GAPDH siRNA, or injected with exosomes harboring Cy3-labeled GAPDH siRNA only. For the experimental cohort, receiving both exosomes lacking Cy3-labeled GAPDH siRNA and exosomes harboring Cy3-labeled GAPDH siRNA, 150 g of exosomes lacking Cy3-labeled GAPDH siRNA is injected between 5 minutes and 2 hours prior to injection of 150 g exosomes harboring Cy3-labeled GAPDH siRNA. The control cohort, receiving only the exosomes harboring Cy3-labeled GAPDH siRNA, is injected with saline (at the same volume as the exosome injections) 5 minutes to 2 hours prior to injection of 150 g of the exosomes. Animals of both cohorts are euthanized 12 h later for immunohistochemical analysis of brain tissue sections.

Immunohistochemistry

Brain coronal sections (10 μM) are cut with a cryostat for the histopathological assessment. Slices are washed with PBS and fixed with 4% paraformaldehyde. Slices are treated with blocking solution (PBS containing 10% NGS and 0.05% Triton X-100). Slices are incubated overnight at 4° C. with the primary antibodies: mouse anti-BACE1 (Sigma), mouse anti-GAPDH (1:250, Abcam); mouse anti-NeuN (1:100, Sigma), rabbit anti-glial fibrillary acidic protein (GFAP) (1:250, Sigma), rabbit anti-Iba1 (1:250, Dakocytomation), rabbit anti-OP1 (1:250, Abeam) and rabbit anti-oligodendrocyte specific protein (OSP) (1:205, Abcam). Slices are washed three times with PBS and were incubated with a secondary antibody of the appropriate species; Alexa 488 goat anti-mouse (1:200) and Alexa 488 goat anti-rabbit. The microscope analyses are performed using an epifluorescence microscope (Zeiss).

5' Rapid Amplification of cDNA Ends

RNA is harvested from cortical sections of the brain of mice injected with BACE1 siRNAs encapsulated in exosomes, as mentioned previously. 5' RACE is performed with Invitrogen GeneRacer kit as per manufacturer's instruction on 10 μg of total RNA. Briefly, an RNA linker (5'-CGA-CUGGAGCACGAGGACACUGACAUGGACUGAAGG-AGUAGAAA-3') is ligated to the unprotected phosphorylated 5' end of RNA and the product is reverse transcribed using a specific primer against BACE1 (5'-CGACAAGAG-CATTGTGGACAGTGGGAC-3') using New England Biolabs ThermoPol Taq polymerase. Using a specific primer for the 5' linker and the specific BACE1 primer, the cDNA is amplified and TA-cloned into a vector and sequenced.

Example 5: Administration of Non-Therapeutic Exosomes Prior to Therapeutic Exosomes to Human Patients for the Treatment of Breast Cancer Exosome populations are intravenously administered via a syringe. The exosomes are formulated as described above. Non-therapeutic exosomes and therapeutic exosomes harboring Let-7 miRNA are diluted to a density of 10^7 exosomes/ml using standard saline buffer at 37° C. such that 100 ml of volume, or 10' cells, are delivered. Breast cancer patients are administered 150 g of purified, non-therapeutic exosomes lacking Let-7a, and after 60 minutes, 150 g of purified therapeutic exosomes harboring Let-7a are administered intravenously. Exosome formulations are prepared as described above. The exosome solutions are loaded into a 150 cc syringe, 20 gauge needle and injected into the patient through the basilic vein at 5 cc/min. During injection, the patient's vitals are monitored for any immunogenic or clotting reactions. Administration of 150 ag purified exosomes lacking Let-7a followed by administration of 150 μg purified exosomes expressing Let-7a is performed thrice per week for 12 weeks. Patients are monitored for tumor size and disease progression at 6-weeks and 12-weeks by Positron Emission Tomography and Computed Tomography (PET-CT) imaging.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE 3

| Exosome Lipids | |
| --- | --- |
| Lysobisphosphatidic acid | Ganglioside GM3 24:1 |
| Sphingomyelin (SM) | Ganglioside GM3 16:0 |
| Ganglioside GM3 | PE40:5 |
| Phosphatidylserine (PS) | PE40:6 |
| Phosphatidylinositol (PI) | PE38:3 |
| Phosphatidylcholine (PC) | PE38:4 |
| Phosphatidylethanolamine (PE) | PE36:1 |
| Lysophosphatidylcholine (LPC) | PE36:2 |
| Cholesterol (Chol) | PE34:1 |
| Diacylglycerol (DG) | PE34:2 |
| PI18:0/20:3 | PE-ether38:5 |
| PI18:0/20:4 | PE-ether38:6 |
| PI18:0/18:1 | PE-ether34:1 |
| PI18:1/18:1 | PE-ether34:2 |
| PI18:0/16:0 | PC34:1 |
| PA18:0/18:1 | PC36:4 |
| PS18:0/18:1 | PC34:3 |
| BMP18:0/18:1 | PC32:0 |
| BMP18:1/18:1 | PC30:0 |
| BMP18:1/16:0 | SM24:1 |
| CL(18:1)3/16:1 | SM16:0 |
| CL(18:1)2/(16:1)2 | Dihydrosphingomyelin16:0 |

TABLE 4

| Exosome polypeptides | | | |
| --- | --- | --- | --- |
| ACLY | TCP1 | ACTR1A | LY75 |
| ACTB | PRDX2 | THOC4 | ABCC1 |
| ACTG1 | TSPAN6 | INADL | MYO1E |
| ALB | CCT3 | CTDSPL | NACA |
| ALDOA | TSTA3 | ZMPSTE24 | NAP1L4 |

TABLE 4-continued

Exosome polypeptides

| | | | |
|---|---|---|---|
| ALDOB | TUBA3C | DNAJA2 | NCL |
| AKR1B1 | HIST1H2AK | NDRG1 | NEDD8 |
| AMBP | HIST1H2AJ | RAPGEF3 | YBX1 |
| ANPEP | HIST1H2AB | SPON2 | PA2G4 |
| ANXA2 | HIST2H2AC | UBAC1 | PECAM1 |
| ANXA3 | IFITM1 | N4BP2L2 | PFAS |
| ANXA4 | PDXK | CAP1 | SERPINB9 |
| ANXA5 | LIN7A | VAT1 | PI4KA |
| ANXA6 | BUB3 | NEBL | PLAT |
| ANXA7 | MAP4K4 | DCTN2 | PLCG2 |
| ANXA11 | EDIL3 | ARPC1A | PPA1 |
| ATP1A1 | ATP6AP2 | C6orf108 | PPP2CA |
| CAPZB | PSME3 | SMC2 | PRKCB |
| CD63 | TUBB3 | AHSA1 | PSMA6 |
| CD81 | IFITM3 | STAMBP | PSMA7 |
| CKB | ACAA2 | PMVK | PSMB8 |
| CLU | CCT7 | GIPC1 | PSMB9 |
| CLIC1 | CCT4 | HBS1L | PSMD7 |
| TPP1 | IFITM2 | NCKAP1 | PSME1 |
| CLTC | GNA13 | ALDH1L1 | PTPRA |
| CNP | RUVBL2 | FTCD | RAC2 |
| COL6A1 | PRSS23 | FGL2 | RPL3 |
| CR1 | ACOT7 | CFHR3 | RPL4 |
| CTNND1 | CCT5 | MMP24 | RPL5 |
| ACE | DIP2C | COPS8 | RPL11 |
| DDT | ASCC3L1 | CKAP4 | RPL22 |
| DEFA1 | TNIK | C10orf116 | RPL24 |
| DEFA3 | NEDD4L | SLC27A2 | RPL27 |
| DNAH8 | NCSTN | MID2 | RPL30 |
| DPEP1 | TSPAN15 | KIF3A | RPL28 |
| DPP4 | PLXNB2 | NUDT5 | RPL31 |
| EEF1A1 | SDCBP2 | TREH | RPL34 |
| EEF2 | IGKV1-5 | CEP250 | RPL35A |
| EGF | IGHV4-31 | PDCD10 | RPL37A |
| EIF5A | IGKV3-20 | PADI2 | RPS2 |
| ENO1 | IGKV2-24 | PACSIN2 | RPS3A |
| ENO3 | MINK1 | CHP | RPS5 |
| ENPEP | IGK@ | SNF8 | RPS9 |
| STOM | VPS36 | DDX19B | RPS19 |
| EPS25 | DERA | SCN11A | RPS25 |
| FABP3 | GOLGA7 | LYPLA2 | RPS26 |
| FGA | KRT76 | PARK7 | RPS28 |
| MLANA | EIF3EIP | COBLL1 | RPS29 |
| FN1 | LSR | CNKSR2 | RSU1 |
| FTL | TUBA8 | ENPP4 | SARS |
| FUS | RAB4B | RAB3GAP1 | SLAMF1 |
| GAA | SETD4 | AKR7A3 | SLC1A4 |
| GAPDH | TOLLIP | SPEN | SLC2A3 |
| GDI2 | PLEKHB2 | GANAB | SNRPD2 |
| GGT1 | VPS37C | MGRN1 | SPINK1 |
| GLB1 | LIN7C | CUX2 | SPN |
| GLG1 | H2AFJ | DNAJC13 | STK10 |
| GNA11 | CAND1 | ZCCHC11 | STXBP3 |
| GNAI1 | PLSCR3 | PHF15 | TALDO1 |
| GNAI2 | KIAA1199 | KIAA0841 | TNFAIP3 |
| GNAI3 | GNB4 | ARHGEF12 | TPM3 |
| GNAS | MYH14 | COTL1 | TPM4 |
| GNB1 | TSPAN14 | ANGPTL2 | TYK2 |
| GNB2 | NCALD | DDAH2 | VIM |
| GNG7 | REG4 | HEBP2 | WARS |
| SFN | VPS25 | CD2AP | WAS |
| GPI | TUBB6 | PLD3 | LAT2 |
| GSTA1 | TUBA1C | TMEM2 | HIST1H2BL |
| GSTA2 | TNKS1BP1 | SH3BP4 | STX7 |
| GSTA3 | FAM125B | BHMT2 | CPNE1 |
| GSTM3 | LRSAM1 | GCA | RPL14 |
| GSTP1 | HIST3H2A | MXRA5 | PDCD5 |
| GUSB | TUBA3E | AHCTF1 | SYNGR2 |
| HIST1H2AD | TUBA3D | PTPN23 | RPL23 |
| HLA-A | DCD | DAK | RAB9A |
| HLA-B | HIST4H4 | ACOT11 | IGSF2 |
| HLA-DQB1 | ALDH16A1 | APPL1 | EEF1E1 |
| HLA-DRA | RPS4Y2 | PHGDH | SCAMP2 |
| HLA-DRB1 | MYL6B | TIAM2 | SCAMP3 |
| HLA-DRB5 | BRI3BP | KCNG2 | DPP3 |
| HPGD | AGR3 | CYFIP2 | ARPC1B |
| HRAS | EEF1AL3 | GHITM | PDIA6 |
| HSPA1A | KRT28 | C11orf54 | WASF2 |

| | | | |
|---|---|---|---|
| HSPA1B | KRT24 | DBNL | ANP32B |
| HSPA8 | RPLP0-like | ATAD2 | PAICS |
| HSP90AA1 | RPSAP15 | PHPT1 | AHCYL1 |
| ITGA4 | RANP1 | C16orf80 | VAMP5 |
| KRT1 | PCSK9 | OLA1 | 41891 |
| KRT9 | METRNL | ZDHHC1 | HSPH1 |
| KRT10 | LOC284889 | SNX12 | SUB1 |
| LDHA | KRT6C | PSAT1 | CDC37 |
| LDHB | KRT79 | NT5C | CORO1A |
| TACSTD1 | RAB43 | EHD2 | CD300A |
| MCAM | KRT27 | TAX1BP3 | TMC6 |
| MDH1 | ACTBL2 | CRNN | RFTN1 |
| MEP1A | RP11-631M21.2 | NOX3 | SCRIB |
| MSN | TUBB2B | ATP6V0A4 | SERBP1 |
| 2-Sep | KRT77 | ITSN2 | TTLL3 |
| PGAM1 | AGRN | GEMIN4 | CACYBP |
| PGK1 | RAB15 | LAP3 | SIT1 |
| PKM2 | LOC388524 | CRYL1 | SLC43A3 |
| PPP1CA | LOC388520 | MYO15A | PILRA |
| PTGFRN | HSP90AB2P | ATP6V1D | RPL26L1 |
| PTPRC | ACTBL3 | SNX9 | MPP6 |
| RAN | LOC442497 | PCYOX1 | GNG2 |
| RDX | A26C1A | ANKFY1 | TMED9 |
| SDCBP | HIST2H4B | UFC1 | DOCK10 |
| STX3 | hCG_1757335 | FAM49B | C3orf10 |
| STXBP1 | HLA-A29.1 | CUTA | MYO1G |
| STXBP2 | LOC653269 | ATP6V1H | FLJ21438 |
| TPI1 | A26C1B | VPS24 | SLC38A1 |
| EZR | LOC100128936 | CMPK1 | FERMT3 |
| YWHAE | LOC100130553 | UPB1 | ITFG3 |
| TUBA1A | LOC100133382 | CLIC5 | HIST1H2AH |
| WDR1 | LOC100133739 | MUPCDH | SLAMF6 |
| PDCD6IP | AP2A2 | CLIC6 | TMC8 |
| GPA33 | ALDH3B1 | SIAE | LOC153364 |
| TUBA1B | FASLG | CPVL | SVIP |
| TUBB2C | ATP4A | RHOF | TMEM189-UBE2V1 |
| CAPN7 | CAPS | ARL15 | hCG_16001 |
| DDAH1 | COL12A1 | ZNHIT6 | FABP5L7 |
| PGLS | DMBT1 | GIPC2 | Del(X)1Brd |
| SAMM50 | DSP | PCDH24 | ABP1 |
| CLIC4 | EGFR | VPS13C | ACTN3 |
| CHMP2B | EPHA5 | CC2D1A | AFM |
| ULK3 | EPHB1 | EPS8L1 | AKT1 |
| RNF11 | FAT | C10orf18 | ALDH3A2 |
| VPS4A | HSD17B4 | CHCHD3 | ALOX12P2 |
| ARFIP1 | L1CAM | C2orf18 | ANXA2P1 |
| CHMP2A | LAMA5 | C17orf80 | KRT3 |
| SMPDL3B | MUC4 | EPN3 | MYOC |
| PACSIN3 | NOTCH1 | UACA | SERPINE1 |
| EHD4 | PPP2R1B | VPS13D | PIK3CA |
| EHD3 | PTPRF | APPL2 | NRP1 |
| HEBP1 | SORT1 | ARL8B | SPRY1 |
| VPS28 | SERPINB3 | DDX19A | EMILIN1 |
| DCXR | SELP | NAGK | LRG1 |
| RHCG | FSCN1 | ITLN1 | AZGP1P1 |
| CHMP5 | TGFB1 | CCDC132 | LOC728533 |
| VTA1 | CLTCL1 | OTUB1 | ALDH7A1 |
| RAB14 | CHST1 | CDK5RAP2 | AXL |
| GPRC5B | EIF3I | MBD5 | CFB |
| CAB39 | TNFSF10 | SLC22A11 | CIS |
| RAB8B | MAP7 | SUSD2 | CAT |
| TM7SF3 | COPB2 | SUCNR1 | CD47 |
| MXRA8 | HEPH | BDH2 | CD151 |
| C11orf59 | BASP1 | NIT2 | CDH13 |
| MOBKL1B | CIB1 | RPL23AP13 | CFTR |
| UEVLD | SLC34A2 | FAM20C | CEACAM8 |
| TSNAXIP1 | SLC6A14 | SLC12A9 | AP1S1 |
| GPRC5C | DIP2A | RAB25 | CLTA |
| GNG12 | TNPO3 | SMURF1 | CNGB1 |
| BAIAP2L1 | FER1L3 | TMEM27 | COL1A1 |
| MUC13 | CNTLN | RAB22A | COL1A2 |
| CHMP1B | TUBB4Q | NDRG3 | COL2A1 |
| SLC44A2 | KIF15 | ERMN | COL3A1 |
| CPNE5 | SERINC1 | TAOK1 | COL4A1 |
| TMBIM1 | PDIA2 | KIAA1529 | COL4A2 |
| EPS8L3 | EPS8L2 | RNF213 | COL4A3 |
| MMRN2 | PLVAP | WIZ | COL5A1 |

TABLE 4-continued

| Exosome polypeptides | | | |
|---|---|---|---|
| TTYH3 | MYADM | ACE2 | COL5A2 |
| SLC44A4 | MUC16 | PLEKHA1 | COL7A1 |
| RAB1B | KRT25 | SCPEP1 | COMP |
| RAB33B | SERINC5 | AASDHPPT | CPS1 |
| RBP5 | LOC440264 | FIGNL1 | CSF1 |
| C5orf32 | AGT | PBLD | VCAN |
| ABHD14B | ALPP | KIF9 | SLC25A10 |
| MOBKL1A | APOA2 | LEPRE1 | CTBP2 |
| ARRDC1 | APOB | RAB17 | CTNNA2 |
| IGSF8 | APOE | IKZF5 | DCTN1 |
| FAM125A | SERPING1 | MMP25 | DECR1 |
| SNX18 | C1QB | MPP5 | DNASE1L1 |
| CHMP4B | C1R | TEKT3 | ENG |
| MITD1 | C4A | ALDH8A1 | STX2 |
| S100A16 | C4B | SLC13A3 | ETFB |
| CPNE8 | C4BPA | DUSP26 | F2R |
| C1orf58 | C4BPB | GGCT | F8 |
| GLIPR2 | CD5L | TMEM38A | ACSL1 |
| TUBB | FCN1 | C1orf116 | FAP |
| ATP6V1C2 | FCN2 | GDPD3 | FBLN1 |
| FTLL1 | FGB | OR2A4 | FBN1 |
| PEF1 | FGG | FAM65A | FBN2 |
| SERPINA3 | GRIN1 | NARG1L | FEN1 |
| ACP2 | MSH6 | CHMP6 | FLT1 |
| ACPP | HBA1 | DYNC2H1 | FUCA2 |
| ACTA2 | HBA2 | PRKRIPI | GAS6 |
| ACTC1 | ITGA2B | GSTCD | GDI1 |
| ACTG2 | PPARG | PIP4K2C | GLDC |
| ACY1 | PDLIM7 | CYBRD1 | GNAL |
| APCS | CD274 | FUZ | GRM2 |
| APOD | A1BG | ARMC9 | GRM3 |
| APRT | ACAT1 | NAT13 | GRM7 |
| AQP1 | ACO1 | COASY | GSTM1 |
| AQP2 | ADCY1 | UBXN6 | GSTM5 |
| ARF1 | ADFP | COL18A1 | H2AFX |
| ARF3 | ADH5 | BHLHB9 | HBE1 |
| ARF4 | ADH6 | WNT5B | HMGCS2 |
| ARF5 | PARP4 | CAB39L | TNC |
| ARF6 | AHSG | ITM2C | IDH3B |
| RHOA | AK1 | LOC81691 | IFRD1 |
| ARL3 | ALAD | AMN | ITGA5 |
| ASAH1 | ALCAM | SH3BGRL3 | ITGB5 |
| ASS1 | ALDH2 | C9orf58 | ITPR2 |
| FXYD2 | ALDH9A1 | BCL2L12 | KRT84 |
| BHMT | ALDOC | RAB34 | LAMB1 |
| BST2 | ALK | TBC1D10A | LCN1 |
| C3 | ALOX12 | GPR98 | LGALS8 |
| CA2 | ALPL | HDHD2 | LMNA |
| CA4 | ANXA13 | ARL6 | LOXL2 |
| CALB1 | AOX1 | IQCG | LTBP2 |
| CALR | APAF1 | C2orf16 | MAP1A |
| CD9 | APOA4 | PARD6B | MAT1A |
| CD59 | SHROOM2 | TXNDC17 | MC1R |
| HSPA5 | RHOB | ABCC11 | MCC |
| HSPA6 | ARHGAP1 | FAM40A | ME1 |
| HSP90AB1 | ARHGDIB | SCIN | MECP2 |
| HSPD1 | ARSE | SCRN2 | MAP3K1 |
| IDH1 | ARSF | ZNF486 | MFAP4 |
| KNG1 | ASL | ACY3 | SCGB2A1 |
| KRAS | ASNA1 | C11orf52 | ALDH6A1 |
| LAMP1 | ATIC | CRB3 | MOS |
| LGALS3BP | ATP6V1A | C20orf114 | CITED1 |
| LRP2 | ATP6V1B1 | NAPRT1 | NEFH |
| MAN1A1 | ATP6V1B2 | RG9MTD2 | OPRM1 |
| RAB8A | ATP6V0C | SAT2 | OTC |
| MIF | ATP6V1C1 | KIF12 | OXTR |
| MME | ATP6V1E1 | MAL2 | PAPPA |
| MUC1 | ATP6V0A1 | OSBPL1A | PC |
| MYH9 | ATP6AP1 | VASN | PCOLCE |
| NAGLU | AZU1 | SLC22A12 | PDGFRB |
| NONO | BCR | ACSM1 | PFKFB3 |
| NPM1 | BGN | TTC18 | PGAM2 |
| NRAS | BLMH | GSTO2 | SERPINE2 |
| P2RX4 | BLVRA | CLRN3 | PLP2 |
| P4HB | BLVRB | LRRK2 | PPP1CC |
| PEBP1 | BPI | C12orf59 | SRGN |
| SERPINA5 | BTG1 | LOC124220 | MAP2K6 |
| PFN1 | BTN1A1 | SLC5A10 | PSMB7 |

TABLE 4-continued

| Exosome polypeptides | | | | |
|---|---|---|---|---|
| PFN2 | | TSPO | CCDC105 | PSMB10 |
| ABCB1 | | C1QC | C1orf93 | PTK7 |
| SERPINA1 | | CAPN5 | ARL8A | PTPRK |
| PIGR | | C5 | LOC128192 | PZP |
| PIK3C2B | | C9 | GALM | RAD21 |
| PKD1 | | PTTG1IP | LRRC15 | RASA1 |
| PLSCR1 | | CACNA2D1 | LOC131691 | RDH5 |
| PODXL | | CALML3 | HIFOO | RPL18 |
| CTSA | | CAMK4 | ENPP6 | RPL29 |
| PPIA | | CAMP | CMBL | RPS10 |
| PSAP | | CAPG | MUM1L1 | RPS24 |
| PSMB3 | | CAPN1 | C20orf117 | S100A13 |
| PTBP1 | | CAPN2 | SIRPA | SAA4 |
| PTPRJ | | CAPZA2 | PLEKHA7 | ATXN1 |
| RAB1A | | CD14 | A2ML1 | CLEC11A |
| RAB2A | | CD80 | C16orf89 | SDC2 |
| RAB3B | | CD36 | TOM1L2 | SMARCA4 |
| RAB5A | | SCARB2 | KIF18B | SPOCK1 |
| RAB5B | | CD40 | C19orf18 | STAT1 |
| RAB13 | | CDC2 | PM20D1 | STC1 |
| RAB27B | | CEL | PROM2 | SURF4 |
| RAB5C | | CETP | GPR155 | SYT1 |
| RAC1 | | CTSC | SLC36A2 | TAGLN |
| RALB | | AP2M1 | VPS37D | TCN1 |
| RAP1B | | CSN1S1 | SLC5A12 | TERF1 |
| RBM3 | | CSN2 | SLC5A8 | TGFB2 |
| RNASE2 | | CSN3 | EML5 | TSPAN4 |
| S100A6 | | ACSL3 | TBC1D21 | TSN |
| S100A11 | | FOLR1 | ZNF114 | TSNAX |
| S100P | | B4GALT1 | ANO6 | COL14A1 |
| SLC1A1 | | GNAQ | SLC5A9 | WNT5A |
| SLC2A5 | | HBB | CRTC2 | ZNF134 |
| SLC12A1 | | HBD | C20orf106 | PXDN |
| SLC12A3 | | CFH | TMEM192 | SMC1A |
| SNCG | | HLA-G | ARMC3 | OFD1 |
| SNRPD1 | | HP | NAPEPLD | COPS3 |
| SOD1 | | HPR | C10orf30 | STC2 |
| SRI | | IGHA1 | ATP6V0D2 | ADAM9 |
| TF | | IGJ | STXBP4 | CREG1 |
| THBS1 | | IGLC1 | C17orf61 | CDK5R2 |
| THY1 | | IGLC2 | TXNDC8 | TNFSF18 |
| TMPRSS2 | | IGLC3 | LRRC57 | MPZL1 |
| TSG101 | | LAMC1 | HSPA12A | SEMA5A |
| TUBB2A | | LPA | MAGI3 | CLDN1 |
| UBE2N | | LPL | C11orf47 | RGN |
| UMOD | | LRP1 | SLC39A5 | SLC16A3 |
| UPK2 | | LTF | C12orf51 | ARHGEF1 |
| VTN | | TACSTD2 | SLC46A3 | LRRFIP2 |
| EIF4H | | MBL2 | VMO1 | TAAR2 |
| YWHAB | | MYH8 | SLC26A11 | CRIPT |
| YWHAG | | NEB | LOC284422 | ENTPD4 |
| YWHAZ | | PON1 | CRB2 | IFT140 |
| NPHS2 | | PKN2 | HIST2H2AB | RNF40 |
| RAB7A | | PROS1 | FAM151A | RB1CC1 |
| PSCA | | MASP1 | SLC6A19 | PSMD6 |
| CUBN | | RELN | PKD1L3 | MRC2 |
| BBOX1 | | PTX3 | LOC342897 | HDAC5 |
| RAB11A | | RARS | EGFL11 | RASA4 |
| NAPA | | SILV | SERINC2 | SLC25A13 |
| PROM1 | | THBS2 | PDDC1 | PSMD14 |
| FCGBP | | TLR2 | SLCO4C1 | TFG |
| CPNE3 | | TTN | SFT2D2 | CDIPT |
| MGAM | | TTR | C9orf169 | CRTAP |
| GPRC5A | | TYRP1 | LOC377711 | UNC13B |
| RAB11B | | VWF | OR11L1 | ARL6IP5 |
| VAMP3 | | CLIP2 | RAB19 | TGOLN2 |
| SLC9A3R1 | | XDH | LOC440335 | POSTN |
| ITM2B | | APOL1 | HIST2H2BF | CLPX |
| NAPSA | | FCN3 | LOC441241 | TSPAN9 |
| VPS4B | | SELENBP1 | KPRP | TMED10 |
| RAB3D | | SMC3 | HSP90AB6P | SLC38A3 |
| PRDX6 | | DDX21 | LOC643751 | IL1RAPL1 |
| KIAA0174 | | CCPG1 | LOC651536 | GALNT5 |
| PDCD6 | | ABCG2 | LOC652968 | PRR4 |
| ARPC4 | | SFI1 | AEBP1 | ITGA11 |
| TSPAN1 | | MVP | AMY1A | CLASP2 |
| PDZK1IP1 | | AKAP9 | AMY1B | EPB41L3 |
| NUTF2 | | PRG4 | AMY1C | KIAA0467 |

TABLE 4-continued

Exosome polypeptides

| | | | |
|---|---|---|---|
| FLOT1 | AKRIA1 | AMY2A | DULLARD |
| HRSP12 | ABCA7 | ANGPT1 | NOMO1 |
| A2M | COLEC10 | APLP2 | KIAA0146 |
| ACP1 | GNB5 | APP | SLC39A14 |
| ACTA1 | MMRN1 | AQP5 | DNPEP |
| ACTN4 | CLASP1 | AZGP1 | CASP1 |
| ACTN1 | SYNE1 | CEACAM1 | STX12 |
| ACTN2 | NIPBL | BMP3 | BRMS1 |
| ADAM10 | CHRDL2 | CA6 | ABI3BP |
| AHCY | HSPB8 | DDR1 | PLEKHG3 |
| ALDH1A1 | ANGPTL4 | CAPNS1 | FBXW8 |
| SLC25A4 | NIN | COL6A2 | GAPDHS |
| SLC25A5 | ZNF571 | COPA | GREM1 |
| SLC25A6 | LRP1B | CPD | DKK3 |
| ANXA1 | CNDP2 | DLD | SRPX2 |
| ANXA2P2 | DNAH7 | ETFA | IGHV3-11 |
| APOA1 | HCN3 | GLUD1 | IGHV3-7 |
| ARHGDIA | EXOC4 | HSD17B10 | IGLV4-3 |
| ARVCF | SNX25 | IMPDH2 | IGLV3-21 |
| ATP1A2 | TC2N | HTATIP2 | IGLV1-40 |
| ATP1A3 | HAPLN3 | MARVELD2 | ST6GALNAC6 |
| ATP1B1 | CD163L1 | CST4 | COPS4 |
| ATP5A1 | HRNR | CST5 | HERC5 |
| ATP5B | P704P | CTSB | NUSAP1 |
| ATP5I | CD24 | DAG1 | PLUNC |
| ATP5O | COL6A3 | DSG2 | PPME1 |
| B2M | COL15A1 | TOR1A | MBD3 |
| CALM1 | COMT | ECM1 | SLC38A2 |
| CALM2 | CP | EIF4G1 | FAM64A |
| CALM3 | CPN2 | EXT2 | GTPBP2 |
| CANX | CRABP2 | FAT2 | DIRAS2 |
| CAPZA1 | CRK | GPC4 | DCHS2 |
| CD2 | CRYAB | FOLH1 | QPCTL |
| CD247 | CRYM | FUT2 | PARP16 |
| CD86 | CSE1L | FUT3 | TMEM51 |
| CD37 | CSK | FUT6 | MCM10 |
| CD44 | CSTB | FUT8 | CHST12 |
| CD53 | CTH | GLRX | LYAR |
| CDC42 | CTNS | GPC1 | ODZ3 |
| CDH1 | CTSD | GPX3 | WDR52 |
| CFL1 | CTSG | IGHA2 | ASHIL |
| CFL2 | DDB1 | IGHV@ | UNC45A |
| COX4I1 | DDC | IGL@ | SLC7A10 |
| COX5B | DDX3X | IVL | PNO1 |
| CLDN3 | DDX5 | KRT12 | CD248 |
| CSPG4 | CFD | LAMA4 | AHRR |
| CSRP1 | DNM2 | LAMB2 | ZBTB4 |
| CST3 | DPYS | LGALS7 | SPTBN4 |
| CTNNA1 | DSC2 | LMAN1 | LGR6 |
| CTNNB1 | DSG3 | LPO | RNF123 |
| NQO1 | ECE1 | LTBP3 | PRDM16 |
| DYNC1H1 | MEGF8 | DNAJB9 | PARVG |
| EEF1A2 | ELA2 | MEST | RMND5A |
| EFNB1 | SERPINB1 | MGAT1 | FAT4 |
| CTTN | EPHX2 | MGP | FLJ13197 |
| EPHB4 | FBL | MUC5AC | TREML2 |
| ERBB2 | EVPL | MUC7 | SVEP1 |
| F5 | F11 | NEU1 | OBFC1 |
| FASN | FABP1 | NUCB1 | ZNF614 |
| FKBP1A | ACSL4 | NUCB2 | FLJ22184 |
| FLNA | FAH | FURIN | DBF4B |
| FLNB | EFEMP1 | PAM | CD276 |
| G6PD | FBP1 | PLG | CMIP |
| GCNT2 | FKBP4 | FXYD3 | ADAMTS12 |
| PDIA3 | FKBP5 | PLOD2 | SPACA1 |
| GSN | FRK | PLTP | VANGL1 |
| HADHA | FTH1 | PON3 | SPRY4 |
| HLA-DMB | FUCA1 | PPP1CB | HYI |
| HLA-E | GABRB2 | PRELP | FAM108A1 |
| HNRNPA2B1 | GALK1 | DNAJC3 | TMEM47 |
| HNRNPH2 | GBE1 | HTRA1 | MYCBPAP |
| HSPA1L | GDF2 | RARRES1 | RAB6C |
| HSPA2 | GFRA1 | SAA1 | FAM71F1 |
| HSPA4 | GK2 | SAA2 | ZNF503 |
| HSPA7 | GLO1 | SEPP1 | PARP10 |
| HSPA9 | GLUL | SFRP1 | SHANK3 |
| HSP90AA4P | GM2A | ST3GAL1 | LACRT |
| HSP90AA2 | GNG5 | SLC5A5 | TRIM41 |

TABLE 4-continued

Exosome polypeptides

| | | | |
|---|---|---|---|
| HSP90AB3P | GOT1 | SLC9A1 | OXNAD1 |
| HSPE1 | GPD1 | SLC20A2 | LDHAL6B |
| HSPG2 | GPM6A | SLPI | LOC92755 |
| ICAM1 | GPT | SRPR | CACNA2D4 |
| ITGA6 | GPX4 | STAU1 | ARHGAP18 |
| ITGA2 | GRB2 | HSPA13 | AHNAK2 |
| ITGAV | GRID1 | TGFBI | RPLP0P2 |
| ITGB1 | GSR | TGM1 | PGLYRP2 |
| ITGB2 | GSS | TGM3 | RAB39B |
| ITGB4 | GSTM2 | YES1 | GYLTL1B |
| JUP | HGD | HIST2H2AA3 | KRT74 |
| CD82 | HINT1 | HIST2H2BE | SLAIN1 |
| KPNB1 | HNMT | GALNT4 | LOC122589 |
| KRT2 | HNRNPL | B4GALT3 | NLRP8 |
| KRT5 | HPD | TNFSF13 | PODN |
| KRT8 | HPX | TNFSF12 | C5orf24 |
| KRT13 | HRG | ANGPTL1 | CD109 |
| KRT14 | DNAJA1 | GCNT3 | TRIM40 |
| KRT15 | HSPB1 | TM9SF2 | GPR112 |
| KRT16 | DNAJB1 | DDX23 | KRT72 |
| KRT18 | CFI | ADAMTS3 | VTI1A |
| KRT19 | IGF2R | GPR64 | SYT9 |
| LAMP2 | IGFALS | LHFPL2 | KRT80 |
| LGALS4 | IL1RN | ST3GAL6 | CCDC64B |
| LYZ | IRF6 | PRDX4 | ATP8B3 |
| MARCKS | ITGA1 | MAN1A2 | C1orf84 |
| MFGE8 | EIF6 | OS9 | LOC149501 |
| MMP7 | ITGB8 | MGAT4A | LOC150786 |
| MYH10 | ITIH4 | TWF2 | WDR49 |
| MYL6 | KHK | CLCA4 | NEK10 |
| MYO1C | KIFC3 | TXNDC4 | STOML3 |
| MYO1D | KLK1 | PLCB1 | SASS6 |
| NME1 | LBP | CES3 | DCLK2 |
| NME2 | LCN2 | B3GAT3 | FREM3 |
| PRDX1 | LCP1 | TOR1B | C9orf91 |
| PCBP1 | LTA4H | IGHV3OR16-13 | TREML2P |
| CHMP1A | BCAM | IGLV2-11 | CCDC129 |
| SERPINF1 | MAN2A1 | IGLV1-44 | PAN3 |
| PHB | MDH2 | IGKV3D-15 | MAMDC2 |
| PPIB | MFI2 | IGKV4-1 | RCOR2 |
| PRKAR2A | MLLT3 | C1GALT1C1 | LOC283412 |
| PRKDC | MLLT4 | RACGAP1 | LOC283523 |
| PSMA2 | MNDA | EFEMP2 | NOMO2 |
| QSOX1 | MPO | DUOX2 | SEC14L4 |
| PYGB | MPST | SDF4 | LCN1L1 |
| RAB6A | MYO1B | CYB5R1 | LOC286444 |
| RALA | MSRA | ERAP1 | TAS2R60 |
| RAP1A | MTAP | NUDT9 | KRT18P19 |
| RPL6 | MTHFD1 | FAM3B | LOC343184 |
| RPL8 | MYH3 | FAM20A | LOC345041 |
| RPLP1 | MYO5B | FAM55D | GNAT3 |
| RPLP2 | MYO6 | ANO1 | POLN |
| RPN1 | NID1 | LRRC16A | LOC376693 |
| RPS3 | NKX6-1 | TTC17 | ARMS2 |
| RPS7 | NQO2 | PDGFC | LOC387867 |
| RPS13 | NP | PCDHGB5 | LOC388339 |
| RPS14 | NPC1 | CCL28 | FLG2 |
| RPS15A | NPHS1 | UGCGL1 | LOC388707 |
| RPS18 | NRF1 | SEMA3G | LOC389141 |
| RPS20 | NT5E | CORO1B | LOC390183 |
| RPS21 | PAFAH1B1 | NDRG2 | KRT8P9 |
| RPS27A | PAFAH1B2 | KIAA1324 | LOC391777 |
| RRAS | PCBD1 | TXNDC16 | LOC391833 |
| S100A10 | PCK1 | ARHGAP23 | LOC399942 |
| SDC1 | PDCD2 | MUTED | LOC400389 |
| SDC4 | PDE8A | TINAGL1 | LOC400578 |
| SLC1A5 | ENPP3 | TOR3A | LOC400750 |
| SLC2A1 | SLC26A4 | VWA1 | LOC400963 |
| SLC3A2 | PDZK1 | CHID1 | FLJ21767 |
| SLC12A2 | PEPD | TMEM109 | LOC401817 |
| SLC16A1 | PFKL | GAL3ST4 | NOMO3 |
| SPTBN1 | PGD | THSD4 | LOC439953 |
| SSBP1 | PGM1 | UXS1 | RPL12P6 |
| SSR4 | SLC25A3 | TXNDC5 | LOC440589 |
| TBCA | SERPINA4 | CRISPLD1 | LOC440917 |
| TCEB1 | SERPINB6 | LOXL4 | LOC440991 |
| TFRC | SERPINB13 | GNPTG | LOC441876 |
| TKT | PIK3C2A | SCGB3A1 | LOC442308 |

TABLE 4-continued

| Exosome polypeptides | | | |
|---|---|---|---|
| TSPAN8 | PIP | CHST14 | DIPAS |
| TPM1 | PKD2 | C1QTNF1 | LOC643300 |
| HSP90B1 | PKLR | C1QTNF3 | LOC643358 |
| TUBA4A | PKHD1 | SLC26A9 | LOC643531 |
| TUFM | PLCD1 | FAM129A | RPSAP8 |
| TXN | PLOD1 | HIST2H3C | LOC644464 |
| UBA52 | PLS1 | TPRGIL | LOC644745 |
| UBB | UBL3 | TMPRSS11B | LOC645018 |
| UBC | PPL | C20orf70 | LOC645548 |
| UBA1 | PPP1R7 | PPM1L | LOC646127 |
| UBE2V2 | PRCP | GBP6 | LOC646316 |
| UGDH | PRKCA | KRT78 | LOC646359 |
| UQCRC2 | PRKCD | SLC37A2 | LOC646785 |
| VCP | PRKCH | NPNT | LOC646875 |
| VIL1 | PRKCI | KRT73 | LOC646949 |
| YWHAH | PRKCZ | HIST2H3A | LOC647000 |
| CXCR4 | PRNP | VWA2 | LOC647285 |
| SLC7A5 | PRSS8 | GSTK1 | LOC650405 |
| HIST1H4I | PRTN3 | SBSN | LOC650901 |
| HIST1H4A | PSMA1 | C5orf46 | LOC652493 |
| HIST1H4D | PSMA3 | LRRC26 | LOC652797 |
| HIST1H4F | PSMA4 | C4orf40 | LOC653162 |
| HIST1H4K | PSMA5 | LOC440786 | PPIAL3 |
| HIST1H4J | PSMB1 | SCFV | LOC653232 |
| HIST1H4C | PSMB2 | LGALS7B | HSPBL2 |
| HIST1H4H | PSMB5 | HIST2H3D | LOC728002 |
| HIST1H4B | PSMB6 | ACAT2 | LOC728088 |
| HISTIH4E | PSMC5 | ACTL6A | LOC728576 |
| HIST1H4L | PSMD12 | ADK | LOC728590 |
| HIST2H4A | PSME2 | ANXA8L2 | LOC728791 |
| TAGLN2 | PTPN6 | ATP1B3 | LOC728979 |
| RUVBL1 | PTPN13 | ATP2B1 | ANG |
| VAMP8 | PTPRO | ATP2B4 | BDNF |
| SNAP23 | QDPR | CAV1 | CALU |
| IQGAP1 | RAB27A | CD70 | CCR4 |
| KRT75 | RAPIGDS1 | CS | CCR5 |
| TJP2 | RBL2 | DARS | CSF2 |
| ROCK2 | RBP4 | DHX9 | CSF3 |
| ARPC3 | RENBP | DPYSL2 | DCN |
| ACTR3 | RFC1 | EEF1D | EPO |
| LRPPRC | RHEB | EPRS | F3 |
| TRAP1 | RNH1 | FDPS | GPC5 |
| TUBB4 | RNPEP | FLNC | GDF1 |
| GNB2L1 | ROBO2 | XRCC6 | GDF9 |
| BAIAP2 | RP2 | GFPT1 | GFRA3 |
| HYOU1 | RPS11 | HIST1H1B | GRN |
| AGR2 | RREB1 | HIST1H2BB | CXCL2 |
| OLFM4 | RYR1 | H3F3A | GZMA |
| CCT2 | S100A4 | H3F3B | HIST1H2BD |
| ATP5L | S100A8 | HNRNPF | HGF |
| CCT8 | S100A9 | HNRNPK | IFNG |
| SLC12A7 | SERPINB4 | IARS | IGFBP3 |
| MASP2 | SCN10A | LAMA3 | IGFBP4 |
| IQGAP2 | SEC13 | LAMB3 | IGFBP6 |
| RAB10 | SECTM1 | LAMC2 | IGFBP7 |
| PRDX3 | SH3BGRL | LGALS1 | IL1RAP |
| EHD1 | SHMT1 | NBR1 | IL3 |
| TMED2 | SHMT2 | MARS | IL5 |
| LMAN2 | SLC3A1 | MX1 | IL6ST |
| YWHAQ | SLC4A1 | PFKP | IL7 |
| GCN1L1 | SLC5A1 | PLAU | IL8 |
| RAB35 | SLC5A2 | PSMB4 | IL10 |
| DSTN | SLC6A13 | PSMC2 | IL11 |
| UPK1A | SLC9A3 | PSMC4 | IL13 |
| PHB2 | SLC15A2 | PSMD2 | IL15RA |
| RRAS2 | SLC25A1 | PSMD13 | INHBA |
| SEC31A | SLC22A2 | PYGL | INHBB |
| CLSTN1 | SLC22A5 | RPL10 | IPO5 |
| PTGR1 | SMO | RPL15 | LIF |
| RAB21 | SORD | STX4 | LRP6 |
| CYFIP1 | SORL1 | TARS | LTBP1 |
| SLC44A1 | SPAST | CLDN5 | MMP1 |
| CORO1C | SPR | TPBG | MMP2 |
| MTCH2 | SPRR3 | XPO1 | MMP3 |
| QPCT | SRC | XRCC5 | MMP10 |
| PRDX5 | ST13 | BAT1 | NBL1 |
| SND1 | STK11 | HIST1H2BG | TNFRSF11B |
| F11R | VAMP7 | HIST1H2BF | OSM |

TABLE 4-continued

| Exosome polypeptides | | | |
|---|---|---|---|
| LIMA1 | SYPL1 | HIST1H2BE | PDGFA |
| RAB6B | SERPINA7 | HIST1H2BI | PRKCSH |
| KRT20 | TECTA | HIST1H2BC | CCL2 |
| VPS35 | TGM4 | HIST1H4G | CCL7 |
| TOMM22 | TGFBR3 | EIF3A | CCL20 |
| AKR1B10 | TGM2 | EIF3B | SFRP4 |
| S100A14 | TLN1 | EIF3C | SOD3 |
| DIP2B | DNAJC7 | SLC5A6 | SPARC |
| RAP2C | UBE2G1 | HIST2H2AA4 | TIMP1 |
| FAM129B | UPK1B | LOC728358 | TIMP2 |
| MARCKSL1 | UGP2 | LOC730839 | TIMP3 |
| AHNAK | UPK3A | LOC100126583 | ICAM5 |
| VPS37B | UTRN | AARS | TNFRSF1A |
| TUBA4B | VASP | AK2 | VEGFC |
| ARPC5L | VCL | APEH | GDF5 |
| EPPK1 | VDAC1 | FAS | HIST3H3 |
| ADSL | VDAC3 | BAX | HIST1H2AI |
| AP2A1 | XPNPEP2 | FMNL1 | HIST1H2AL |
| RHOC | BTG2 | CASP9 | HIST1H2AC |
| RHOG | GCS1 | CD19 | HIST1H2AM |
| ASNS | BAT2 | MS4A1 | HIST1H2BN |
| BSG | PTP4A2 | CD22 | HIST1H2BM |
| CAD | DYSF | TNFRSF8 | HIST1H2BH |
| CBR1 | EEA1 | SCARB1 | HIST1H2BO |
| CBR3 | STK24 | ENTPD1 | HIST1H3A |
| CCT6A | CUL4B | CD48 | HIST1H3D |
| CDH17 | CUL3 | CD58 | HIST1H3C |
| CEACAM5 | ATRN | CD74 | HIST1H3E |
| COPB1 | CDC42BPA | CD79B | HIST1H3I |
| CLDN4 | PPFIA2 | CD97 | HIST1H3G |
| CLDN7 | AKR7A2 | 41889 | HIST1H3J |
| CRYZ | PPAP2A | CR2 | HIST1H3H |
| CD55 | ABCB11 | CSNK2B | HIST1H3B |
| EEF1G | MAP2K1IP1 | DBI | FADD |
| EPHA2 | EIF3H | DHCR7 | IL1RL2 |
| EIF4A1 | SLC4A4 | DLG1 | FGF18 |
| EIF4A2 | SNX3 | DOCK2 | FGF16 |
| ENO2 | MYH13 | DUT | HIST1H3F |
| SLC29A1 | NAPG | ECH1 | HIST1H2AG |
| EPHB2 | FBP2 | VAPA | HIST1H2BJ |
| EPHB3 | SCEL | H2AFY | NRG2 |
| ESD | SUCLA2 | PDIA4 | GDF3 |
| F7 | GGH | EIF4A3 | FGF19 |
| FLOT2 | PROZ | ACTR1B | GDF11 |
| GARS | SQSTM1 | OPTN | FST |
| GMDS | AP1M1 | NAMPT | LASS1 |
| GNB3 | RAB7L1 | MPZL2 | HPSE |
| HIST1H2AE | WASL | STIP1 | ESM1 |
| HLA-C | PLOD3 | PKP3 | DKK1 |
| HLA-H | PGLYRP1 | POFUT2 | IL17B |
| HPCAL1 | KALRN | QPRT | IL19 |
| IGSF3 | CLIC3 | WBP2 | TNFRSF12A |
| IGH@ | BAZ1B | ERO1L | IL23A |
| IGHG1 | SPAG9 | H2AFY2 | FGFRL1 |
| IGHG2 | SLC13A2 | RCC2 | TREM1 |
| IGHG3 | ATP6V0D1 | RTN4 | IL1F9 |
| IGHG4 | HGS | GLT25D1 | CXCL16 |
| IGHM | AP4M1 | RNASE7 | IL22RA1 |
| IGKC | ATP6V1F | FCRLA | HIST1H2BK |
| ITGA3 | PTER | H2AFV | HIST3H2BB |
| KRT3 | TRIP10 | MRLC2 | LOC440093 |
| KRT4 | SLC9A3R2 | PAGE2 | PGAM4 |
| KRT6A | SLIT2 | HIST1H2BA | PC-3 |
| KRT6B | SLC22A6 | SNX33 | LOC729500 |
| KRT7 | KL | PTRF | KRT18P26 |
| KRT17 | KIF3B | HIST2H2BC | S100A11P |
| RPSA | SLC22A8 | ANXA8 | LOC729679 |
| LFNG | GRHPR | NME1-NME2 | KRT17P3 |
| LGALS3 | SLC22A13 | EIF2S1 | RCTPI1 |
| LRP4 | TMPRSS11D | EIF2S3 | LOC729903 |
| CD46 | GSTO1 | EIF4E | RP11-556K13.1 |
| MICA | NPEPPS | EPB41L2 | LOC100129982 |
| MYH11 | TMEM59 | EVI2B | LOC100130100 |
| NARS | ATP6V1G1 | FCER2 | LOC100130446 |
| NEDD4 | CDC42BPB | FGR | LOC100130562 |
| RPL10A | CREB5 | FH | LOC100130624 |
| PCNA | CROCC | GART | LOC100130711 |
| PLEC1 | DHX34 | GOT2 | LOC100130819 |

TABLE 4-continued

| Exosome polypeptides | | | |
|---|---|---|---|
| PLXNA1 | TMEM63A | NCKAP1L | LOC100131713 |
| PPP2R1A | SLK | HLA-DPB1 | LOC100131863 |
| PSMC6 | RUSC2 | HLA-DQA1 | LOC100132795 |
| PSMD3 | OXSR1 | HNRNPA1 | LOC100133211 |
| PSMD11 | SLC23A1 | HNRNPC | LOC100133690 |
| RAC3 | DOPEY2 | HPRT1 | SET |
| RAP2A | ABI1 | ICAM3 | CCT6B |
| RAP2B | GNPDA1 | INSR | ACTR3B |
| RPL12 | TOM1 | EIF3E | PSMA8 |

TABLE 4-continued

| Exosome polypeptides | | | |
|---|---|---|---|
| RPLP0 | ABCB6 | ITGAL | ARP11 |
| RPS4X | ABCC9 | ITGB3 | BCHE |
| RPS4Y1 | HUWE1 | ITGB7 | H2AFZ |
| RPS8 | ARPC5 | ITIH2 | SNRPE |
| RPS16 | ACTR2 | STMN1 | TFPI |
| SPTAN1 | TSPAN3 | LCK | ADAMTS1 |
| VAMP1 | ARPC2 | LSP1 | GDF15 |

TABLE 5

| Polypeptide Payloads and Receivers | | | |
|---|---|---|---|
| Ankyrin repeat proteins | Fibronectins | Lyases | |
| General Classes | | | |
| Antibodies | Complement receptors | GPI-linked polypeptides | Nanobodies |
| Aptamers | Cyclic peptides | HEAT repeat proteins | Nucleic Acids |
| ARM repeat proteins | DARPins | Hydrolases | Polypeptides |
| Carbohydrates | DNAses | Kinases | Single-chain variable fragments (scFv) |
| Cell surface receptors | Enzymes | Lipoproteins | Tetratricopeptide repeat proteins |
| Complement | | | |
| C1 inhibitor | C4 binding protein | CR3 | Factor I |
| C3 Beta chain Receptor | CD59 | CR4 | Homologous restriction factor |
| C3aR | CR1 | Decay-accelerating factor (DAF) | Membrane cofactor protein (MCP) |
| C3eR | CR2 | Factor H | PRELP |
| Enzymes | | | |
| triacylglycerol lipase | bile-acid-CoA hydrolase | feruloyl esterase | phosphatidate phosphatase |
| (S)-methylmalonyl-CoA hydrolase | bis(2-ethylhexyl)phthalate esterase | formyl-CoA hydrolase | phosphatidylglycero phosphatase |
| [acyl-carrier-protein] phosphodiesterase | bisphosphoglycerate phosphatase | fructose-bisphosphatase | phosphatidylinositol deacylase |
| [phosphorylase] phosphatase | Carboxylic-Ester Hydrolases | fumarylacetoacetase | phosphodiesterase I |
| 1,4-lactonase | carboxymethylene-butenolidase | fusarinine-C ornithinesterase | phosphoglycerate phosphatase |
| 11-cis-retinyl-palmitate hydrolase | cellulose-polysulfatase | galactolipase | phosphoglycolate phosphatase |
| 1-alkyl-2-acetyl-glycerophospho-choline esterase | cephalosporin-C deacetylase | gluconolactonase | phosphoinositide phospholipase C |
| 2'-hydroxybiphenyl-2-sulfinate desulfinase | cerebroside-sulfatase | glucose-1-phosphatase | phospholipase A1 |
| 2-pyrone-4,6-dicarboxylate lactonase | cetraxate benzylesterase | glucose-6-phosphatase | phospholipase A2 |
| 3',5'-bisphosphate nucleotidase | chlorogenate hydrolase | glutathione thiolesterase | phospholipase C |
| 3-hydroxyisobutyryl-CoA hydrolase | chlorophyllase | glycerol-1-phosphatase | phospholipase D |
| 3'-nucleotidase | cholinesterase | glycerol-2-phosphatase | phosphonoacctaldchyde hydrolase |
| 3-oxoadipate enol-lactonase | choline-sulfatase | glycerophosphocholine phosphodiesterase | phosphonoacetate hydrolase |
| 3-phytase | choloyl-CoA hydrolase | Glycosidases, i.e. enzymes that hydrolyse O- and S-glycosyl compounds | phosphonopyruvate hydrolase |

TABLE 5-continued

| Polypeptide Payloads and Receivers | | | |
|---|---|---|---|
| Ankyrin repeat proteins | | Fibronectins | Lyases |
| 4-hydroxybenzoyl-CoA thioesterase | chondro-4-sulfatase | glycosulfatase | phosphoprotein phosphatase |
| 4-methyloxaloacetate esterase | chondro-6-sulfatase | Glycosylases | Phosphoric-diester hydrolases |
| 4-phytase | citrate-lyase deacetylase | histidinol-phosphatase | Phosphoric-monoester hydrolases |
| 4-pyridoxolactonase | cocaine esterase | hormone-sensitive lipase | Phosphoric-triester hydrolases |
| 5'-nucleotidase | cutinase | Hydrolysing N-glycosyl compounds | phosphoserine phosphatase |
| 6-acetylglucose deacetylase | cyclamate sulfohydrolase | Hydrolysing S-glycosyl compounds | poly(3-hydroxybutyrate) depolymerase |
| 6-phosphogluconolactonase | Cysteine endopeptidases | hydroxyacylglutathione hydrolase | poly(3-hydroxyoctanoate) depolymerase |
| a-amino-acid esterase | Cysteine-type carboxypeptidases | hydroxybutyrate-dimer hydrolase | polyneuridine-aldehyde esterase |
| a-Amino-acyl-peptide hydrolases | D-arabinonolactonase | hydroxymethylglutaryl-CoA hydrolase | protein-glutamate methylesterase |
| acetoacetyl-CoA hydrolase | deoxylimonate A-ring-lactonase | iduronate-2-sulfatase | quorum-quenching N-acyl-homoserine lactonase |
| acetoxybutynyl-bithiophene deacetylase | dGTPase | inositol-phosphate phosphatase | retinyl-palmitate esterase |
| acetylajmaline esterase | dihydrocoumarin hydrolase | juvenile-hormone esterase | Serine dehyrdatase or serine hydroxymethyl transferase |
| acetylalkylglycerol acetylhydrolase | Dipeptidases | kynureninase | Serine endopeptidases |
| acetylcholinesterase | Dipeptide hydrolases | L-arabinonolactonase | serine-ethanolaminephosphate phosphodiesterase |
| acetyl-CoA hydrolase | Dipeptidyl-peptidases and tripeptidyl-peptidases | limonin-D-ring-lactonase | Serine-type carboxypeptidases |
| acetylesterase | Diphosphoric-monoester hydrolases | lipoprotein lipase | S-formylglutathione hydrolase |
| acetylpyruvate hydrolase | disulfoglucosamine-6-sulfatase | L-rhamnono-1,4-lactonase | sialate O-acetylesterase |
| acetylsalicylate deacetylase | dodecanoyl-[acyl-carrier-protein] hydrolase | lysophospholipase | sinapine esterase |
| acetylxylan esterase | Endodeoxyribonucleases producing 3'-phosphomonoesters | mannitol-1-phosphatase | Site specific endodeoxyribonucleases: cleavage is not sequence specific |
| acid phosphatase | Endodeoxyribonucleases producing 5'-phosphomonoesters | Metallocarboxypeptidases | Site-specific endodeoxyribonucleases that are specific for altered bases. |
| Acting on acid anhydrides to catalyse transmembrane movement of substances | Endopeptidases of unknown catalytic mechanism | Metalloendopeptidases. | Site-specific endodeoxyribonucleases: cleavage is sequence specific |
| Acting on acid anhydrides to facilitate cellular and subcellular movement | Endoribonucleases producing 3'-phosphomonoesters | methylphosphothio-glycerate phosphatase | sphingomyelin phosphodiesterase |
| Acting on GTP to facilitate cellular and subcellular movement | Endoribonucleases producing 5'-phosphomonoesters | methylumbelliferyl-acetate deacetylase | S-succinylglutathione hydrolase |
| Acting on phosphorus-nitrogen bonds | Endoribonucleases that are active with either ribo- or deoxyribonucleic acids and produce 3'-phosphomonoesters | monoterpene e-lactone hydrolase | steroid-lactonase |

TABLE 5-continued

| Polypeptide Payloads and Receivers | | | |
| --- | --- | --- | --- |
| Ankyrin repeat proteins | | Fibronectins | Lyases |
| Acting on sulfur-nitrogen bonds | Endoribonucleases that are active with either ribo- or deoxyribonucleic acids and produce 5'-phosphomonoesters | N-acetylgalactosamine-4-sulfatase | sterol esterase |
| actinomycin lactonase | Enzymes acting on acid anhydrides | N-acetylgalactosamine-6-sulfatase | steryl-sulfatase |
| acylcarnitine hydrolase | Enzymes Acting on carbon-carbon bonds | N-acetylgalactosamino-glycan deacetylase | succinyl-CoA hydrolase |
| acyl-CoA hydrolase | Enzymes acting on carbon-nitrogen bonds, other than peptide bonds | N-acetylglucosamine-6-sulfatase | sucrose-phosphate phosphatase |
| acylglycerol lipase | Enzymes acting on carbon-phosphorus bonds | N-sulfoglucosamine sulfohydrolase | sugar-phosphatase |
| acyloxyacyl hydrolase | Enzymes acting on carbon-sulfur bonds | oleoyl-[acyl-carrier-protein] hydrolase | Sulfuric-ester hydrolases |
| acylpyruvate hydrolase | Enzymes Acting on ether bonds | Omega peptidases | tannase |
| ADAMTS13 | Enzymes acting on halide bonds | orsellinate-depside hydrolase | Thioester hydrolases |
| Adenosine deaminase | Enzymes acting on peptide bonds (peptidases) | oxaloacetase | Thioether and trialkylsulfonium hydrolases |
| adenylyl-[glutamate-ammonia ligase] hydrolase | Enzymes acting on phosphorus-nitrogen bonds | palmitoyl[protein] hydrolase | Threonine endopeptidases |
| ADP-dependent medium-chain-acyl-CoA hydrolase | Enzymes acting on sulfur-nitrogen bonds | palmitoyl-CoA hydrolase | thymidine phosphorylase |
| ADP-dependent short-chain-acyl-CoA hydrolase | Enzymes acting on sulfur-sulfur bonds | pectinesterase | trehalose-phosphatase |
| ADP-phosphoglycerate phosphatase | Ether hydrolases. | Peptidyl peptide hydrolases | triacetate-lactonase |
| alkaline phosphatase | Exodeoxyribonucleases producing 5'-phosphomonoesters | Peptidyl-amino-acid hydrolases | Triphosphoric-monoester hydrolases |
| all-trans-retinyl-palmitate hydrolase | Exonucleases that are active with either ribo- or deoxyribonucleic acids and produce 3'-phosphomonoesters | Peptidylamino-acid hydrolases or acylamino-acid hydrolases | trithionate hydrolase |
| aminoacyl-tRNA hydrolase | Exonucleases that are active with either ribo- or deoxyribonucleic acids and produce 5'-phosphomonoesters | Peptidyl-dipeptidases | tropinesterase |
| Aminopeptidases | Exoribonucleases producing 3'-phosphomonoesters | phenylacetyl-CoA hydrolase | ubiquitin thiolesterase |
| arylesterase | Exoribonucleases producing 5'-phosphomonoesters . | Phenylalanine ammonia lyase | UDP-sulfoquinovose synthase |
| arylsulfatase | Factor IX | Phenylalanine hydroxylase | uricase |
| Asparaginase | Factor VIII | pheophorbidase | uronolactonase |
| Aspartic endopeptidases | fatty-acyl-ethyl-ester synthase | phloretin hydrolase | wax-ester hydrolase |
| b-diketone hydrolase | | phorbol-diester hydrolase | xylono-1,4-lactonase |

TABLE 6

| Targets | | | |
|---|---|---|---|
| General Classes of Targets | | | |
| Microbes | Polypeptides | DNA | Amino Acids |
| Fungi | Toxins | RNA | Prions |
| Bacteria | Lipids | Parasites | Cytokines |
| Virus | Cells | Cellular Debris | |
| Infectious Disease-Related Targets | | | |
| Lipopolysaccharides | Cell invasion protein | Intermedilysin | Secreted effector protein sptP |
| Zona occludens toxin | Cholera enterotoxin | Invasion protcin sipA | Sccligcriolysin |
| Actin polymerization protein RickA | Cysteine protease | Iota toxin component Ia | Serine protease |
| Actin polymerization protein RickA | Cytolcthal distonding toxin | Ivanolysin | Shiga toxin |
| Adenosine monophosphate-protein transferase vopS | Cytolysin | LepB | Sphingomyelinase |
| adenylate cyclase | Cytotoxic necrotizing factor | Lethal factor | Staphylokinase |
| Adenylate cyclase ExoY | Cytotoxin | Leukotoxin | Streptokinase |
| ADP-ribosyltransferase enzymatic component | Dermonecrotic toxin | Listeriolysin | Streptolysin |
| Aerolysin | Deubiquitinase | Microbial collagenase | Streptopain |
| Alpha-toxin | Diphtheria toxin | Outer membrane protein IcsA autotransporter | Suilysin |
| Alveolysin | Enterohemolysin | Panton-Valentine Leucocidin F | Superantigen |
| Alveolysin | Enterotoxin | Perfringolysin | T3SS secreted effector EspF |
| Anthrolysin O | Epidermal cell differentiation inhibitor | Pertussis toxin | Tetanus toxin |
| Arp2/3 complex-activating protein rickA | Exoenzyme | Phospholipase | Tir |
| Binary ADP-ribosyltransferase CDT toxin | Exotoxin | Plasminogen activator | TolC |
| Botulinum neurotoxin | G-nucleotide exchange factor | Pneumolysin | Toxic shock syndrome toxin |
| C2 toxin, component II | Guanine nucleotide exchange factor sopE | Protective antigen | Zink-carboxypeptidase |
| CagA | Heat stable enterotoxin | Protein kinase | Zink-carboxypeptidase |
| Calmodulin-sensitive adenylate cyclase | IgA-specific serine endopeptidase autotransporter | Pyolysin | Zn-dependent peptidase |
| Cell cycle inhibiting factor | Inositol phosphate phosphatase sopB | RTX toxin | |
| Lipid & Cell Targets | | | |
| Circulating tumor cells | very low density lipid (VLDL) | triglycerides | Fatty acids |
| Metastases | high density lipoprotein | chylomicrons | Cholesterol |
| Eukaryotic cells | low density lipoprotein | apolipoproteins | |

TABLE 7

| Exosome miRNAs | | | |
|---|---|---|---|
| let-7a | miR-301 | miR-92b | miR-K12-7 |
| let-7b | miR-302a | miR-93 | miR-125b-1* |
| let-7c | miR-30a-3p | miR-95 | miR-US25-2-5p |
| let-7d | miR-30a-5p | miR-96 | miR-373* |
| let-7e | miR-30b | miR-98 | miR-149* |
| let-7f | miR-30c | miR-99a | miR-200a* |

TABLE 7-continued

| Exosome miRNAs | | | |
|---|---|---|---|
| let-7g | miR-30d | miR-99b | miR-513a-5p |
| let-7i | miR-30e-3p | U6-snRNA | miR-575 |
| miR-100 | miR-31 | miR-760 | miR-125a-3p |
| miR-101 | miR-320 | miR-630 | miR-1224-5p |
| miR-103 | miR-324-3p | miR-632 | miR-490-5p |
| miR-105 | miR-324-5p | miR-654-5p | miR-188-5p |

TABLE 7-continued

| Exosome miRNAs | | | |
|---|---|---|---|
| miR-106a | miR-328 | miR-671-5p | miR-1226* |
| miR-106b | miR-331 | miR-US4 | miR-610 |
| miR-107 | miR-335 | miR-K12-3 | miR-877 |
| miR-10a | miR-339 | miR-326 | miR-424* |
| miR-10b | miR-342 | miR-199b-5p | miR-887 |
| miR-122a | miR-345 | miR-502-5p | miR-601 |
| miR-125a | miR-346 | miR-551b | miR-125b-2* |
| miR-125b | miR-34a | miR-92a | miR-513b |
| miR-126 | miR-361 | miR-221* | miR-662 |
| miR-128a | miR-362 | miR-223* | miR-518e* |
| miR-128b | miR-365 | miR-892b | miR-99b* |
| miR-129 | miR-369-3p | miR-K12-12 | miR-520e |
| miR-130a | miR-370 | miR-542-5p | hiv1-miR-H1 |
| miR-130b | miR-371 | let-7i* | miR-617 |
| miR-133a | miR-373 | miR-188-3p | miR-513c |
| miR-135b | miR-375 | miR-155 | miR-10b* |
| miR-136 | miR-421 | miR-340* | miR-135a* |
| miR-137 | miR-422a | miR-132* | miR-1225-5p |
| miR-138 | miR-422b | miR-450a | miR-498 |
| miR-140 | miR-423 | miR-361-3p | miR-BART14 |
| miR-141 | miR-424 | miR-363 | miR-200b* |
| miR-146a | miR-425-3p | miR-501-3p | miR-520b |
| miR-146b | miR-425-5p | miR-195 | miR-134 |
| miR-147 | miR-429 | miR-132 | miR-518c* |
| miR-148a | miR-432 | miR-500* | miR-BART7 |
| miR-148b | miR-452 | miR-22* | miR-491-5p |
| miR-149 | miR-453 | miR-342-3p | miR-382 |
| miR-150 | miR-454-3p | miR-128 | miR-583 |
| miR-151 | miR-454-5p | miR-342-5p | miR-874 |
| miR-152 | miR-483 | miR-362-3p | miR-516b |
| miR-15b | miR-484 | miR-886-3p | miR-518f |
| miR-16 | miR-485-5p | miR-361-5p | miR-622 |
| miR-17-3p | miR-486 | miR-30a | miR-K12-8 |
| miR-17-5p | miR-487b | miR-223 | miR-513a-3p |
| miR-18la | miR-494 | miR-331-3p | miR-UL36 |
| miR-181b | miR-500 | miR-564 | miR-141* |
| miR-181c | miR-502 | miR-425 | miR-492 |
| miR-181d | miR-505 | miR-502-3p | miR-129-5p |
| miR-182 | miR-512-3p | miR-590-5p | miR-30c-2* |
| miR-183 | miR-513 | miR-330-3p | miR-486-5p |
| miR-185 | miR-517c | miR-378 | miR-631 |
| miR-186 | miR-519b | miR-139-3p | miR-184 |
| miR-187 | miR-521 | miR-28-3p | miR-145 |
| miR-188 | miR-522 | miR-32 | miR-628-5p |

TABLE 7-continued

| Exosome miRNAs | | | |
|---|---|---|---|
| miR-18a | miR-526a | miR-301a | miR-BHRF1-1 |
| miR-18b | miR-527 | miR-542-3p | miR-518d-3p |
| miR-190 | miR-532 | miR-34b* | let-7d* |
| miR-191 | miR-550 | miR-17 | miR-93* |
| miR-192 | miR-557 | miR-532-3p | miR-548d-5p |
| miR-193a | miR-565 | miR-140-3p | miR-548c-5p |
| miR-193b | miR-571 | miR-28-5p | miR-770-5p |
| miR-194 | miR-574 | miR-30e* | miR-744* |
| miR-196b | miR-578 | miR-532-5p | miR-449a |
| miR-197 | miR-582 | miR-146b-5p | miR-548a-5p |
| miR-198 | miR-584 | miR-503 | miR-148a* |
| miR-19a | miR-585 | miR-339-3p | miR-624* |
| miR-19b | miR-590 | miR-338-3p | miR-219-5p |
| miR-200a | miR-593 | miR-33a | miR-16-2* |
| miR-200b | miR-594 | miR-374b | miR-29c* |
| miR-200c | miR-595 | miR-30e | miR-550* |
| miR-202 | miR-603 | miR-362-5p | miR-15b* |
| miR-203 | miR-608 | miR-140-5p | miR-15a* |
| miR-205 | miR-612 | miR-151-3p | miR-106a* |
| miR-206 | miR-625 | miR-454 | miR-196a |
| miR-20a | miR-628 | miR-29c | miR-138-2* |
| miR-20b | miR-629 | miR-15a | miR-33b |
| miR-21 | miR-634 | miR-142-5p | miR-301b |
| miR-210 | miR-637 | miR-374a | miR-7-1* |
| miR-214 | miR-638 | miR-193a-3p | miR-30d* |
| miR-22 | miR-642 | miR-151-5p | miR-574-3p |
| miR-220 | miR-645 | miR-744 | miR-18la* |
| miR-221 | miR-647 | miR-BART19-3p | miR-19b-1* |
| miR-222 | miR-649 | miR-378* | miR-20a* |
| miR-224 | miR-652 | miR-340 | miR-9* |
| miR-23a | miR-660 | miR-21* | miR-7 |
| miR-23b | miR-663 | miR-17* | miR-431* |
| miR-24 | miR-671 | miR-142-3p | miR-BART12 |
| miR-25 | miR-765 | miR-193a-5p | miR-153 |
| miR-26a | miR-766 | miR-936 | miR-658 |
| miR-26b | miR-768-3p | miR-193b* | miR-122 |
| miR-27a | miR-768-5p | miR-451 | miR-939 |
| miR-27b | miR-769-3p | miR-921 | miR-181c* |
| miR-28 | miR-769-5p | miR-H1 | miR-885-5p |
| miR-296 | miR-801 | miR-510 | miR-BART11-5p |
| miR-29a | miR-9 | miR-483-5p | miR-BART19-5p |
| miR-29b | miR-92 | miR-150* | miR-BHRF1-2* |

TABLE 8

| Diseases, Disorders and Conditions | | | |
|---|---|---|---|
| Cancers | | | |
| Acute lymphoblastic leukaemia (ALL) | Colorectal cancer | Macroglobulinemia, Waldenstrom | Pleuropulmonary Blastoma, Childhood |
| Acute myeloid leukaemia (AML) | Craniopharyngioma, Childhood | Male Breast Cancer | Pregnancy and Breast Cancer |
| Adrenocortical Carcinoma | Cutaneous T-Cell Lymphoma | Malignant Fibrous Histiocytoma of Bone and Osteosarcoma | Primary Central Nervous System (CNS) Lymphoma |
| AIDS-Related Kaposi Sarcoma | Ductal Carcinoma In Situ (DCIS) | Melanoma | Prostate Cancer |
| AIDS-Related lymphoma | Embryonal Tumors, Childhood | Merkel Cell Carcinoma | Rare cancers |
| Anal Cancer | Endometrial Cancer | Mesothelioma | Rectal Cancer |
| Appendix Cancer | Ependymoma, Childhood | Metastatic Squamous Neck Cancer with Occult Primary | Renal cell carcinoma |
| Astrocytomas, Childhood | Epithelial cancer | Midline Tract Carcinoma Involving NUT Gene | Renal Pelvis and Ureter, Transitional Cell Cancer |
| Atypical Teratoid/Rhabdoid Tumor, Childhood | Esophageal Cancer | Molar pregnancy | Retinoblastoma |

TABLE 8-continued

| Diseases, Disorders and Conditions | | | |
| --- | --- | --- | --- |
| Basal Cell Carcinoma | Esthesioneuroblastoma, Childhood | Mouth and oropharyngeal cancer | Rhabdomyosarcoma |
| Bile duct cancer | Ewing sarcoma | Multiple Endocrine Neoplasia Syndromes, Childhood | Salivary Gland Cancer |
| Bladder cancer | Extragonadal Germ Cell Tumor | Multiple Myeloma/Plasma Cell Neoplasm | Sarcoma |
| Bone cancer | Extrahepatic Bile Duct Cancer | Mycosis Fungoides | Secondary cancers |
| Bowel cancer | Eye Cancer | Myelodysplastic Syndromes | Sezary Syndrome |
| Brain Stem Glioma, Childhood | Gallbladder Cancer | Myelodysplastic/Myelo proliferative Neoplasms | Skin Cancer |
| Brain tumours | Gastric cancer | Myeloproliferative Disorders, Chronic | Skin cancer (non melanoma) |
| Breast cancer | Gastrointestinal Carcinoid Tumor | Nasal Cavity and Paranasal Sinus Cancer | Small Cell Lung Cancer |
| Bronchial Tumors, Childhood | Germ Cell Tumor | Nasopharyngeal cancer | Small Intestine Cancer |
| Burkitt Lymphoma | Gestational trophoblastic tumours (GTT) | Neuroblastoma | Soft Tissue Sarcoma |
| Cancer of unknown primary | Glioma | Non-Hodgkin Lymphoma | Squamous Cell Carcinoma |
| Cancer spread to bone | Hairy cell leukaemia | Non-Small Cell Lung Cancer | Squamous Neck Cancer with Occult Primary, Metastatic |
| Cancer spread to brain | Head and neck cancer | Oesophageal cancer | Stomach (Gastric) Cancer |
| Cancer spread to liver | Heart Cancer, Childhood | Oral Cancer | Stomach cancer |
| Cancer spread to lung | Hepatocellular (Liver) Cancer | Oral Cavity Cancer | T-Cell Lymphoma, Cutancous—scc Mycosis Fungoides and Sézary Syndrome |
| Carcinoid Tumor | Histiocytosis, Langerhans Cell | Oropharyngeal Cancer | Testicular cancer |
| Carcinoma of Unknown Primary | Hodgkin Lymphoma | Osteosarcoma (Bone Cancer) | Throat Cancer |
| Cardiac (Heart) Tumors, Childhood | Hypopharyngeal Cancer | Osteosarcoma and Malignant Fibrous Histiocytoma | Thymoma and Thymic Carcinoma |
| Central Nervous System Atypical Teratoid/Rhabdoid Tumor, Childhood | Intraocular Melanoma | Ovarian Cancer | Thyroid Cancer |
| Central Nervous System Embryonal Tumors, Childhood | Islet Cell Tumors, Pancreatic Neuroendocrine Tumors | Pancreatic Cancer | Transitional Cell Cancer of the Renal Pelvis and Ureter |
| Central Nervous System, Childhood | Kidney cancer | Pancreatic Neuroendocrine Tumors (Islet Cell Tumors) | Unknown primary cancer |
| Cervical cancer | Langerhans Cell Histiocytosis | Papillomatosis, Childhood | Ureter and Renal Pelvis, Transitional Cell Cancer |
| Chordoma, Childhood | Laryngeal Cancer | Paraganglioma | Urethral Cancer |
| Choriocarcinoma | Leukemia | Parathyroid Cancer | Uterine Cancer, Endometrial |
| Chronic Lymphocytic Leukemia (CLL) | Lip and Oral Cavity Cancer | Penile Cancer | Uterine Sarcoma |
| Chronic myeloid leukaemia (CML) | Liver cancer | Pharyngeal Cancer | Vaginal cancer |
| Chronic Myeloproliferative Disorders | Lobular Carcinoma In Situ (LCIS) | Pheochromocytoma | Vulvar Cancer |
| Colon cancer | Low Malignant Potential Tumor | Pituitary Tumor | Waldenstrom Macroglobulinemia |
| Lymphoma | Lung Cancer | Plasma Cell Neoplasm/Multiple Myeloma | Wilms Tumor |

TABLE 8-continued

| Diseases, Disorders and Conditions | | | |
| --- | --- | --- | --- |
| Complement and Immune Complex-Related Diseases | | | |
| Age-related macular degeneration | ANCA-associated vasculitis (Includes Pauci-immune) | Glomerulonephritis— sparse hair— telangiectasis | MYH9-related disease |
| Atypical hemolytic uremic syndrome | Anti-glomerular basement membrane disease (Goodpasture's) | Goodpasture's sndrome | Nail-patella syndrome |
| Autoimmune hemolytic anemia | Arthus Reaction | Granulomatosis with polyangiitis (ANCA and Wegeners) | Nail-patella-like renal disease |
| C1 inhibitor deficiency | Asthma | Guillain-Barre syndrome | Nephritis |
| C1q deficiency | Atypical hemolytic uremic syndrome | Hemolytic angioedema (HAE) | Non-amyloid monoclonal immunoglobulin deposition disease |
| C1r deficiency | Autoimmune inner ear disease (AIED) Sensorineural hearing loss | Henoch-Schonlein purpura | Pauci-immune glomerulonephritis |
| C1s deficiency | Autoimmune uveitis | HIVICK | Pediatric systemic lupus erythematosus |
| C2 deficiency | Autosomal dominant intermediate Charcot-Marie-Tooth disease type E | Hypersensitivty vasculitis | Pierson syndrome |
| C3 deficiency | Behçet disease | Hypocomplementemic urticarial vasculitis | Polyarteritis |
| C4 deficiency | Berger (IgA) Nephropathy | Idiopathic membranous glomerulonephritis | polyarteritis nodosa |
| C5 deficiency | Buergers disease | Idiopathic nephrotic syndrome | Polymyalgia rheumatica |
| C6 deficiency | Central nervous system vasculitis | IgA nephropathy (Berger's disease) | Polymyositis |
| C7 deficiency | Choroiditis | IgA nephropathy/vasculitis (Henoch-Schonlein purpura) | Polymyositis/ dermatomyositis |
| C8 deficiency | Chronic demyelinating polyneuropathy (CIDP) | Immune thrombocytopenia | Poststaphilococcal glomerulonephritis |
| C9 deficiency | Churg-strauss syndrome | Immunobullous diseases | Poststeptococcal glomerulonephritis |
| CD55 deficiency | Cogan's syndrome | Immunotactoid or fibrillary glomerulopathy | Primary membranoproliferative glomerulonephritis |
| CD59 deficiency | Collagen type III glomerulopathy | Infection-related glomerulonephritis | Rapidly progressive glomerulonephritis (Crescentic) |
| Complement Factor I deficiency | Congenital and infantile nephrotic syndrome | Inflammatory myopathies | Rapidly progressive glomerulonephritis (RPGN) |
| Complement factor-H related 1(CFHR1) deficiency | Congenital membranous nephropathy due to maternal anti-neutral endopeptidase alloimmunization | Juvenile dermatomyositis | Rasmussen syndrome |
| Complement factor-H related 3(CFHR3) deficiency | Cryoglobulinaemia/ Cold agglutinin diease | Juvenile polymyositis | Reactive arthritis |
| CR3/CR4 defieciency (leukocyte adhesion deficiency 1) | Cryoglobulinemic vasculitis | Kawasaki disease | Relapsing polychondritis |
| Factor B deficiency | Cutaneous vasculitis | Lipoprotein glomerulopathy | Renal amyloidosis |
| Factor D deficiency | Demyelinating myopathies (paraprotein associated) | Lupus nephritis | Reynolds syndrome |

TABLE 8-continued

| Diseases, Disorders and Conditions | | | |
| --- | --- | --- | --- |
| Factor H deficiency | Denys-Drash syndrome | Lupus nephropathy | Rheumatoid arthritis |
| Factor I deficiency | Dermatomyositis | Can Hegglin anomaly | Sarcoidosis (Nesnier Boeck Schuamann Disease) |
| Ficolin 3 deficiency | Dermatomyositis | Membranoglomerular nephritis | Schimke immuno-osseous dysplasia |
| MASP2 deficiency | Diabetic nephropathy | Membranoproliferative glomerulonephritis | Scleroderma |
| MBL deficiency | Drug-induced immune complex vasculitis | Membranoproliferative glomerulonephritis Type I (MPGN Type I) | Sebastian syndrome |
| Non-alcoholic steatohepatitis | Eosinophilic granulomatosis with polyangiitis (Churgg-Strauss) | Membranoproliferative glomerulonephritis Type II (Dense Deposit Disease, MPGN Type II) | Secondary amyloidosis |
| Paroxysmal nocturnal hemoglobinuria | Epstein Syndrome | Membranoproliferative glomerulonephritis Type III (MPGN Type III | Severe or recurring *C diff* colitis |
| Properdin deficency | Essential mixed cryoglobulinemia | Membranouse glomerulonephritis | Sjogren's syndrome |
| Action myoclonus—renal failure syndrome | Familial Mediterranean fever | Menieres disease | Staphylococcal or streptococcal sepsis |
| Acute respiratory disease syndrome (ARDS)/Severe acute respiratory syndrome (SARS) | Familial renal amyloidosis | Microscopic polyangiitis | Stiff person syndrome |
| Acute serum sickness | Familial steroid-resistant nephrotic syndrome with sensorineural deafness | Minimal change disease | Systemic lupus erythematosus |
| Adult-onset Still disease | Farmer's lung | Mixed connective tissue disease | Systemic sclerosis |
| Age-related macular degeneration | Fechtner Syndrome | Mostly large vessel vasculitis | Takayasu arteritis |
| AL amyloidosis | Fibronectin glomerulopathy | mostly medium vessel vasculitis | Toxic epidermal necrolysis (Stevens Johnson syndrome) |
| Alport's syndrome | Fibrosing alveolitis | Mostly small vessel vsculitis | Transplantation/reperfusion (solid organ) |
| Alzheimer's disease | Focal segmental glomerular | Muckle-Wells syndrome | Vasculitis |
| Amyloidosis (AL, AA, MIDD, Other) | Focal segmental glomerulosclerosis | Myasthenia gravis | Wegener's granulomatosis |
| Giant cell arteritis | Frasier syndrome | Galloway-Mowat syndrome | |
| Type 1 diabetes | Myasthenia gravis | Graves' disease | Pernicious anemia |
| Crohn's disease | alopecia areata | thrombocytopeni purpura | Primary biliary cirrhosis |
| Ulcerative colitis | autoimmune hepatitis | Guillain-Barre syndrome | Psoriasis |
| Inflammatory bowel syndrome | autoimmune deramtomyositis | Autoimmune myocarditis | Rheumatoid arthritis |
| Multiple sclerosis | Juvenile idiopathic arthritis | Autoimmune pemphigus | Vitiligo |
| Enzyme Deficiencies & Vascular Diseases | | | |
| 2,4-dienoyl-CoA reductase deficiency | Fabry disease (1:80,000 to 1:117,000) | Isobutyryl-CoA dehydrogenase | Peripheral neuropathy |
| 2-Methyl-3-hydroxy butyric aciduria | Familial hypercholesterolemia (1:500) | Isovaleric acidemia | Peroxisomal disorders (1:50,000; e.g., Zellweger syndrome, neonatal adrenoleukodystrophy, Refsum's disease) |
| 2-methylbutyryl-CoA dehydrogenase | Familial myocardial infarct/stroke | Lactase deficiency (common) | Phenylketonuria |

TABLE 8-continued

| Diseases, Disorders and Conditions | | | |
| --- | --- | --- | --- |
| 3-hydroxy-3-methylglutaryl (HMG) aciduria | Fatty acid oxidation disorders (1:10,000) | Lesch-Nyhan syndrome | Primary hyperoxaluria |
| 3-methylglutaconic aciduria | Galactokinase deficiency | Lipoprotein lipase deficiency (rare) | Propionic acidemia |
| 3-oxothiolase deficiency (1:100,000) | Galactose epimerase | long-chain 1-3-hdroxyacyl-CoA dehydrogenase | Recurrent emesis |
| 4-hydroxybutyric aciduria | Galactosemia | Lysinuric protein intolerance (rare) | Short-chain acyl-CoA dehydrogenase |
| 5,10-methylenetetrahydrofolate reductase deficiency (common) | Galactosemia (1:40,000) | Lysinuric protein intolerance (rare) | Sucrase-isomaltase deficiency (rare) |
| 5-Oxoprolinuria (pyroglutamic aciduria) | Gaucher's disease | Malonic acidemia | Symptoms of pancreatitis |
| Abetalipoproteinemia (rare) | Glutaric acidemia type I | Maple syrup urine disease | Transferase deficient galactosemia (Galactosemia type 1) |
| Acute Intermittent Porphyria | Glutaric acidemia Type II | Medium chain acyl-CoA dehydrogenase | Trifunctional protein deficiency |
| Alkaptonuria | Glutathione Synthetase Deficiency w/ 5-oxoprolinuria | Medium/short chain L-3-hydroxy acyl-CoA dehydrogenase | Tyrosinemia type 1 |
| Argininemia | Glutathione Synthetase Deficiency w/o 5-oxoprolinuria | Medum-chain ketoacyl-coA thiolase | Tyrosinemia type 2 |
| argininosuccinate aciduria | Glycogenolysis disorders (1:20,000) | Metachromatic leukodystrophy (1:100,000) | Tyrosinemia type 3 |
| Benign hyperphenylalaninemia | Glycogenosis, type I (1:70,000) | Metachromatic leukodystrophy (1:100,000) | Upward gaze paralysis |
| beta ketothiolase deficiency | Hemolytic anemia due to adenylate kinase deficiency | Methylmalonic acidemia (Cbl C) | Very long chain acyl-CoA dehydrogenase |
| Biopterin cofactor biosynthesis defects | Hemolytic anemia due to deficiency in Glucose 6 phosphate dehydrogenase | Methylmalonic acidemia (Cbl D) | Wilson Disease |
| Bioptcrin cofactor regeneration defects | Hemolytic ancmia duc to diphosphoglycerate mutase deficiency | Methylmalonic acidemia (vitamin b12 non-responsive) | Aicardi-Gouticres Syndrome (can be an allelic form of CLE) |
| biotin-unresponsive 3-methylcrotonyl-CoA carboxylase deficiency | Hemolytic anemia due to erythrocyte adenosine deaminase overproduction | Methylmalonic acidemia w/0 homocystinuria | Cutaneous lupus erythematosus |
| Carbamoyl phosphate synthetase | Hemolytic anemia due to glucophosphate isomerase deficiency | Methylmalonic aciduria and homocystinuria | Dermatitis herpetiformis |
| Carnitine acylcarnitine translocase | Hemolytic anemia due to glutathione reductase deficiency | Mitochondrial disorders (1:30,000) | hemophilia A |
| Carnitine palmitoyltransferase I | Hemolytic anemia due to glyceraldehyde-3-phosphate dehydrogenase deficiency | Mitochondrial disorders (1:30,000; e.g., cytochrome-c oxidase deficiency; MELAS syndrome; Pearson's syndrome [all rarel) | hemophilia B |
| Carnitine palmitoyltransferase II | Hemolytic anemia due to pyrimidine 5' nucleotidase deficiency | Mitochondrial disorders (1:30,000; e.g., Leigh disease, Kearns-Sayre syndrome [rare]) | Idiopathic steroid sensitive nephrotic syndrome (same as focal segmental glomerulaosclerosis) |
| Carnitine uptake defect | Hemolytic anemia due to red cell pyruvate kinase deficiency | Mitochondrial disorders (1:30,000; e.g., lipoamide dehydrogenase deficiency [rare]) | Immune thrombocytopeni purpura |

TABLE 8-continued

| Diseases, Disorders and Conditions | | | |
| --- | --- | --- | --- |
| citrullinemia type I | HHH syndrome (rare) | Mitochondrial disorders (1:30,000; e.g., Pearson's syndrome [rare]) | Myasthenia gravis |
| Citrullinemia type II | homocysteinuria | Multiple carboxylase (holocarboxylase synthetase) | Oligoarticular juvenile arthritis |
| Congenital disorders of glycosylation (rare) | Homocystinuria (1:200,000) | Multiple carboxylase deficiency (e.g., holocarboxylase synthetase [rare]) and biotinidase deficiencies (1:60,000) | Scleroderma |
| D-2-hydroxyglutaric aciduria | hyperammonemia/orni-thinemia/citrullinemia (ornithine transporter defect) | Muscle cramps/spasticity | Solar urticaria (maybe protophyria erythema) |
| D-2-hydroxyglutaric-aciduria (rare) | Hyperlipoproteinemia, types I and IV (rare) | Myoadenylate deaminase deficiency (1:100,000) | Thrombotic thrombocytopeni purpura |
| Enteropeptidase deficiency (rare) | Hypermethioninemia due to glycine N-methyltransferase deficiency | Niemann-Pick disease, type C (rare) | Tubulointerstitial nephritis with Uveitis/ATIN |
| Ethylmalonic encephalopathy | Hypermethioninemia encephalopathy due to adenosine kinase deficiency Hyperprolinemia | Nonketotic hyperglycinemia | Von willebrand disease |
| Infectious Diseases & Infectious Agents | | | |
| Acinetobacter | Dengue haemorrhagic fever | Infection-induced immune complex vasculitis | Sepsis |
| *Arcobacter butzleri* infection—blood infection | Disseminated infection with mycobacterium avium complex—blood infection | Klebsiella | Serratia |
| *Arcobacter cryaerophilus* infection—blood infection | *E. coli* | Leprosy/Hansen's disease | *Staphylococcus Aureus* |
| *Arcobacter* infection—blood infection | Enterobacter | Malaria | *Stenotrophomonas maltophilia*—blood infection |
| Bacteremia | *Enterococcus* | Meningococcus | Streptococcal Group A invasive disease—blood infection |
| Bacterial endocarditis | Glanders—blood infection | Methicillin Resistant *Staphylococcus Aureus* | *Streptococcus pneumoniae* |
| Campylobacter fetus infection—blood infection | Gonorrhea | *Pseudomonas* | *Streptococcus pyogenes* |
| Campylobacter jejuni infection—blood infection | Hepatitis | *Rhodococcus equi*—blood infection | Trypanosomiasis |
| Candida | Human Immunodeficiency Virus | Salmonella | Yellow fever |
| Coagulase-negative *Staphylococcus* | | | |

TABLE 9

| Selected Diseases, Receivers and Targets | | | |
| --- | --- | --- | --- |
| Category | Disease | Receiver | Target |
| Amyloidoses | AA Amyloidosis | an an antibody-like binder to serum amyloid A protein or serum amyloid P component | Serum amyloid A protein and amyloid placques |

TABLE 9-continued

Selected Diseases, Receivers and Targets

| Category | Disease | Receiver | Target |
|---|---|---|---|
| Amyloidoses | beta2 microglobulin amyloidosis | an an antibody-like binder to beta-2 microglobulin or serum amyloid P component | Beta2 microglobulin or amyloid placques |
| Amyloidoses | Light chain amyloidosis | an an antibody-like binder to light chain, serum amyloid P component | Antibody light chain or amyloid placques |
| Cell clearance | Cancer | an an antibody-like binder to CD44 | a circulating tumor cell |
| Cell clearance | Cancer | an an antibody-like binder to EpCam | a circulating tumor cell |
| Cell clearance | Cancer | an an antibody-like binder to Her2 | a circulating tumor cell |
| Cell clearance | Cancer | an an antibody-like binder to EGFR | a circulating tumor cell |
| Cell clearance | Cancer (B cell) | an an antibody-like binder to CD20 | a cancerous B cell |
| Cell clearance | Cancer (B cell) | an an antibody-like binder to CD19 | a cancerous B cell |
| Clearance Ab | Antiphospholipid syndrome | beta2-glycoprotein-1 | pathogenic self-antibody against beta2-glycoprotein-1 |
| Clearance Ab | Catastrophic antiphospholipid syndrome | beta2-glycoprotein-1 | pathogenic self-antibody against beta2-glycoprotein-1 |
| Clearance Ab | Cold agglutinin disease | I/i antigen | Pathogenic self-antibody against I/i antigen |
| Clearance Ab | Goodpasture syndrome | a3 NC1 domain of collagen (IV) | pathogenic self-antibody against a3 NC1 domain of Collagen (IV) |
| Clearance Ab | Immune thrombocytopenia purpura | platelet Glycoproteins (Ib-IX, IIb-IIIa, IV, Ia-IIa) | pathogenic self-antibody against platelet glycoprotein |
| Clearance Ab | Membranous Nephropathy | Phospholipase A2 receptor | pathogenic self-antibody against phospholipase A2 receptor |
| Clearance Ab | Warm antibody hemolytic anemia | Glycophorin A, glycophorin B, and/or glycophorin C, Rh antigen | pathogenic self-antibody against glycophorins and/or Rh antigen |
| Complement | Age-related macular degeneration | a suitable complement regulatory protein | active complement |
| Complement | Atypical hemolytic uremic syndrome | complement factor H, or a suitable complement regulatory protein | active complement |
| Complement | Autoimmune hemolytic anemia | a suitable complement regulatory molecule | active complement |
| Complement | Complement Factor I deficiency | Complement factor I, a suitable complement regulatory protein | active complement |
| Complement | Non-alcoholic steatohepatitis | a suitable complement regulatory molecule | active complement |
| Complement | Paroxysmal nocturnal hemoglobinuria | a suitable complement regulatory protein | active complement |
| Enzyme | 3-methylcrotonyl-CoA carboxylase deficiency | 3-methylcrotonyl-CoA carboxylase | 3-hydroxyvaleryl-carnitine, 3-methylcrotonylglycine (3-MCG) and 3-hydroxyisovaleric acid (3-HIVA) |
| Enzyme | Acute Intermittent Porphyria | Porphobilinogen deaminase | Porphobilinogen |
| Enzyme | Acute lymphoblastic leukemia | Asparaginase | Asparagine |
| Enzyme | Acute lymphocytic leukemia, acute myeloid leukemia | Asparaginase | Asparagine |
| Enzyme | Acute myeloblastic leukemia | Asparaginase | Asparagine |

TABLE 9-continued

| Category | Disease | Receiver | Target |
|---|---|---|---|
| | Selected Diseases, Receivers and Targets | | |
| Enzyme | Adenine phosphoribosyl-transferase deficiency | adenine phosphoribosyl-transferase | Insoluble purine 2,8-dihydroxyadenine |
| Enzyme | Adenosine deaminase deficiency | Adenosine deaminase | Adenosine |
| Enzyme | Afibrinogenomia | FI | enzyme replacement |
| Enzyme | Alcohol poisoning | Alcohol dehydrogenase/oxidase | Ethanol |
| Enzyme | Alexander's disease | FVII | enzyme replacement |
| Enzyme | Alkaptonuria | homogentisate oxidase | homogentisate |
| Enzyme | Argininemia | Ammonia monooxygenase | ammonia |
| Enzyme | argininosuccinate aciduria | Ammonia monooxygenasc | ammonia |
| Enzyme | citrullinemia type I | Ammonia monooxygenase | ammonia |
| Enzyme | Citrullinemia type II | Ammonia monooxygenase | ammonia |
| Enzyme | Complete LCAT deficiency, Fish-eye disease, atherosclerosis, hypercholesterolemia | Lecithin-cholesterol acyltransferase (LCAT) | Cholesterol |
| Enzyme | Cyanide poisoning | Thiosulfate-cyanide sulfurtransferase | Cyanide |
| Enzyme | Diabetes | Hexokinase, glucokinase | Glucose |
| Enzyme | Factor II Deficiency | FII | enzyme replacement |
| Enzyme | Familial hyperarginemia | Arginase | Arginine |
| Enzyme | Fibrin Stabilizing factor Def. | FXIII | enzyme replacement |
| Enzyme | Glutaric acidemia type I | lysine oxidase | 3-hydroxyglutaric and glutaric acid (C5-DC), lysine |
| Enzyme | Gout | Uricase | Uric Acid |
| Enzyme | Gout—hyperuricemia | Uricase | Uric acid (Urate crystals) |
| Enzyme | Hageman Def. | FXII | enzyme replacement |
| Enzyme | Hemolytic anemia due to pyrimidine 5' nucleotidase deficiency | pyrimidine 5' nucleotidase | pyrimidines |
| Enzyme | Hemophilia A | Factor VIII | Thrombin (factor II a) or Factor X |
| Enzyme | Hemophilia B | Factor IX | Factor XIa or Factor X |
| Enzyme | Hemophilia C | FXI | enzyme replacement |
| Enzyme | Hepatocellular carcinoma, melanoma | Arginine deiminase | Arginine |
| Enzyme | Homocystinuria | Cystathionine B synthase | homocysteine |
| Enzyme | hyperammonemia/orni-thinemia/citrullinemia (ornithine transporter defect) | Ammonia monooxygenase | Ammonia |
| Enzyme | Isovaleric acidemia | Leucine metabolizing enzyme | leucine |
| Enzyme | Lead poisoning | d-aminolevulinate dehydrogenase | lead |
| Enzyme | Lesch-Nyhan syndrome | Uricase | Uric acid |
| Enzymc | Maple syrup urinc disease | Lcucine metabolizing enzyme | Lucinc |
| Enzyme | Methylmalonic acidemia (vitamin b12 non-responsive) | methylmalonyl-CoA mutase | methylmalonate |
| Enzyme | Mitochondrial neurogastrointestinal encephalomyopathy | thymidine phosphorylase | thymidine |

TABLE 9-continued

| | Selected Diseases, Receivers and Targets | | |
| --- | --- | --- | --- |
| Category | Disease | Receiver | Target |
| Enzyme | Mitochondrial neurogastrointestinal encephalomyopathy (MNGIE) | Thymidine phosphorylase | Thymidine |
| Enzyme | Owren's disease | FV | enzyme replacement |
| Enzyme | p53-null solid tumor | Serine dehyrdatase or serine hydroxymethyl transferase | serine |
| Enzyme | Pancreatic adenocarcinoma | Asparaginase | asparagine |
| Enzyme | Phenylketonuria | Phenylalanine hydroxylase, phenylalanine ammonia lyase | Phenylalanine |
| Enzyme | Primary hyperoxaluria | Oxalate oxidase | Oxalate |
| Enzyme | Propionic acidemia | Propionate conversion enzyme? | Proprionyl coA |
| Enzyme | Purine nucleoside phosphorylase deficiency | Purine nucleoside phosphorylase | Inosine, dGTP |
| Enzyme | Stuart-Power Def. | FX | enzyme replacement |
| Enzyme | Thrombotic Thrombocytopenic Purpura | ADAMTS13 | ultra-large von willebrand factor (ULVWF) |
| Enzyme | Transferase deficient galactosemia (Galactosemia type 1) | galactose dehydrogenase | Galactose-1-phosphate |
| Enzyme | Tyrosinemia type 1 | tyrosine phenol-lyase | tyrosine |
| Enzyme | von Willebrand disease | vWF | enzyme replacement |
| IC clearance | IgA Nephropathy | Complement receptor 1 | Immune complexes |
| IC clearance | Lupus nephritis | Complement receptor 1 | immune complex |
| IC clearance | Systemic lupus erythematosus | Complement receptor 1 | immune complex |
| Infectious | Anthrax (*B. anthracis*) infection | an an antibody-like binder to *B. anthracis* surface protein | *B. anthracis* |
| Infectious | *C. botulinum* infection | an an antibody-like binder to *C. botulinum* surface protein | *C. botulinum* |
| Infectious | *C. difficile* infection | an antibody-like binder to *C. difficile* surface protein | *C. difficile* |
| Infectious | Candida infection | an antibody-like binder to candida surface protein | candida |
| Infectious | *E. coli* infection | an antibody-like binder to *E. coli* surface protein | *E. coli* |
| Infectious | Ebola infection | an antibody-like binder to Ebola surface protein | Ebola |
| Infectious | Hepatitis B (HBV) infection | an antibody-like binder to HBV surface protein | HBV |
| Infectious | Hepatitis C (HCV) infection | an antibody-like binder to HCV surface protein | HCV |
| Infectious | Human immunodeficiency virus (HIV) infection | an antibody-like binder to HIV envelope proteins or CD4 or CCR5 or | HIV |
| Infectious | *M. tuberculosis* infection | an antibody-like binder to *M. tuberculosis* surface protein | *M. tuberculosis* |
| Infectious | Malaria (*P. falciparum*) infection | an antibody-like binder to *P. falciparum* surface protein | *P. falciparum* |
| Lipid | Hepatic lipase deficiency, hypercholesterolemia | Hepatic lipase (LIPC) | Lipoprotein, intermediate density (IDL) |
| Lipid | Hyperalphalipoprotein emia 1 | Cholesteryl ester transfer protein(CETP) | Lipoprotein, high density (HDL) |
| Lipid | hypercholesterolemia | an antibody-like binder to low-density lipoprotein (LDL), LDL receptor | LDL |

TABLE 9-continued

| Selected Diseases, Receivers and Targets | | | |
| --- | --- | --- | --- |
| Category | Disease | Receiver | Target |
| Lipid | hypercholesterolemia | an antibody-like binder to high-density lipoprotein (HDL) or HDL receptor | HDL |
| Lipid | lipoprotein lipase deficiency | lipoprotein lipase | chilomicrons and very low density lipoproteins (VLDL) |
| Lipid | Lipoprotein lipase deficiency, disorders of lipoprotein metabolism | lipoprotein lipase (LPL) | Lipoprotein, very low density (VLDL) |
| Lysosomal storage | Aspartylglucosaminuria (208400) | N-Aspartylglucosaminidase | glycoproteins |
| Lysosomal storage | Cerebrotendinous xanthomatosis (cholestanol lipidosis; 213700) | Sterol 27-hydroxylase | lipids, cholesterol, and bile acid |
| Lysosomal storage | Ceroid lipofuscinosis Adult form (CLN4, Kufs' disease; 204300) | Palmitoyl-protein thioesterase-1 | lipopigments |
| Lysosomal storage | Ceroid lipofuscinosis Infantile form (CLN1, Santavuori-Haltia disease; 256730) | Palmitoyl-protein thioesterase-1 | lipopigments |
| Lysosomal storage | Ceroid lipofuscinosis Juvenile form (CLN3, Batten disease, Vogt-Spielmeyer disease; 204200) | Lysosomal transmembrane CLN3 protein | lipopigments |
| Lysosomal storage | Ceroid lipofuscinosis Late infantile form (CLN2, Jansky-Bielschowsky disease; 204500) | Lysosomal pepstatin-insensitive peptidase | lipopigments |
| Lysosomal storage | Ceroid lipofuscinosis Progressive epilepsy with intellectual disability (600143) | Transmembrane CLN8 protein | lipopigments |
| Lysosomal storage | Ceroid lipofuscinosis Variant late infantile form (CLN6; 601780) | Transmembrane CLN6 protein | lipopigments |
| Lysosomal storage | Ceroid lipofuscinosis Variant late infantile form, Finnish type (CLN5; 256731) | Lysosomal transmembrane CLN5 protein | lipopigments |
| Lysosomal storage | Cholesteryl ester storage disease (CESD) | lisosomal acid lipase | lipids and cholesterol |
| Lysosomal storage | Congenital disorders of N-glycosylation CDG Ia (solely neurologic and neurologic-multivisceral forms; 212065) | Phosphomannomutase-2 | N-glycosylated protein |
| Lysosomal storage | Congenital disorders of N-glycosylation CDG Ib (602579) | Mannose (Man) phosphate (P) isomerase | N-glycosylated protein |
| Lysosomal storage | Congenital disorders of N-glycosylation CDG Ic (603147) | Dolicho-P-Glc:Man9GlcNAc2-PP-dolichol glucosyltransferase | N-glycosylated protein |
| Lysosomal storage | Congenital disorders of N-glycosylation CDG Id (601110) | Dolicho-P-Man:Man5GlcNAc2-PP-dolichol mannosyltransferase | N-glycosylated protein |
| Lysosomal storage | Congenital disorders of N-glycosylation CDG Ie (608799) | Dolichol-P-mannose synthase | N-glycosylated protein |
| Lysosomal storage | Congenital disorders of N-glycosylation CDG If (609180) | Protein involved in mannose-P-dolichol utilization | N-glycosylated protein |

TABLE 9-continued

| Category | Disease | Receiver | Target |
|---|---|---|---|
| Selected Diseases, Receivers and Targets | | | |
| Lysosomal storage | Congenital disorders of N-glycosylation CDG Ig (607143) | Dolichyl-P-mannose:Man-7-GlcNAc-2-PP-dolichyl-α-6-mannosyltransferase | N-glycosylated protein |
| Lysosomal storage | Congenital disorders of N-glycosylation CDG Ih (608104) | Dolichyl-P-glucose:Glc-1-Man-9-GlcNAc-2-PP-dolichyl-α-3-glucosyltransferase | N-glycosylated protein |
| Lysosomal storage | Congenital disorders of N-glycosylation CDG Ii (607906) | α-1,3-Mannosyltransferase | N-glycosylated protein |
| Lysosomal storage | Congenital disorders of N-glycosylation CDG IIa (212066) | Mannosyl-α-1,6-glycoprotein-β-1,2-N-acetylglucosminyltrans-ferase | N-glycosylated protein |
| Lysosomal storage | Congenital disorders of N-glycosylation CDG IIb (606056) | Glucosidase I | N-glycosylated protein |
| Lysosomal storage | Congenital disorders of N-glycosylation CDG IIc (Rambam-Hasharon syndrome; 266265 | GDP-fucose transporter-1 | N-glycosylated protein |
| Lysosomal storage | Congenital disorders of N-glycosylation CDG IId (607091) | β-1,4-Galactosyltransferase | N-glycosylated protein |
| Lysosomal storage | Congenital disorders of N-glycosylation CDG IIe (608779) | Oligomeric Golgi complex-7 | N-glycosylated protein |
| Lysosomal storage | Congenital disorders of N-glycosylation CDG Ij (608093) | UDP-GlcNAc:dolichyl-P NAcGlc phosphotransferase | N-glycosylated protein |
| Lysosomal storage | Congenital disorders of N-glycosylation CDG Ik (608540) | β-1,4-Mannosyltransferase | N-glycosylated protein |
| Lysosomal storage | Congenital disorders of N-glycosylation CDG Il (608776) | α-1,2-Mannosyltransferase | N-glycosylated protein |
| Lysosomal storage | Congenital disorders of N-glycosylation, type I (pre-Golgi glycosylation defects) | α-1,2-Mannosyltransferase | N-glycosylated protein |
| Lysosomal storage | Cystinosis | Cystinosin (lysosomal cystine transporter) | Cysteine |
| Lysosomal storage | Fabry's disease (301500) | Trihexosylceramide α-galactosidase | globotriaosylceramide |
| Lysosomal storage | Farber's disease (lipogranulomatosis; 228000) | Ceramidase | lipids |
| Lysosomal storage | Fucosidosis (230000) | α-L-Fucosidase | fucose and complex sugars |
| Lysosomal storage | Galactosialidosis (Goldberg's syndrome, combined neuraminidase and β-galactosidase deficiency; 256540) | Protective protein/cathepsin A (PPCA) | lysosomal content |
| Lysosomal storage | Gaucher's disease | Glucosylceramide β-glucosidase | sphingolipids |
| Lysosomal storage | Glutamyl ribose-5-phosphate storage disease (305920) | ADP-ribose protein hydrolase | glutamyl ribose 5-phosphate |
| Lysosomal storage | Glycogen storage disease type 2 (Pompe's disease) | alpha glucosidase | glycogen |
| Lysosomal storage | GM1 gangliosidosis, generalized | Ganglioside β-galactosidase | acidic lipid material, gangliosides |
| Lysosomal storage | GM2 activator protein deficiency (Tay-Sachs disease AB variant, GM2A; 272750) | GM2 activator protein | gangliosides |

TABLE 9-continued

Selected Diseases, Receivers and Targets

| Category | Disease | Receiver | Target |
|---|---|---|---|
| Lysosomal storage | GM2 gangliosidosis | Ganglioside β-galactosidase | gangliosides |
| Lysosomal storage | Infantile sialic acid storage disorder (269920) | Na phosphate cotransporter, sialin | sialic acid |
| Lysosomal storage | Krabbe's disease (245200) | Galactosylceramide β-galactosidase | sphingolipids |
| Lysosomal storage | Lysosomal acid lipase deficiency (278000) | Lysosomal acid lipase | cholesteryl esters and triglycerides |
| Lysosomal storage | Metachromatic leukodystrophy (250100) | Arylsulfatase A | sulfatides |
| Lysosomal storage | Mucolipidosis ML II (I-cell disease; 252500) | N-Acetylglucosaminyl-1-phosphotransfeerase catalytic subunit | N-linked glycoproteins |
| Lysosomal storage | Mucolipidosis ML III (pseudo-Hurler's polydystrophy) | N-acetylglucosaminyl-1-phosphotransfeerase | N-linked glycoproteins |
| Lysosomal storage | Mucolipidosis ML III (pseudo-Hurler's polydystrophy) Type III-A (252600) | Catalytic subunit | N-linked glycoproteins |
| Lysosomal storage | Mucolipidosis ML III (pseudo-Hurler's polydystrophy) Type III-C (252605) | Substrate-recognition subunit | N-linked glycoproteins |
| Lysosomal storage | Mucopolysaccharidosis MPS I H/S (Hurler-Scheie syndrome; 607015) | α-1-Iduronidase | glycosaminoglycans |
| Lysosomal storage | Mucopolysaccharidosis MPS I-H (Hurler's syndrome; 607014) | α-1-Iduronidase | glycosaminoglycans |
| Lysosomal storage | Mucopolysaccharidosis MPS II (Hunter's syndrome; 309900) | Iduronate sulfate sulfatase | glycosaminoglycans |
| Lysosomal storage | Mucopolysaccharidosis MPS III (Sanfilippo's syndrome) Type III-A (252900) | Heparan-S-sulfate sulfamidase | glycosaminoglycans |
| Lysosomal storage | Mucopolysaccharidosis MPS III (Sanfilippo's syndrome) Type III-B (252920) | N-acetyl-D-glucosaminidase | glycosaminoglycans |
| Lysosomal storage | Mucopolysaccharidosis MPS III (Sanfilippo's syndrome) Type III-C (252930) | Acetyl-CoA-glucosaminide N-acetyltransferase | glycosaminoglycans |
| Lysosomal storage | Mucopolysaccharidosis MPS III (Sanfilippo's syndrome) Type III-D (252940) | N-acetyl-glucosaminine-6-sulfate sulfatase | glycosaminoglycans |
| Lysosomal storage | Mucopolysaccharidosis MPS I-S (Scheie's syndrome; 607016) | α-1-Iduronidase | glycosaminoglycans |
| Lysosomal storage | Mucopolysaccharidosis MPS IV (Morquio's syndrome) Type IV-A (253000) | Galactosamine-6-sulfate sulfatase | glycosaminoglycans |
| Lysosomal storage | Mucopolysaccharidosis MPS IV (Morquio's syndrome) Type IV-B (253010) | β-Galactosidase | glycosaminoglycans |
| Lysosomal storage | Mucopolysaccharidosis MPS IX (hyaluronidase deficiency; 601492) | Hyaluronidase deficiency | glycosaminoglycans |
| Lysosomal storage | Mucopolysaccharidosis MPS VI (Maroteaux-Lamy syndrome; 253200) | N-Acetyl galactosamine α-4-sulfate sulfatase (arylsulfatase B) | glycosaminoglycans |
| Lysosomal storage | Mucopolysaccharidosis MPS VII (Sly's syndrome; 253220) | β-Glucuronidase | glycosaminoglycans |

TABLE 9-continued

Selected Diseases, Receivers and Targets

| Category | Disease | Receiver | Target |
|---|---|---|---|
| Lysosomal storage | Mucosulfatidosis (multiple sulfatase deficiency; 272200) | Sulfatase-modifying factor-1 | sulfatides |
| Lysosomal storage | Niemann-Pick disease type A | Sphingomyelinase | sphingomyelin |
| Lysosomal storage | Niemann-Pick disease type B | Sphingomyelinase | sphingomyelin |
| Lysosomal storage | Niemann-Pick disease Type C1/Type D ((257220) | NPC1 protein | sphingomyelin |
| Lysosomal storage | Niemann-Pick disease Type C2 (607625) | Epididymal secretory protein 1 (HE1; NPC2 protein) | sphingomyelin |
| Lysosomal storage | Prosaposin deficiency (176801) | Prosaposin | sphingolipids |
| Lysosomal storage | Pycnodysostosis (265800) | Cathepsin K | kinins |
| Lysosomal storage | Sandhoff's disease; 268800 | β-Hexosaminidase B | gangliosides |
| Lysosomal storage | Saposin B deficiency (sulfatide activator deficiency) | Saposin B | sphingolipids |
| Lysosomal storage | Saposin C deficiency (Gaucher's activator deficiency) | Saposin C | sphingolipids |
| Lysosomal storage | Schindler's disease Type I (infantile severe form; 609241) | N-Acetyl-galactosaminidase | glycoproteins |
| Lysosomal storage | Schindler's disease Type II (Kanzaki disease, adult-onset form; 609242) | N-Acetyl-galactosaminidase | glycoproteins |
| Lysosomal storage | Schindler's disease Type III (intermediate form; 609241) | N-Acetyl-galactosaminidase | glycoproteins |
| Lysosomal storage | Sialidosis (256550) | Neuraminidase 1 (sialidase) | mucopolysaccharides and mucolipids |
| Lysosomal storage | Sialuria Finnish type (Salla disease; 604369) | Na phosphate cotransporter, sialin | sialic acid |
| Lysosomal storage | Sialuria French type (269921) | UDP-N-acetylglucosamine-2-epimerase/N-acetylmannosamine kinase, sialin | sialic acid |
| Lysosomal storage | Sphingolipidosis Type I (230500) | Ganglioside β-galactosidase | sphingolipids |
| Lysosomal storage | Sphingolipidosis Type II (juvenile type; 230600) | Ganglioside β-galactosidase | sphingolipids |
| Lysosomal storage | Sphingolipidosis Type III (adult type; 230650) | Ganglioside β-galactosidase | sphingolipids |
| Lysosomal storage | Tay-Sachs disease; 272800 | β-Hexosaminidase A | gangliosides |
| Lysosomal storage | Winchester syndrome (277950) | Metalloproteinase-2 | mucopolysaccharides |
| Lysosomal storage | Wolman's disease | lysosomal acid lipase | lipids and cholesterol |
| Lysosomal storage | α-Mannosidosis (248500), type I (severe) or II (mild) | α-D-Mannosidase | carbohydrates and glycoproteins |
| Lysosomal storage | β-Mannosidosis (248510) | β-D-Mannosidase | carbohydrates and glycoproteins |
| Toxic Molecule | alpha hemolysin poisoning | an antibody-like binder to alpha hemolysin | alpha hemolysin |
| Toxic Molecule | antrax toxin poisoning | an antibody-like binder to anthrax toxin | anthrax toxin |
| Toxic Molecule | bacterial toxin-induced shock | an antibody-like binder to bacterial toxin | bacterial toxin |
| Toxic Molecule | botulinum toxin poisoning | an antibody-like binder to botulinum toxin | botulinum toxin |
| Toxic Molecule | Hemochromatosis (iron poisoning) | iron chelator | molecular iron |

TABLE 9-continued

Selected Diseases, Receivers and Targets

| Category | Disease | Receiver | Target |
| --- | --- | --- | --- |
| Toxic Molecule | Methanol poisoning | Methanol dehdrogenase | Methanol |
| Toxic Molecule | Nerve gas poisoning | Butyryl cholinesterase | Sarin |
| Toxic Molecule | Prion disease caused by PRP | an antibody-like binder to prion protein PRP | Prion protein PRP |
| Toxic Molecule | Prion disease caused by PRPc | an antibody-like binder to prion protein PRPc | Prion protein PRPc |
| Toxic Molecule | Prion disease caused by PRPsc | an antibody-like binder to prion protein PRPsc | Prion protein PRPsc |
| Toxic Molecule | Prion disease cuased by PRPres | an antibody-like binder to prion protein PRPres | Prion protein PRPres |
| Toxic Molecule | Sepsis or cytokine storm | an antibody-like binder to cytokines or Duffy antigen receptor of chemokines (DARC) | cytokines |
| Toxic Molecule | spider venom poisoning | an antibody-like binder to spider venom | spider venom |
| Toxic Molecule | Wilson disease | copper chelator | molecular copper |

---

The invention claimed is:

1. A method of blocking the uptake of therapeutic exosomes in the liver and/or spleen of a subject, the method comprising:

intravenously administering to the subject a first dose comprising non-therapeutic exosomes;

and intravenously administering to the subject a second dose comprising therapeutic exosomes, wherein the intravenous administration of the first dose comprising the non-therapeutic exosomes causes reduced delivery of the therapeutic exosomes to an organ selected from the group consisting of the liver, spleen, and combinations thereof, and causes increased delivery of the therapeutic exosomes to an organ selected from the group consisting of the lung, small intestine, large intestine, stomach, pancreas, and combinations thereof, compared to delivery of the therapeutic exosomes intravenously administered at the same dose, but without prior intravenous administration of the first dose comprising non-therapeutic exosomes, wherein the second dose comprises an exosome quantity of at least about $10^{10}$ exosomes/g by weight of the subject and the first dose is intravenously administered as a bolus dose comprising an exosome quantity that is at least 5 times greater than the second dose, wherein the therapeutic exosomes harbor at least one therapeutic payload or have been modified to have a desired therapeutic effect as compared to non-therapeutic exosomes, wherein the non-therapeutic exosomes do not harbor at least one therapeutic payload as compared to a therapeutic exosome, and wherein the therapeutic and non-therapeutic exosomes are derived from a HEK293 producer cell.

2. The method according to claim 1, wherein the therapeutic exosomes comprise a receiver.

3. The method of claim 1, wherein the second dose is intravenously administered at a period of time which is 15 minutes or greater after intravenous administration of the first dose.

4. The method of claim 1, wherein the non-therapeutic exosomes, the therapeutic exosomes or both the non-therapeutic and therapeutic exosomes comprise an imaging agent.

5. The method of claim 1, wherein the therapeutic exosomes comprise:

(i) an RNA, (ii) a DNA, (iii) a polypeptide, (iv) a polysaccharide, (v) a lipid, (vi) a toxin, or (vii) any combination thereof.

6. The method of claim 1, wherein the therapeutic exosomes comprise a microRNA (miRNA), an siRNA, or an shRNA.

7. The method of claim 1, wherein the therapeutic exosomes comprise more than one distinct payload selected from the group consisting of: a peptide, a protein, a DNA, an siRNA, an miRNA, an shRNA, a polysaccharide, a lipid, a toxin, doxorubicin, daunorubicin, docetaxel, irinotecan, a taxane, a topoisomerase inhibitor, cyclophosphamide, a vinca alkaloid, cisplatin, a retinoid, a nucleotide analog, a kinase inhibitor, and a combination thereof.

8. The method of claim 1, wherein the exosomes are contacted with sialyltransferase prior to intravenous administration.

9. A kit, comprising:

(i) a first pharmaceutical composition comprising non-therapeutic exosomes;

(ii) a second pharmaceutical composition comprising therapeutic exosomes and (iii) instructions for use according to the method of claim 1.

10. The method of claim 1, wherein the therapeutic exosomes comprise doxorubicin, daunorubicin, docetaxel, irinotecan, a taxane, a topoisomerase inhibitor, cyclophosphamide, vinca alkaloid, cisplatin, a retinoid, a nucleotide analog, a kinase inhibitor, or any combination thereof.

11. The method of claim 1, wherein the second dose is intravenously administered as a continuous infusion.

12. The method of claim 1, wherein the second dose is intravenously administered in a plurality of administration steps.

* * * * *

SEQUENCE LISTING

<160> NUMBER OF SEQ ID NOS: 4

<210> SEQ ID NO 1
<211> LENGTH: 5
<212> TYPE: PRT
<213> ORGANISM: Unknown
<220> FEATURE:
<223> OTHER INFORMATION: Description of Unknown:
      Sortase peptide
<220> FEATURE:
<221> NAME/KEY: MOD_RES
<222> LOCATION: (3)..(3)
<223> OTHER INFORMATION: Any amino acid

<400> SEQUENCE: 1

Leu Pro Xaa Thr Gly
1               5

<210> SEQ ID NO 2
<211> LENGTH: 5
<212> TYPE: PRT
<213> ORGANISM: Unknown
<220> FEATURE:
<223> OTHER INFORMATION: Description of Unknown:
      Sortase peptide
<220> FEATURE:
<221> NAME/KEY: MOD_RES
<222> LOCATION: (3)..(3)
<223> OTHER INFORMATION: Any amino acid

<400> SEQUENCE: 2

Leu Pro Xaa Thr Ala
1               5

<210> SEQ ID NO 3
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cgacuggagc acgaggacac ugacauggac ugaaggagua gaaa                         44

-continued

```
<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgacaagagc attgtggaca gtgggac                                          27
```